(12) United States Patent
Moriarity et al.

(10) Patent No.: US 12,281,327 B2
(45) Date of Patent: Apr. 22, 2025

(54) LYMPHOHEMATOPOIETIC ENGINEERING USING CAS9 BASE EDITORS

(71) Applicant: REGENTS OF THE UNIVERSITY OF MINNESOTA, Minneapolis, MN (US)

(72) Inventors: Branden Moriarity, Minneapolis, MN (US); Beau Webber, Minneapolis, MN (US); Cara-Lin Lonetree, Minneapolis, MN (US); Miechaleen Diers, Minneapolis, MN (US); Mitchell Kluesner, Minneapolis, MN (US); Walker Lahr, Minneapolis, MN (US); Emily Joy Pomeroy, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1133 days.

(21) Appl. No.: 16/979,722

(22) PCT Filed: Mar. 13, 2019

(86) PCT No.: PCT/US2019/022049
§ 371 (c)(1),
(2) Date: Sep. 10, 2020

(87) PCT Pub. No.: WO2019/178225
PCT Pub. Date: Sep. 19, 2019

(65) Prior Publication Data
US 2021/0040507 A1    Feb. 11, 2021

Related U.S. Application Data

(60) Provisional application No. 62/642,151, filed on Mar. 13, 2018.

(51) Int. Cl.
| | |
|---|---|
| *C12N 5/078* | (2010.01) |
| *A61K 39/00* | (2006.01) |
| *C12N 5/0783* | (2010.01) |
| *C12N 15/90* | (2006.01) |

(52) U.S. Cl.
CPC ........ *C12N 15/907* (2013.01); *A61K 39/4611* (2023.05); *A61K 39/4631* (2023.05); *A61K 39/464412* (2023.05); *C12N 5/0634* (2013.01); *C12N 5/0636* (2013.01); *C12N 2310/20* (2017.05); *C12N 2510/00* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 2015/0166980 A1 | 6/2015 | Liu | |
| 2015/0166981 A1 | 6/2015 | Liu | |
| 2016/0304846 A1 | 10/2016 | Liu | |
| 2016/0348073 A1 | 12/2016 | Meissner | |
| 2017/0119820 A1* | 5/2017 | Moriarity | ........... C07K 14/4718 |
| 2017/0121693 A1* | 5/2017 | Liu | ........... A61P 21/00 |
| 2022/0340897 A1* | 10/2022 | Lundberg | ............... C12N 15/11 |
| 2024/0110165 A1* | 4/2024 | Zhang | .................. C12N 15/102 |

FOREIGN PATENT DOCUMENTS

| | | |
|---|---|---|
| WO | 2016022363 A2 | 2/2016 |
| WO | 2016168631 A1 | 10/2016 |
| WO | 2017070632 A2 | 4/2017 |
| WO | 2017070633 A2 | 4/2017 |
| WO | 2018035387 | 2/2018 |

OTHER PUBLICATIONS

Ren et al., A Versatile System for Rapid Multiplex Genome-Edited CAR T Cell Generation, Oncotarget, 2017, 8(10):17002-17011.
Andreev, D. E., et al. Oxygen and glucose deprivation induces widespread alterations in mRNA translation within 20 minutes. Genome Biol. 16, 90 (2015).
Billon, P., et al. CRISPR-Mediated Base Editing Enables Efficient Disruption of Eukaryotic Genes through Induction of STOP Codons. Mol. Cell 67, 1068-1079.e4 (2017).
Chapman, J. R., et al. Playing the end game: DNA double-strand break repair pathway choice. Mol. Cell 47, 497-510 (2012).
Denman, C. J., et al. "Membrane-bound IL-21 promotes sustained ex vivo proliferation of human natural killer cells." PloS one 7.1 (2012): e30264.
Ellis, J. Silencing and variegation of gammaretrovirus and lentivirus vectors. Hum. Gene Ther. 16, 1241-1246 (2005).
Eyquem, J., et al. Targeting a CAR to the TRAC locus with CRISPR/Cas9 enhances tumour rejection. Nature 543, 113-117 (2017).
Gardner, L. B. "Hypoxic inhibition of nonsense-mediated RNA decay regulates gene expression and the integrated stress response." Molecular and cellular biology 28.11 (2008): 3729-3741.
Gaudelli, N. M., et al. Programmable base editing of A•T to G•C in genomic DNA without DNA cleavage. Nature 551, 464-471 (2017).
Gibson, D. G. Enzymatic assembly of overlapping DNA fragments. Methods Enzymol. 498, 349-361 (2011).
Haapaniemi, E., et al. CRISPR-Cas9 genome editing induces a p53-mediated DNA damage response. Nat. Med. 24, 927-930 (2018).
Hendel, A., et al. Chemically modified guide RNAs enhance CRISPR-Cas genome editing in human primary cells. Nat. Biotechnol. 33, 985-989 (2015).

(Continued)

*Primary Examiner* — Michail A Belyavskyi
(74) *Attorney, Agent, or Firm* — QUARLES & BRADY LLP

(57) ABSTRACT

Provided herein are methods and systems for targeted gene disruption (knock-out, missense mutation) and targeted gene knock-in in mammalian cells using base editors and guide RNAs (gRNAs) designed to target splice acceptor-splice donor sites. Also provided herein are universally acceptable genetically engineered cells comprising targeted disruptions in immunotherapy-related genes and comprising a CAR/TCR for therapeutic applications.

7 Claims, 36 Drawing Sheets

Specification includes a Sequence Listing.

(56) References Cited

OTHER PUBLICATIONS

Hirano, H., et al. Structure and Engineering of Francisella novicida Cas9. Cell 164, 950-961 (2016).
Hoopes, J. I., et al. APOBEC3A and APOBEC3B Preferentially Deaminate the Lagging Strand Template during DNA Replication. Cell Rep. 14, 1273-1282 (2016).
Ihry, R. J., et al. p53 inhibits CRISPR-Cas9 engineering in human pluripotent stem cells. Nat. Med. 24, 939-946 (2018).
International Searching Authority. International Search Report and Written Opinion for application PCT/US2019/022049. Mailed on Sep. 4, 2019. 18 pages.
Jungreis, I., et al. "Evidence of abundant stop codon readthrough in Drosophila and other metazoa." Genome research 21.12 (2011): 2096-2113.
Khanna, K. K. et al. DNA double-strand breaks: signaling, repair and the cancer connection. Nat. Genet. 27, 247-254 (2001).
Kim, Y. B., et al. Increasing the genome-targeting scope and precision of base editing with engineered Cas9-cytidine deaminase fusions. Nat. Biotechnol. 35, 371-376 (2017).
Kluesner, M. G., et al. EditR: A Method to Quantify Base Editing from Sanger Sequencing. The CRISPR Journal 1, 239-250 (2018).
Kluesner, M. G., et al. "CRISPR-Cas9 cytidine and adenosine base editing of splice-sites mediates highly-efficient disruption of proteins in primary cells." bioRxiv (2020).
Koblan, L. W., et al. Improving cytidine and adenine base editors by expression optimization and ancestral reconstruction. Nat. Biotechnol. (2018). doi:10.1038/nbt.4172.
Kochenderfer, J. N., et al. B-cell depletion and remissions of malignancy along with cytokine-associated toxicity in a clinical trial of anti-CD19 chimeric-antigen-receptor-transduced T cells. Blood blood—2011-10-384388 (2011).
Komor, A. C., et al. Programmable editing of a target base in genomic DNA without double-stranded DNA cleavage. Nature 533, 420-424 (2016).
Komor, A. C., et al. Improved base excision repair inhibition and bacteriophage Mu Gam protein yields C : G-to-T : A base editors with higher efficiency and product purity. 1-10 (2017).
Kosicki, M., et al. Repair of double-strand breaks induced by CRISPR-Cas9 leads to large deletions and complex rearrangements. Nat. Biotechnol. 36, 765 (2018).
Kuscu, C., et al. CRISPR-STOP: gene silencing through base-editing-induced nonsense mutations. Nat. Methods 14, 710-712 (2017).
Lewis, C. A., Jr, et al. Cytosine deamination and the precipitous decline of spontaneous mutation during Earth's history. Proc. Natl. Acad. Sci. U. S. A. 113, 8194-8199 (2016).
Liu, Z., et al. Efficient generation of mouse models of human diseases via ABE- and BE-mediated base editing. Nat. Commun. 9, 2338 (2018).
Loughran, G., et al. Evidence of efficient stop codon readthrough in four mammalian genes. Nucleic Acids Res. 42, 8928-8938 (2014).

Mahnke, Y. D., et al. The who's who of T-cell differentiation: Human memory T-cell subsets. Eur. J. Immunol. 43, 2797-2809 (2013).
Osborn, M. J., et al. Evaluation of TCR Gene Editing Achieved by TALENs, CRISPR/Cas9, and megaTAL Nucleases. Mol. Ther. 24, 570-581 (2016).
Philip, B., et al. A highly compact epitope-based marker/suicide gene for easier and safer T-cell therapy. Blood 124, 1277-1287 (2014).
Porter, D. L., et al. Chimeric antigen receptor-modified T cells in chronic lymphoid leukemia. N. Engl. J. Med. 365, 725-733 (2011).
Provasi, E., et al. Editing T cell specificity towards leukemia by zinc finger nucleases and lentiviral gene transfer. Nat. Med. 18, 807-815 (2012).
Qasim, W., et al. Molecular remission of infant B-ALL after infusion of universal TALEN gene-edited CAR T cells. Sci. Transl. Med. 9, (2017).
Ran, F. A., et al. Double nicking by RNA-guided CRISPR Cas9 for enhanced genome editing specificity. Cell 154, 1380-1389 (2013).
Ren, J., et al. Multiplex Genome Editing to Generate Universal CAR T Cells Resistant to PD1 Inhibition. Clin. Cancer Res. 23, 2255-2266 (2017).
Scotti, M. M. et al. RNA mis-splicing in disease. Nat. Rev. Genet. 17, 19-32 (2016).
Shah, S. A., et al. "Protospacer recognition motifs: mixed identities and functional diversity." RNA biology 10.5 (2013): 891-899.
Shin, H. Y., et al. CRISPR/Cas9 targeting events cause complex deletions and insertions at 17 sites in the mouse genome. Nat Commun 8: 15464. (2017).
Tsai, S. Q., et al. GUIDE-seq enables genome-wide profiling of off-target cleavage by CRISPR-Cas nucleases. Nat. Biotechnol. 33, 187-197 (2015).
Von Kalle, C., et al. Vector integration and tumorigenesis. Hum. Gene Ther. 25, 475-481 (2014).
WAGNER Jr, J. E., et al. "Phase I/II trial of StemRegenin-1 expanded umbilical cord blood hematopoietic stem cells supports testing as a stand-alone graft." Cell stem cell 18.1 (2016): 144-155.
Wang, L., et al. Enhanced base editing by co-expression of free uracil DNA glycosylase inhibitor. Cell Res. 27, 1289-1292 (2017).
Wang, X., et al. CRISPR-DAV: CRISPR NGS data analysis and visualization pipeline. Bioinformatics 33, 3811-3812 (2017).
Webber, B. R., et al. "Highly efficient multiplex human T cell engineering without double-strand breaks using Cas9 pase editors." Nature communications 10.1 (2019): 1-10.
Webber, B. R., et al. "Rapid generation of Col7a1-/- mouse model of recessive dystrophic epidermolysis bullosa and partial rescue via immunosuppressive dermal mesenchymal stem cells." Laboratory Investigation 97.10 (2017): 1218-1224.
Zafra, M. P., et al. Optimized base editors enable efficient editing in cells, organoids and mice. Nat. Biotechnol. (2018). doi:10.1038/nbt.4194.
Hess, et al., "Methods and Applications of CRISPR-Mediated Base Editing in Eukaryotic Genomes", Molecular Cell, 68-1, p. 26-43. 2017.

* cited by examiner

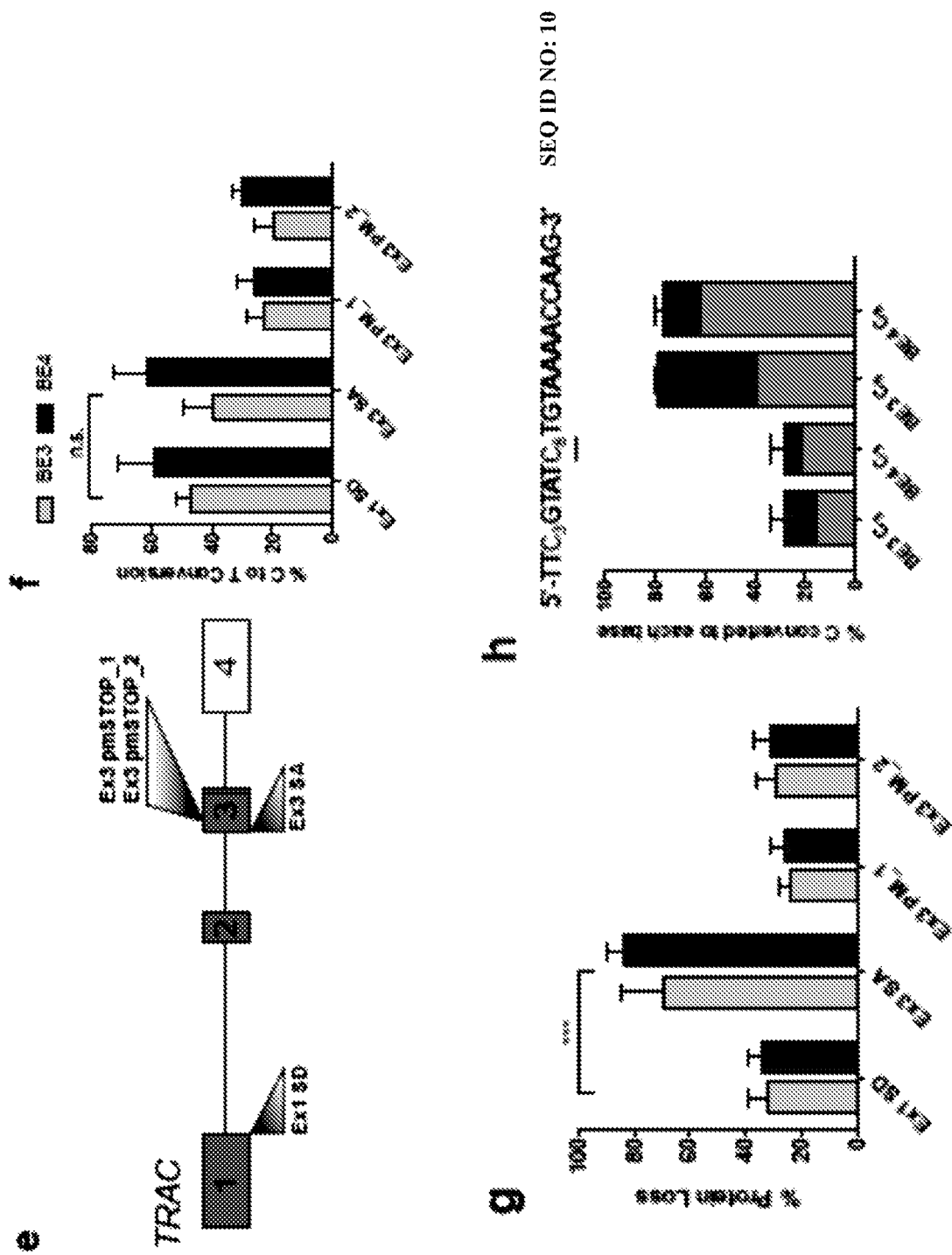
FIGS. 3A-3L, CONTINUED

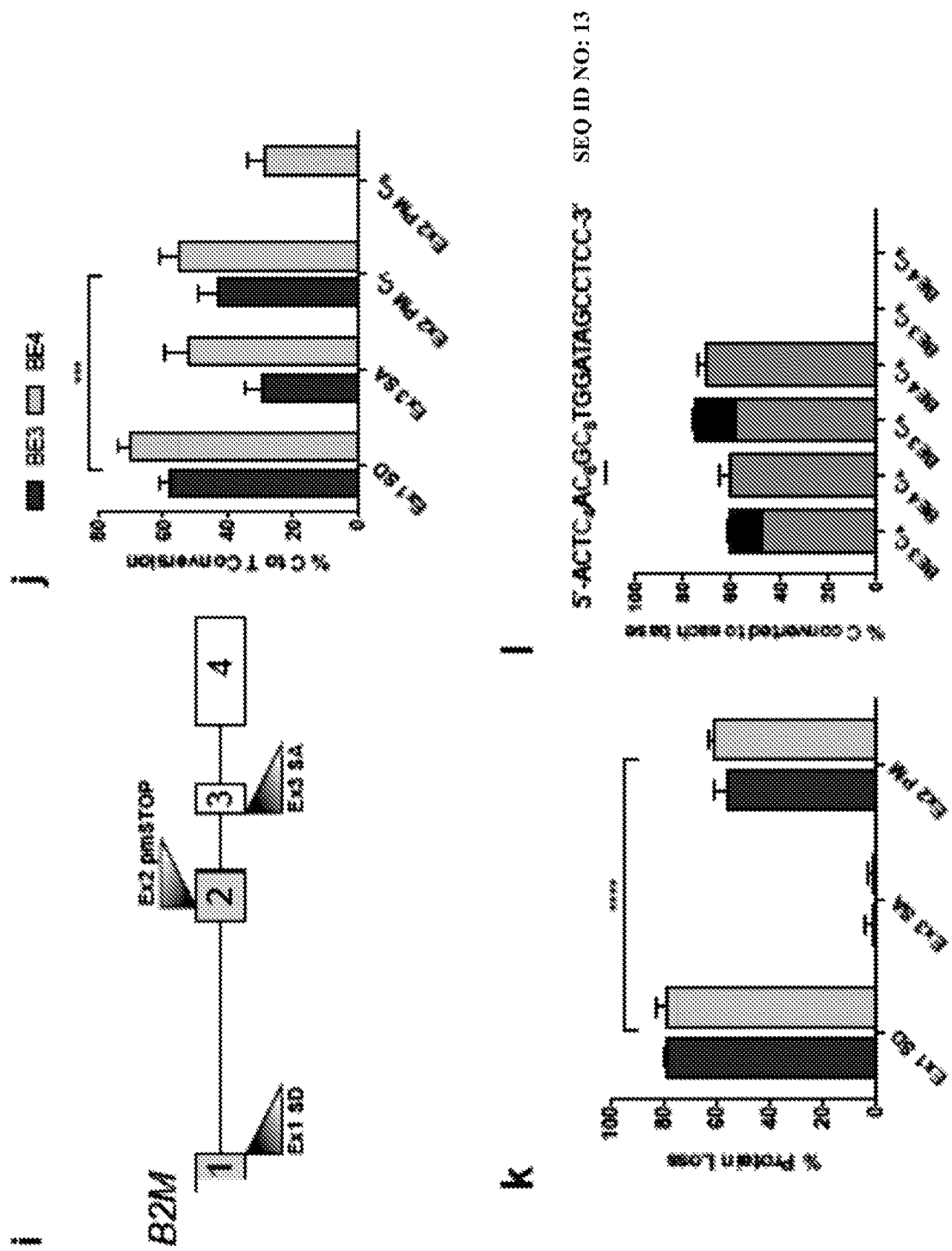
FIGS. 3A-3L, CONTINUED

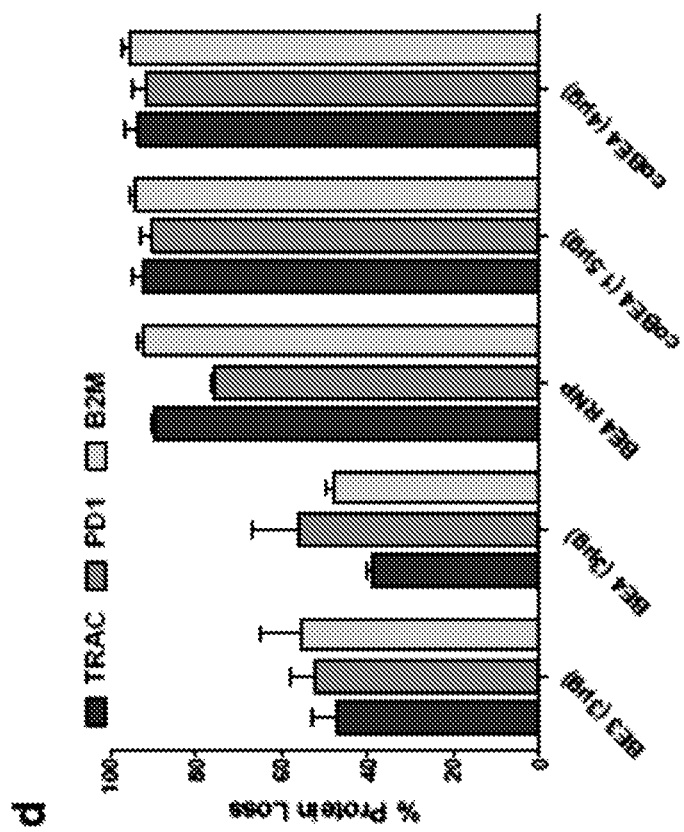
FIG. 4A-4F, CONTINUED

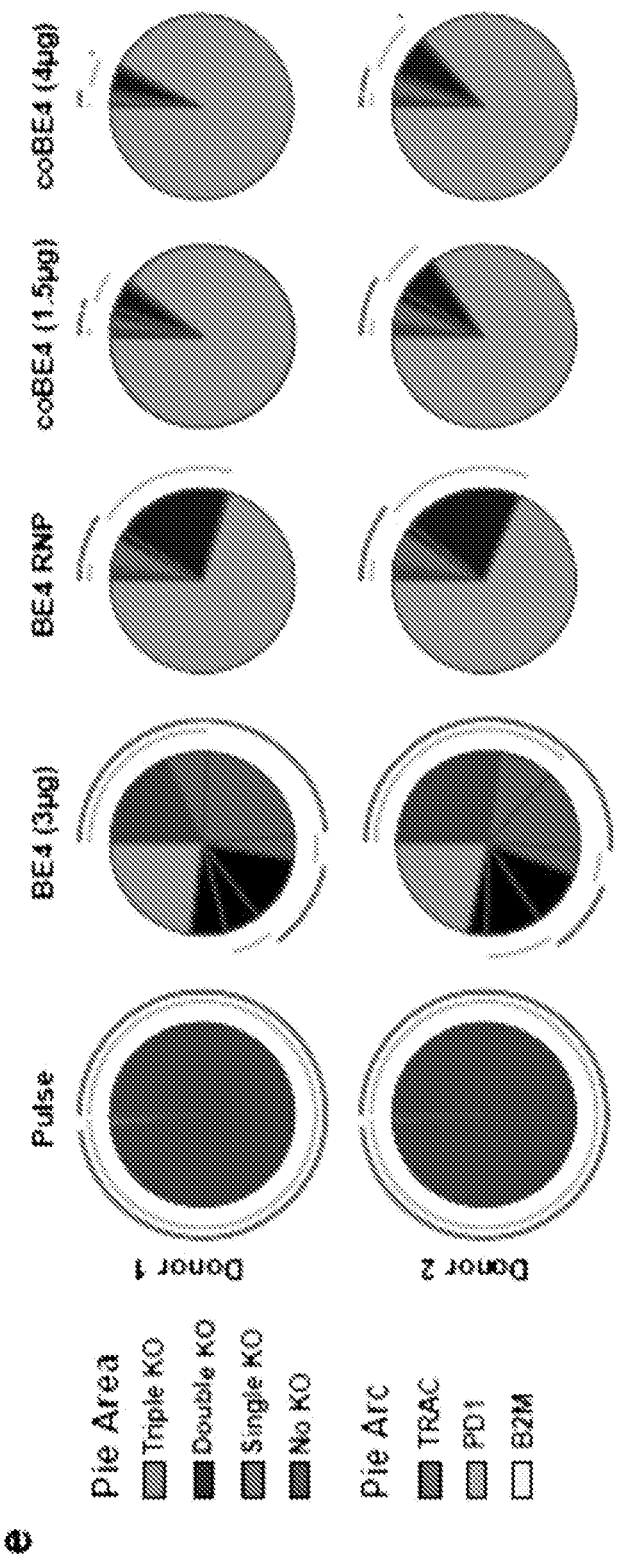
FIG. 4A-4F, CONTINUED

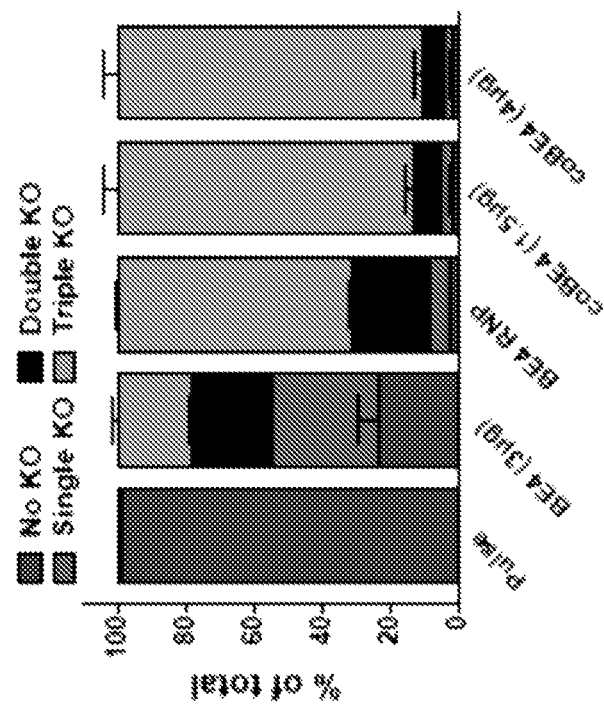
FIG. 4A-4F, CONTINUED

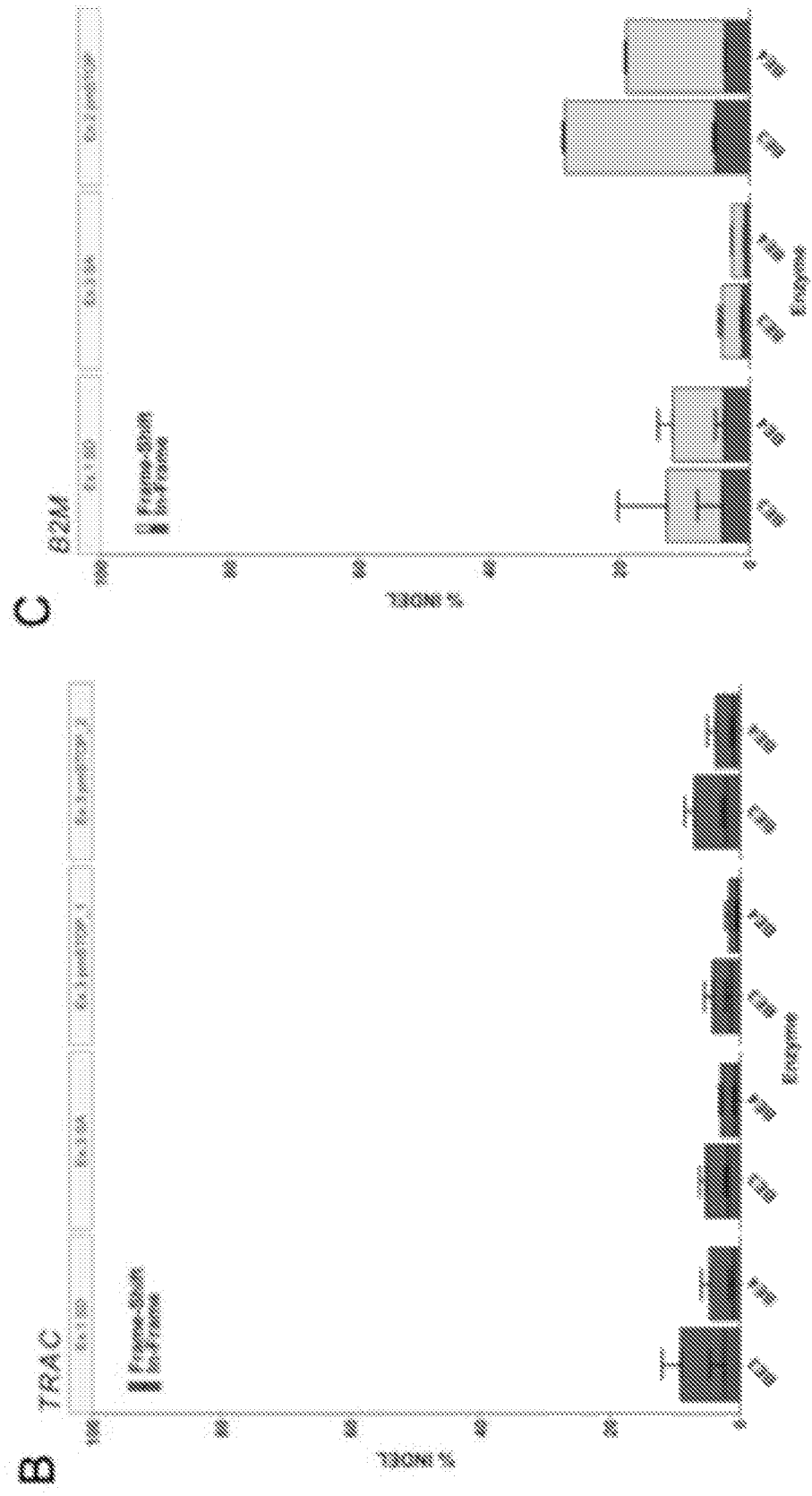
FIGS. 8A-8C, CONTINUED

FIGS. 17A-17B, CONTINUED
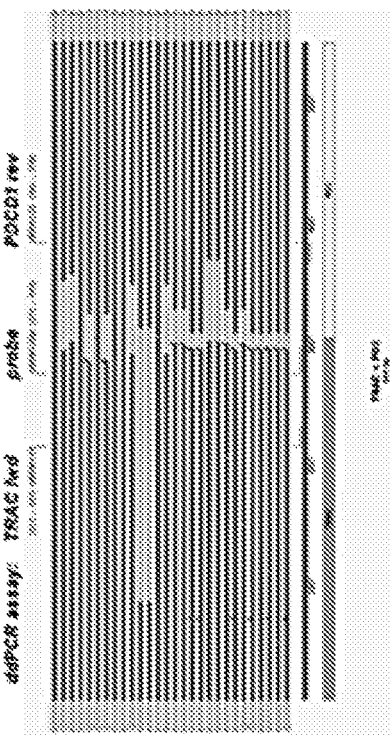
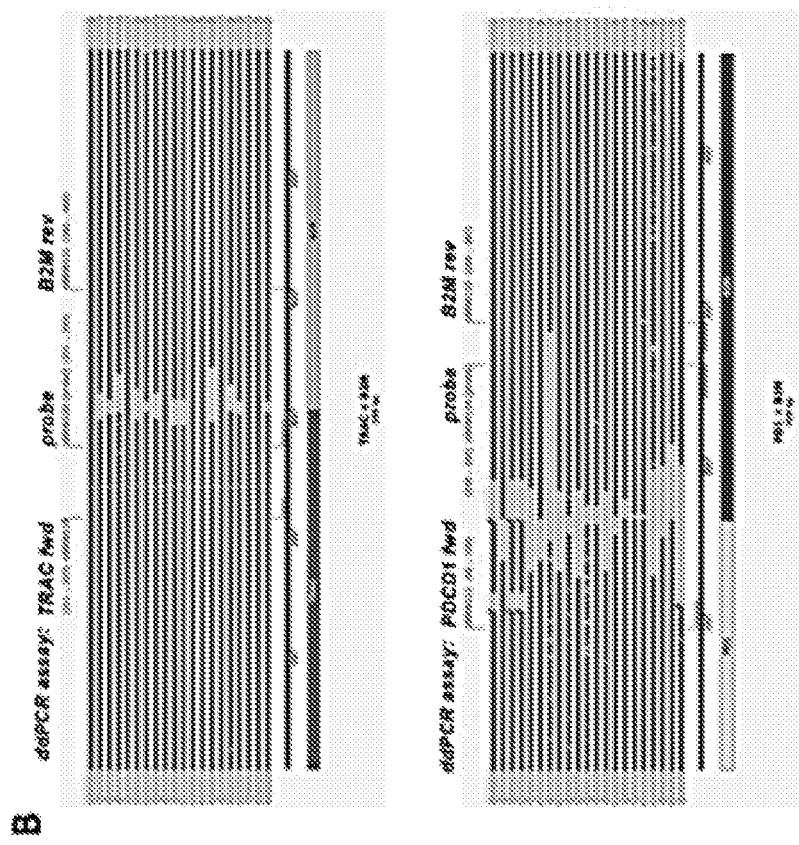

FIGS. 18A-18D, CONTINUED
D.
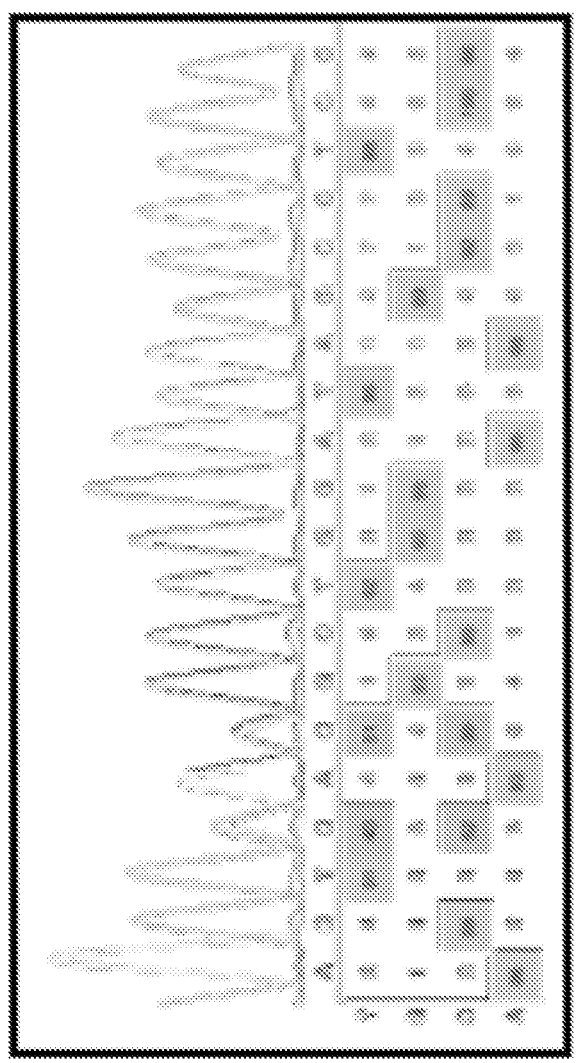

FIGS. 21A-21D, CONTINUED
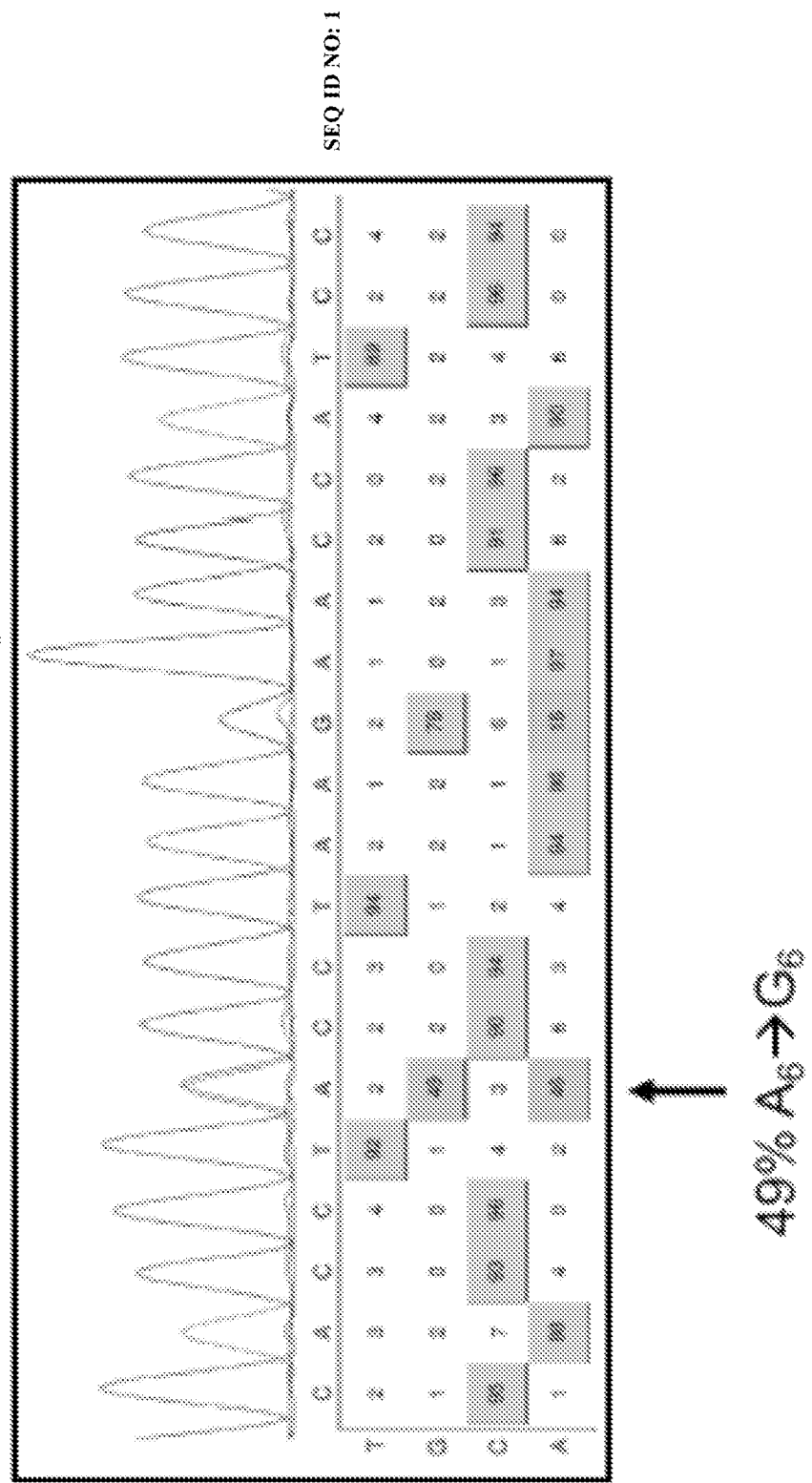

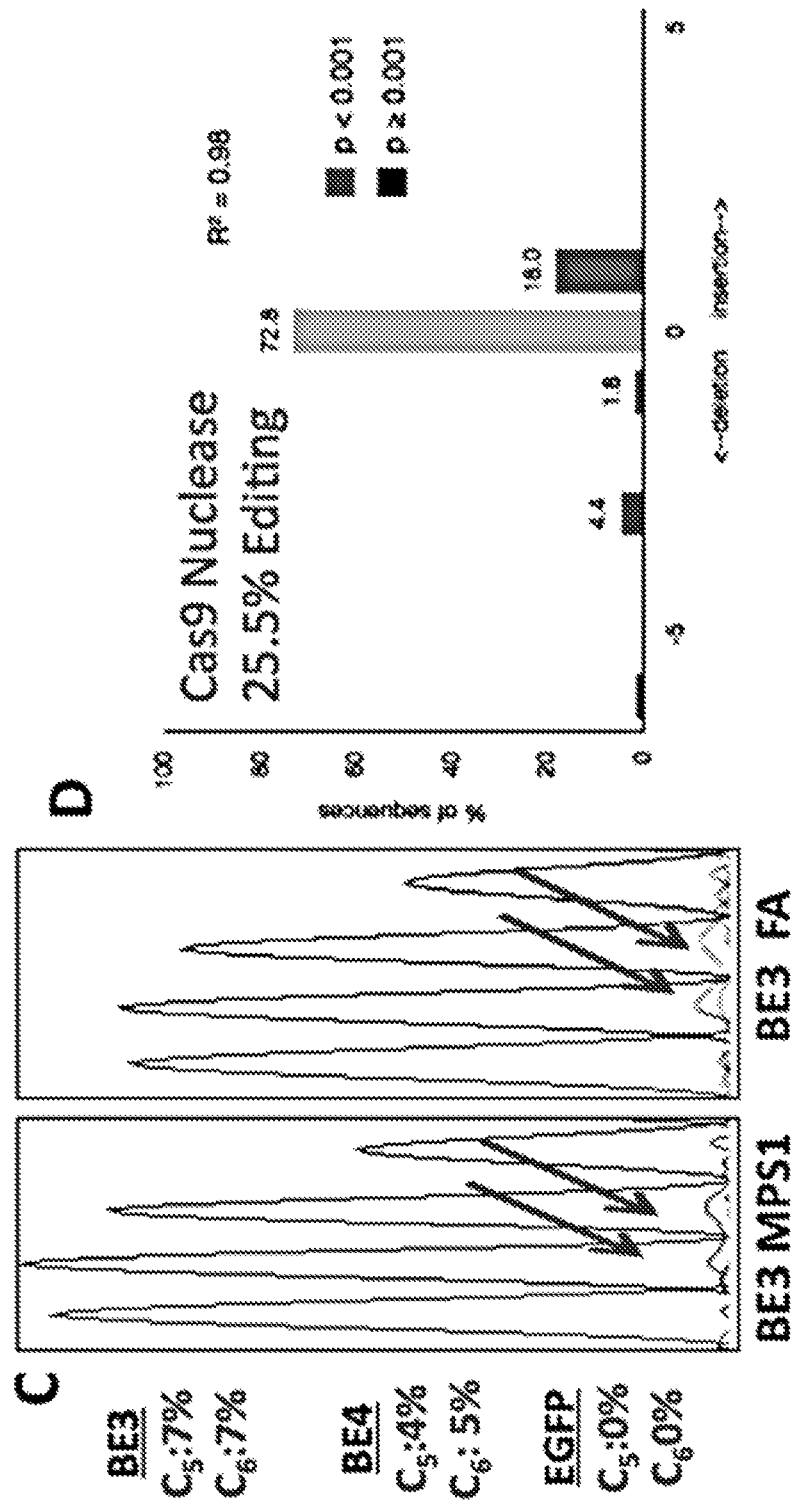
FIGS. 21A-21D, CONTINUED

SEQUENCE LISTING

```
<160> NUMBER OF SEQ ID NOS: 179

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
cacctaccta agaaccatcc                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
ggagtctgag agatggagag                                               20

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
ttctctctgg aagggcacaa                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
gacgttacct cgtgcggccc                                               20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
cctgcagaga aacacacttg                                               20

<210> SEQ ID NO 6
<211> LENGTH: 20
<212> TYPE: DNA
<213> ORGANISM: Artificial Sequence
<220> FEATURE:
```

<223> OTHER INFORMATION: synthetic

<400> SEQUENCE: 6
ggggttccag ggcctgtctg                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
cagttccaaa ccctggtggt                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
ggacccagac tagcagcacc                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
cttacctggg ctggggaaga                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
ttcgtatctg taaaaccaag                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
tttcaaaacc tgtcagtgat                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic

<400> SEQUENCE: 12
ttcaaaacct gtcagtgatt                                              20

```
<210> SEQ ID NO 13
<211> LENGTH: 20
<212> TYPE: DNA
<213> ORGANISM: Artificial Sequence
<220> FEATURE:
<223> OTHER INFORMATION: synthetic

<400> SEQUENCE: 13
actcacgctg gatagcctcc                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic

<400> SEQUENCE: 14
tcgatctatg aaaaagacag                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
cttaccccac ttaactatct                                              20

<210> SEQ ID NO 16
<211> LENGTH: 51
<212> TYPE: DNA
<213> ORGANISM: Artificial Sequence
<220> FEATURE:
<223> OTHER INFORMATION: synthetic

<400> SEQUENCE: 16
tcgtcggcag cgtcagatgt gtataagaga cagatccagc cctggactag c           51

<210> SEQ ID NO 17
<211> LENGTH: 54
<212> TYPE: DNA
<213> ORGANISM: Artificial Sequence
<220> FEATURE:
<223> OTHER INFORMATION: synthetic

<400> SEQUENCE: 17
gtctcgtggg ctcggagatg tgtataagag acagctctct ctaacctggc actg        54

<210> SEQ ID NO 18
<211> LENGTH: 54
<212> TYPE: DNA
<213> ORGANISM: Artificial Sequence
<220> FEATURE:
<223> OTHER INFORMATION: synthetic

<400> SEQUENCE: 18
gtctcgtggg ctcggagatg tgtataagag acagcctctc tctaacctgg cact        54

<210> SEQ ID NO 19
<211> LENGTH: 53
<212> TYPE: DNA
<213> ORGANISM: Artificial Sequence
<220> FEATURE:
<223> OTHER INFORMATION: synthetic
```

<400> SEQUENCE: 19
tcgtcggcag cgtcagatgt gtataagaga cagcccagac atgagaaggt tat    53

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
tctgcccctg gatagcctcc    20

<210> SEQ ID NO 21
<211> LENGTH: 52
<212> TYPE: DNA
<213> ORGANISM: Artificial Sequence
<220> FEATURE:
<223> OTHER INFORMATION: synthetic

<400> SEQUENCE: 21
gtctcgtggg ctcggagatg tgtataagag acagctttac aggctcccct tc    52

<210> SEQ ID NO 22
<211> LENGTH: 53
<212> TYPE: DNA
<213> ORGANISM: Artificial Sequence
<220> FEATURE:
<223> OTHER INFORMATION: synthetic

<400> SEQUENCE: 22
gtctcgtggg ctcggagatg tgtataagag acaggtctag gcgtcctcat cac    53

<210> SEQ ID NO 23
<211> LENGTH: 53
<212> TYPE: DNA
<213> ORGANISM: Artificial Sequence
<220> FEATURE:
<223> OTHER INFORMATION: synthetic

<400> SEQUENCE: 23
tcgtcggcag cgtcagatgt gtataagaga cagggatgtt ctttggtgtt tgt    53

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
actcaccttc catagcctcc    20

<210> SEQ ID NO 25
<211> LENGTH: 54
<212> TYPE: DNA
<213> ORGANISM: Artificial Sequence
<220> FEATURE:
<223> OTHER INFORMATION: synthetic

<400> SEQUENCE: 25
gtctcgtggg ctcggagatg tgtataagag acaggactcc gtctctgaac actc    54

<210> SEQ ID NO 26
<211> LENGTH: 53

```
<212> TYPE: DNA
<213> ORGANISM: Artificial Sequence
<220> FEATURE:
<223> OTHER INFORMATION: synthetic

<400> SEQUENCE: 26
tcgtcggcag cgtcagatgt gtataagaga caggaatgtt gggatgttct ttg            53

<210> SEQ ID NO 27
<211> LENGTH: 53
<212> TYPE: DNA
<213> ORGANISM: Artificial Sequence
<220> FEATURE:
<223> OTHER INFORMATION: synthetic

<400> SEQUENCE: 27
tcgtcggcag cgtcagatgt gtataagaga cagatagttg ccatttctgc ttg            53

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
gctcctgctg catagcctcc                                                 20

<210> SEQ ID NO 29
<211> LENGTH: 54
<212> TYPE: DNA
<213> ORGANISM: Artificial Sequence
<220> FEATURE:
<223> OTHER INFORMATION: synthetic

<400> SEQUENCE: 29
gtctcgtggg ctcggagatg tgtataagag acaggagggt gaaagactga aaaa           54

<210> SEQ ID NO 30
<211> LENGTH: 53
<212> TYPE: DNA
<213> ORGANISM: Artificial Sequence
<220> FEATURE:
<223> OTHER INFORMATION: synthetic

<400> SEQUENCE: 30
tcgtcggcag cgtcagatgt gtataagaga cagaatagtt gccatttctg ctt            53

<210> SEQ ID NO 31
<211> LENGTH: 53
<212> TYPE: DNA
<213> ORGANISM: Artificial Sequence
<220> FEATURE:
<223> OTHER INFORMATION: synthetic

<400> SEQUENCE: 31
tcgtcggcag cgtcagatgt gtataagaga cagtcttttt gtgaaggctt ttc            53

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
```
tctcactgtg gttagcctcc                                            20

<210> SEQ ID NO 33
<211> LENGTH: 54
<212> TYPE: DNA
<213> ORGANISM: Artificial Sequence
<220> FEATURE:
<223> OTHER INFORMATION: synthetic

<400> SEQUENCE: 33
gtctcgtggg ctcggagatg tgtataagag acagtttgtc accagctgat tgta      54

<210> SEQ ID NO 34
<211> LENGTH: 54
<212> TYPE: DNA
<213> ORGANISM: Artificial Sequence
<220> FEATURE:
<223> OTHER INFORMATION: synthetic

<400> SEQUENCE: 34
gtctcgtggg ctcggagatg tgtataagag acagtgtcac cagctgattg taga      54

<210> SEQ ID NO 35
<211> LENGTH: 53
<212> TYPE: DNA
<213> ORGANISM: Artificial Sequence
<220> FEATURE:
<223> OTHER INFORMATION: synthetic

<400> SEQUENCE: 35
tcgtcggcag cgtcagatgt gtataagaga cagctcaaga gcaagaaacc agt       53

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
tctctcactg gatagcctac                                            20

<210> SEQ ID NO 37
<211> LENGTH: 54
<212> TYPE: DNA
<213> ORGANISM: Artificial Sequence
<220> FEATURE:
<223> OTHER INFORMATION: synthetic

<400> SEQUENCE: 37
gtctcgtggg ctcggagatg tgtataagag acagaggact ttgaaatacc agca      54

<210> SEQ ID NO 38
<211> LENGTH: 52
<212> TYPE: DNA
<213> ORGANISM: Artificial Sequence
<220> FEATURE:
<223> OTHER INFORMATION: synthetic

<400> SEQUENCE: 38
tcgtcggcag cgtcagatgt gtataagaga caggtgagtc agcagctcaa ga        52

<210> SEQ ID NO 39
<211> LENGTH: 51
<212> TYPE: DNA
<213> ORGANISM: Artificial Sequence

```
<220> FEATURE:
<223> OTHER INFORMATION: synthetic

<400> SEQUENCE: 39
tcgtcggcag cgtcagatgt gtataagaga cagagctcag cttgctccac t        51

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
agccaccctg gagagcctcc                                            20

<210> SEQ ID NO 41
<211> LENGTH: 52
<212> TYPE: DNA
<213> ORGANISM: Artificial Sequence
<220> FEATURE:
<223> OTHER INFORMATION: synthetic

<400> SEQUENCE: 41
gtctcgtggg ctcggagatg tgtataagag acaggcttct tgaggctgtt ca        52

<210> SEQ ID NO 42
<211> LENGTH: 53
<212> TYPE: DNA
<213> ORGANISM: Artificial Sequence
<220> FEATURE:
<223> OTHER INFORMATION: synthetic

<400> SEQUENCE: 42
gtctcgtggg ctcggagatg tgtataagag acagcttctt gaggctgttc agg       53

<210> SEQ ID NO 43
<211> LENGTH: 51
<212> TYPE: DNA
<213> ORGANISM: Artificial Sequence
<220> FEATURE:
<223> OTHER INFORMATION: synthetic

<400> SEQUENCE: 43
tcgtcggcag cgtcagatgt gtataagaga cagctttcgc cagctcaaaa a         51

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
actcccgctg gaaagcctgc                                            20

<210> SEQ ID NO 45
<211> LENGTH: 52
<212> TYPE: DNA
<213> ORGANISM: Artificial Sequence
<220> FEATURE:
<223> OTHER INFORMATION: synthetic

<400> SEQUENCE: 45
gtctcgtggg ctcggagatg tgtataagag acagcagcga gctctactgg tg        52
```

<210> SEQ ID NO 46
<211> LENGTH: 52
<212> TYPE: DNA
<213> ORGANISM: Artificial Sequence
<220> FEATURE:
<223> OTHER INFORMATION: synthetic

<400> SEQUENCE: 46
gtctcgtggg ctcggagatg tgtataagag acagcgagct ctactggtgc tg            52

<210> SEQ ID NO 47
<211> LENGTH: 53
<212> TYPE: DNA
<213> ORGANISM: Artificial Sequence
<220> FEATURE:
<223> OTHER INFORMATION: synthetic

<400> SEQUENCE: 47
tcgtcggcag cgtcagatgt gtataagaga cagggtggat tacaatggaa aca           53

<210> SEQ ID NO 48
<211> LENGTH: 20
<212> TYPE: DNA
<213> ORGANISM: Artificial Sequence
<220> FEATURE:
<223> OTHER INFORMATION: synthetic

<400> SEQUENCE: 48
cctcccgctg tgtagcctcc                                                20

<210> SEQ ID NO 49
<211> LENGTH: 54
<212> TYPE: DNA
<213> ORGANISM: Artificial Sequence
<220> FEATURE:
<223> OTHER INFORMATION: synthetic

<400> SEQUENCE: 49
gtctcgtggg ctcggagatg tgtataagag acagcatgaa aggggttat acat           54

<210> SEQ ID NO 50
<211> LENGTH: 54
<212> TYPE: DNA
<213> ORGANISM: Artificial Sequence
<220> FEATURE:
<223> OTHER INFORMATION: synthetic

<400> SEQUENCE: 50
tcgtcggcag cgtcagatgt gtataagaga cagggattac aatggaaaca tcaa          54

<210> SEQ ID NO 51
<211> LENGTH: 51
<212> TYPE: DNA
<213> ORGANISM: Artificial Sequence
<220> FEATURE:
<223> OTHER INFORMATION: synthetic

<400> SEQUENCE: 51
tcgtcggcag cgtcagatgt gtataagaga cagctgccag ggactgagag t             51

<210> SEQ ID NO 52
<211> LENGTH: 20
<212> TYPE: DNA
<213> ORGANISM: Artificial Sequence
<220> FEATURE:
<223> OTHER INFORMATION: synthetic

<400> SEQUENCE: 52
cacctaccta agaaccatcc                                                    20

<210> SEQ ID NO 53
<211> LENGTH: 52
<212> TYPE: DNA
<213> ORGANISM: Artificial Sequence
<220> FEATURE:
<223> OTHER INFORMATION: synthetic

<400> SEQUENCE: 53
gtctcgtggg ctcggagatg tgtataagag acaggtggat gtggaggaag ag                52

<210> SEQ ID NO 54
<211> LENGTH: 52
<212> TYPE: DNA
<213> ORGANISM: Artificial Sequence
<220> FEATURE:
<223> OTHER INFORMATION: synthetic

<400> SEQUENCE: 54
gtctcgtggg ctcggagatg tgtataagag acagacgtgg atgtggagga ag                52

<210> SEQ ID NO 55
<211> LENGTH: 53
<212> TYPE: DNA
<213> ORGANISM: Artificial Sequence
<220> FEATURE:
<223> OTHER INFORMATION: synthetic

<400> SEQUENCE: 55
tcgtcggcag cgtcagatgt gtataagaga cagtttcact tctatcccac acc               53

<210> SEQ ID NO 56
<211> LENGTH: 20
<212> TYPE: DNA
<213> ORGANISM: Artificial Sequence
<220> FEATURE:
<223> OTHER INFORMATION: synthetic

<400> SEQUENCE: 56
cggccacctg agaaccatcc                                                    20

<210> SEQ ID NO 57
<211> LENGTH: 54
<212> TYPE: DNA
<213> ORGANISM: Artificial Sequence
<220> FEATURE:
<223> OTHER INFORMATION: synthetic

<400> SEQUENCE: 57
gtctcgtggg ctcggagatg tgtataagag acagaaagtt ctctggttcc tgtg              54

<210> SEQ ID NO 58
<211> LENGTH: 51
<212> TYPE: DNA
<213> ORGANISM: Artificial Sequence
<220> FEATURE:
<223> OTHER INFORMATION: synthetic

<400> SEQUENCE: 58
tcgtcggcag cgtcagatgt gtataagaga cagggggccac ttgtgctaga g                51

<210> SEQ ID NO 59

<211> LENGTH: 20
<212> TYPE: DNA
<213> ORGANISM: Artificial Sequence
<220> FEATURE:
<223> OTHER INFORMATION: synthetic

<400> SEQUENCE: 59
acctgaccta agaaccatcc                                              20

<210> SEQ ID NO 60
<211> LENGTH: 54
<212> TYPE: DNA
<213> ORGANISM: Artificial Sequence
<220> FEATURE:
<223> OTHER INFORMATION: synthetic

<400> SEQUENCE: 60
gtctcgtggg ctcggagatg tgtataagag acagactagt gcccatgata gcag         54

<210> SEQ ID NO 61
<211> LENGTH: 53
<212> TYPE: DNA
<213> ORGANISM: Artificial Sequence
<220> FEATURE:
<223> OTHER INFORMATION: synthetic

<400> SEQUENCE: 61
tcgtcggcag cgtcagatgt gtataagaga cagcatgtac acgtctgacc act          53

<210> SEQ ID NO 62
<211> LENGTH: 55
<212> TYPE: DNA
<213> ORGANISM: Artificial Sequence
<220> FEATURE:
<223> OTHER INFORMATION: synthetic

<400> SEQUENCE: 62
gtctcgtggg ctcggagatg tgtataagag acaggaattt actagtgccc atgat        55

<210> SEQ ID NO 63
<211> LENGTH: 53
<212> TYPE: DNA
<213> ORGANISM: Artificial Sequence
<220> FEATURE:
<223> OTHER INFORMATION: synthetic

<400> SEQUENCE: 63
tcgtcggcag cgtcagatgt gtataagaga cagacactaa cgattgctga tga          53

<210> SEQ ID NO 64
<211> LENGTH: 20
<212> TYPE: DNA
<213> ORGANISM: Artificial Sequence
<220> FEATURE:
<223> OTHER INFORMATION: synthetic

<400> SEQUENCE: 64
cttctatctc agaaccatcc                                              20

<210> SEQ ID NO 65
<211> LENGTH: 54
<212> TYPE: DNA
<213> ORGANISM: Artificial Sequence
<220> FEATURE:
<223> OTHER INFORMATION: synthetic

<400> SEQUENCE: 65
gtctcgtggg ctcggagatg tgtataagag acagtttctc actcgctctt tctc        54

<210> SEQ ID NO 66
<211> LENGTH: 53
<212> TYPE: DNA
<213> ORGANISM: Artificial Sequence
<220> FEATURE:
<223> OTHER INFORMATION: synthetic

<400> SEQUENCE: 66
tcgtcggcag cgtcagatgt gtataagaga cagcactaac gattgctgat gac         53

<210> SEQ ID NO 67
<211> LENGTH: 53
<212> TYPE: DNA
<213> ORGANISM: Artificial Sequence
<220> FEATURE:
<223> OTHER INFORMATION: synthetic

<400> SEQUENCE: 67
tcgtcggcag cgtcagatgt gtataagaga cagtttctag cttctgcctt ctc         53

<210> SEQ ID NO 68
<211> LENGTH: 20
<212> TYPE: DNA
<213> ORGANISM: Artificial Sequence
<220> FEATURE:
<223> OTHER INFORMATION: synthetic

<400> SEQUENCE: 68
tacccagctc agaaccatcc                                              20

<210> SEQ ID NO 69
<211> LENGTH: 54
<212> TYPE: DNA
<213> ORGANISM: Artificial Sequence
<220> FEATURE:
<223> OTHER INFORMATION: synthetic

<400> SEQUENCE: 69
gtctcgtggg ctcggagatg tgtataagag acagtgcttt tcagaattga tgtg        54

<210> SEQ ID NO 70
<211> LENGTH: 54
<212> TYPE: DNA
<213> ORGANISM: Artificial Sequence
<220> FEATURE:
<223> OTHER INFORMATION: synthetic

<400> SEQUENCE: 70
tcgtcggcag cgtcagatgt gtataagaga cagatttcta gcttctgcct tctc        54

<210> SEQ ID NO 71
<211> LENGTH: 53
<212> TYPE: DNA
<213> ORGANISM: Artificial Sequence
<220> FEATURE:
<223> OTHER INFORMATION: synthetic

<400> SEQUENCE: 71
tcgtcggcag cgtcagatgt gtataagaga cagtgtagtt cagggctgtt agg         53

<210> SEQ ID NO 72
<211> LENGTH: 20
<212> TYPE: DNA

<213> ORGANISM: Artificial Sequence
<220> FEATURE:
<223> OTHER INFORMATION: synthetic

<400> SEQUENCE: 72
cactcactta agtaccatcc                                              20

<210> SEQ ID NO 73
<211> LENGTH: 55
<212> TYPE: DNA
<213> ORGANISM: Artificial Sequence
<220> FEATURE:
<223> OTHER INFORMATION: synthetic

<400> SEQUENCE: 73
gtctcgtggg ctcggagatg tgtataagag acagtttcaa aactaaccaa tctgc       55

<210> SEQ ID NO 74
<211> LENGTH: 53
<212> TYPE: DNA
<213> ORGANISM: Artificial Sequence
<220> FEATURE:
<223> OTHER INFORMATION: synthetic

<400> SEQUENCE: 74
tcgtcggcag cgtcagatgt gtataagaga caggctgtta gggagactga gaa         53

<210> SEQ ID NO 75
<211> LENGTH: 51
<212> TYPE: DNA
<213> ORGANISM: Artificial Sequence
<220> FEATURE:
<223> OTHER INFORMATION: synthetic

<400> SEQUENCE: 75
tcgtcggcag cgtcagatgt gtataagaga caggtgagga ggcatccgag t           51

<210> SEQ ID NO 76
<211> LENGTH: 20
<212> TYPE: DNA
<213> ORGANISM: Artificial Sequence
<220> FEATURE:
<223> OTHER INFORMATION: synthetic

<400> SEQUENCE: 76
cacaaacctg agaaccatcg                                              20

<210> SEQ ID NO 77
<211> LENGTH: 57
<212> TYPE: DNA
<213> ORGANISM: Artificial Sequence
<220> FEATURE:
<223> OTHER INFORMATION: synthetic

<400> SEQUENCE: 77
gtctcgtggg ctcggagatg tgtataagag acaggcaaat taaagaatct ctgaaaa     57

<210> SEQ ID NO 78
<211> LENGTH: 51
<212> TYPE: DNA
<213> ORGANISM: Artificial Sequence
<220> FEATURE:
<223> OTHER INFORMATION: synthetic

<400> SEQUENCE: 78
tcgtcggcag cgtcagatgt gtataagaga caggaaggag ggggtgagga g           51

<210> SEQ ID NO 79
<211> LENGTH: 56
<212> TYPE: DNA
<213> ORGANISM: Artificial Sequence
<220> FEATURE:
<223> OTHER INFORMATION: synthetic

<400> SEQUENCE: 79
gtctcgtggg ctcggagatg tgtataagag acagaaagta aagcatttct gaatcc    56

<210> SEQ ID NO 80
<211> LENGTH: 53
<212> TYPE: DNA
<213> ORGANISM: Artificial Sequence
<220> FEATURE:
<223> OTHER INFORMATION: synthetic

<400> SEQUENCE: 80
tcgtcggcag cgtcagatgt gtataagaga cagaccctgc acagaaccta taa    53

<210> SEQ ID NO 81
<211> LENGTH: 20
<212> TYPE: DNA
<213> ORGANISM: Artificial Sequence
<220> FEATURE:
<223> OTHER INFORMATION: synthetic

<400> SEQUENCE: 81
cacctccatt tgaaccatcc    20

<210> SEQ ID NO 82
<211> LENGTH: 54
<212> TYPE: DNA
<213> ORGANISM: Artificial Sequence
<220> FEATURE:
<223> OTHER INFORMATION: synthetic

<400> SEQUENCE: 82
gtctcgtggg ctcggagatg tgtataagag acagaaggac ttggcttgtc ttct    54

<210> SEQ ID NO 83
<211> LENGTH: 54
<212> TYPE: DNA
<213> ORGANISM: Artificial Sequence
<220> FEATURE:
<223> OTHER INFORMATION: synthetic

<400> SEQUENCE: 83
gtctcgtggg ctcggagatg tgtataagag acaggacttg gcttgtcttc tgat    54

<210> SEQ ID NO 84
<211> LENGTH: 53
<212> TYPE: DNA
<213> ORGANISM: Artificial Sequence
<220> FEATURE:
<223> OTHER INFORMATION: synthetic

<400> SEQUENCE: 84
tcgtcggcag cgtcagatgt gtataagaga cagcctattt catattgggt gga    53

<210> SEQ ID NO 85
<211> LENGTH: 20
<212> TYPE: DNA
<213> ORGANISM: Artificial Sequence
<220> FEATURE:

<223> OTHER INFORMATION: synthetic

<400> SEQUENCE: 85
cacccaccta agcaccatct                                      20

<210> SEQ ID NO 86
<211> LENGTH: 54
<212> TYPE: DNA
<213> ORGANISM: Artificial Sequence
<220> FEATURE:
<223> OTHER INFORMATION: synthetic

<400> SEQUENCE: 86
gtctcgtggg ctcggagatg tgtataagag acagttcaaa acacagggaa aact       54

<210> SEQ ID NO 87
<211> LENGTH: 53
<212> TYPE: DNA
<213> ORGANISM: Artificial Sequence
<220> FEATURE:
<223> OTHER INFORMATION: synthetic

<400> SEQUENCE: 87
tcgtcggcag cgtcagatgt gtataagaga cagtttcata ttgggtggat tgt        53

<210> SEQ ID NO 88
<211> LENGTH: 52
<212> TYPE: DNA
<213> ORGANISM: Artificial Sequence
<220> FEATURE:
<223> OTHER INFORMATION: syntheti

<400> SEQUENCE: 88
tcgtcggcag cgtcagatgt gtataagaga caggcagcat cacctgtgta ac         52

<210> SEQ ID NO 89
<211> LENGTH: 20
<212> TYPE: DNA
<213> ORGANISM: Artificial Sequence
<220> FEATURE:
<223> OTHER INFORMATION: synthetic

<400> SEQUENCE: 89
caccttcatc agaaccatct                                      20

<210> SEQ ID NO 90
<211> LENGTH: 55
<212> TYPE: DNA
<213> ORGANISM: Artificial Sequence
<220> FEATURE:
<223> OTHER INFORMATION: synthetic

<400> SEQUENCE: 90
gtctcgtggg ctcggagatg tgtataagag acaggaagta aaaagcagag gaagc      55

<210> SEQ ID NO 91
<211> LENGTH: 52
<212> TYPE: DNA
<213> ORGANISM: Artificial Sequence
<220> FEATURE:
<223> OTHER INFORMATION: synthetic

<400> SEQUENCE: 91
tcgtcggcag cgtcagatgt gtataagaga cagagcagca tcacctgtgt aa         52

```
<210> SEQ ID NO 92
<211> LENGTH: 57
<212> TYPE: DNA
<213> ORGANISM: Artificial Sequence
<220> FEATURE:
<223> OTHER INFORMATION: synthetic

<400> SEQUENCE: 92
tcgtcggcag cgtcagatgt gtataagaga cagtacatgt tttctatatg aggcatt        57

<210> SEQ ID NO 93
<211> LENGTH: 20
<212> TYPE: DNA
<213> ORGANISM: Artificial Sequence
<220> FEATURE:
<223> OTHER INFORMATION: synthetic

<400> SEQUENCE: 93
cagctatctc agaaccttcc                                                  20

<210> SEQ ID NO 94
<211> LENGTH: 56
<212> TYPE: DNA
<213> ORGANISM: Artificial Sequence
<220> FEATURE:
<223> OTHER INFORMATION: synthetic

<400> SEQUENCE: 94
gtctcgtggg ctcggagatg tgtataagag acagcttcct ctaagtctca gctcat         56

<210> SEQ ID NO 95
<211> LENGTH: 58
<212> TYPE: DNA
<213> ORGANISM: Artificial Sequence
<220> FEATURE:
<223> OTHER INFORMATION: synthetic

<400> SEQUENCE: 95
tcgtcggcag cgtcagatgt gtataagaga cagttttcta tttttccata cttttag        58

<210> SEQ ID NO 96
<211> LENGTH: 54
<212> TYPE: DNA
<213> ORGANISM: Artificial Sequence
<220> FEATURE:
<223> OTHER INFORMATION: synthetic

<400> SEQUENCE: 96
gtctcgtggg ctcggagatg tgtataagag acagagcctt tcagattagt cagg           54

<210> SEQ ID NO 97
<211> LENGTH: 53
<212> TYPE: DNA
<213> ORGANISM: Artificial Sequence
<220> FEATURE:
<223> OTHER INFORMATION: synthetic

<400> SEQUENCE: 97
tcgtcggcag cgtcagatgt gtataagaga cagtctcaga gcttaggatg cac            53

<210> SEQ ID NO 98
<211> LENGTH: 20
<212> TYPE: DNA
<213> ORGANISM: Artificial Sequence
<220> FEATURE:
<223> OTHER INFORMATION: synthetic
```

<400> SEQUENCE: 98
ttcgtatctg taaaaccaag                                          20

<210> SEQ ID NO 99
<211> LENGTH: 56
<212> TYPE: DNA
<213> ORGANISM: Artificial Sequence
<220> FEATURE:
<223> OTHER INFORMATION: synthetic

<400> SEQUENCE: 99
gtctcgtggg ctcggagatg tgtataagag acagtcttga aacacaatac tgttgg    56

<210> SEQ ID NO 100
<211> LENGTH: 55
<212> TYPE: DNA
<213> ORGANISM: Artificial Sequence
<220> FEATURE:
<223> OTHER INFORMATION: synthetic

<400> SEQUENCE: 100
gtctcgtggg ctcggagatg tgtataagag acagcttgaa acacaatact gttgg     55

<210> SEQ ID NO 101
<211> LENGTH: 54
<212> TYPE: DNA
<213> ORGANISM: Artificial Sequence
<220> FEATURE:
<223> OTHER INFORMATION: synthetic

<400> SEQUENCE: 101
tcgtcggcag cgtcagatgt gtataagaga cagacataca ttgccttact ttgc      54

<210> SEQ ID NO 102
<211> LENGTH: 53
<212> TYPE: DNA
<213> ORGANISM: Artificial Sequence
<220> FEATURE:
<223> OTHER INFORMATION: synthetic

<400> SEQUENCE: 102
gtctcgtggg ctcggagatg tgtataagag acagtttttg actgccagaa ggt       53

<210> SEQ ID NO 103
<211> LENGTH: 56
<212> TYPE: DNA
<213> ORGANISM: Artificial Sequence
<220> FEATURE:
<223> OTHER INFORMATION: synthetic

<400> SEQUENCE: 103
gtctcgtggg ctcggagatg tgtataagag acagggaagc aaaagttat acatga     56

<210> SEQ ID NO 104
<211> LENGTH: 54
<212> TYPE: DNA
<213> ORGANISM: Artificial Sequence
<220> FEATURE:
<223> OTHER INFORMATION: synthetic

<400> SEQUENCE: 104
tcgtcggcag cgtcagatgt gtataagaga cagagtttgg catcttcttt acct      54

<210> SEQ ID NO 105
<211> LENGTH: 20

```
<212> TYPE: DNA
<213> ORGANISM: Artificial Sequence
<220> FEATURE:
<223> OTHER INFORMATION: synthetic

<400> SEQUENCE: 105
tgagcatctg taaaaccaag                                            20

<210> SEQ ID NO 106
<211> LENGTH: 52
<212> TYPE: DNA
<213> ORGANISM: Artificial Sequence
<220> FEATURE:
<223> OTHER INFORMATION: synthetic

<400> SEQUENCE: 106
gtctcgtggg ctcggagatg tgtataagag acagagtggg gcttctcatc ac        52

<210> SEQ ID NO 107
<211> LENGTH: 54
<212> TYPE: DNA
<213> ORGANISM: Artificial Sequence
<220> FEATURE:
<223> OTHER INFORMATION: synthetic

<400> SEQUENCE: 107
tcgtcggcag cgtcagatgt gtataagaga cagaagtttg gcatcttctt tacc      54

<210> SEQ ID NO 108
<211> LENGTH: 53
<212> TYPE: DNA
<213> ORGANISM: Artificial Sequence
<220> FEATURE:
<223> OTHER INFORMATION: synthetic

<400> SEQUENCE: 108
tcgtcggcag cgtcagatgt gtataagaga cagaatgata gatcccagct gaa       53

<210> SEQ ID NO 109
<211> LENGTH: 20
<212> TYPE: DNA
<213> ORGANISM: Artificial Sequence
<220> FEATURE:
<223> OTHER INFORMATION: synthetic

<400> SEQUENCE: 109
ttctaatctc taaaaccaag                                            20

<210> SEQ ID NO 110
<211> LENGTH: 54
<212> TYPE: DNA
<213> ORGANISM: Artificial Sequence
<220> FEATURE:
<223> OTHER INFORMATION: synthetic

<400> SEQUENCE: 110
gtctcgtggg ctcggagatg tgtataagag acagctttcc tccttgcatg tatt      54

<210> SEQ ID NO 111
<211> LENGTH: 53
<212> TYPE: DNA
<213> ORGANISM: Artificial Sequence
<220> FEATURE:
<223> OTHER INFORMATION: synthetic

<400> SEQUENCE: 111
```
tcgtcggcag cgtcagatgt gtataagaga cagggagcca cagattaaat gat    53

<210> SEQ ID NO 112
<211> LENGTH: 54
<212> TYPE: DNA
<213> ORGANISM: Artificial Sequence
<220> FEATURE:
<223> OTHER INFORMATION: synthetic

<400> SEQUENCE: 112
gtctcgtggg ctcggagatg tgtataagag acagtctttc ctccttgcat gtat    54

<210> SEQ ID NO 113
<211> LENGTH: 53
<212> TYPE: DNA
<213> ORGANISM: Artificial Sequence
<220> FEATURE:
<223> OTHER INFORMATION: synthetic

<400> SEQUENCE: 113
tcgtcggcag cgtcagatgt gtataagaga cagtcatgaa tggtgactca gaa    53

<210> SEQ ID NO 114
<211> LENGTH: 20
<212> TYPE: DNA
<213> ORGANISM: Artificial Sequence
<220> FEATURE:
<223> OTHER INFORMATION: synthetic

<400> SEQUENCE: 114
gtggtatctg caaaaccaag    20

<210> SEQ ID NO 115
<211> LENGTH: 52
<212> TYPE: DNA
<213> ORGANISM: Artificial Sequence
<220> FEATURE:
<223> OTHER INFORMATION: synthetic

<400> SEQUENCE: 115
gtctcgtggg ctcggagatg tgtataagag acagaaatgc cagccacttt tt    52

<210> SEQ ID NO 116
<211> LENGTH: 54
<212> TYPE: DNA
<213> ORGANISM: Artificial Sequence
<220> FEATURE:
<223> OTHER INFORMATION: synthetic

<400> SEQUENCE: 116
tcgtcggcag cgtcagatgt gtataagaga cagaaatcat gaatggtgac tcag    54

<210> SEQ ID NO 117
<211> LENGTH: 53
<212> TYPE: DNA
<213> ORGANISM: Artificial Sequence
<220> FEATURE:
<223> OTHER INFORMATION: synthetic

<400> SEQUENCE: 117
tcgtcggcag cgtcagatgt gtataagaga caggccaaac catattagca aac    53

<210> SEQ ID NO 118
<211> LENGTH: 20
<212> TYPE: DNA
<213> ORGANISM: Artificial Sequence -continued

```
<220> FEATURE:
<223> OTHER INFORMATION: synthetic

<400> SEQUENCE: 118
tcctcatgtg taaaaccaag                                              20

<210> SEQ ID NO 119
<211> LENGTH: 54
<212> TYPE: DNA
<213> ORGANISM: Artificial Sequence
<220> FEATURE:
<223> OTHER INFORMATION: synthetic

<400> SEQUENCE: 119
gtctcgtggg ctcggagatg tgtataagag acagttgagt tcatgagaat cgtg        54

<210> SEQ ID NO 120
<211> LENGTH: 55
<212> TYPE: DNA
<213> ORGANISM: Artificial Sequence
<220> FEATURE:
<223> OTHER INFORMATION: synthetic

<400> SEQUENCE: 120
gtctcgtggg ctcggagatg tgtataagag acagattgag ttcatgagaa tcgtg       55

<210> SEQ ID NO 121
<211> LENGTH: 53
<212> TYPE: DNA
<213> ORGANISM: Artificial Sequence
<220> FEATURE:
<223> OTHER INFORMATION: synthetic

<400> SEQUENCE: 121
tcgtcggcag cgtcagatgt gtataagaga caggcaaacg tacactgtaa tgc         53

<210> SEQ ID NO 122
<211> LENGTH: 20
<212> TYPE: DNA
<213> ORGANISM: Artificial Sequence
<220> FEATURE:
<223> OTHER INFORMATION: synthetic

<400> SEQUENCE: 122
tctgcatctt taaaaccaag                                              20

<210> SEQ ID NO 123
<211> LENGTH: 54
<212> TYPE: DNA
<213> ORGANISM: Artificial Sequence
<220> FEATURE:
<223> OTHER INFORMATION: synthetic

<400> SEQUENCE: 123
gtctcgtggg ctcggagatg tgtataagag acaggctttg ctgagaccat agat        54

<210> SEQ ID NO 124
<211> LENGTH: 54
<212> TYPE: DNA
<213> ORGANISM: Artificial Sequence
<220> FEATURE:
<223> OTHER INFORMATION: synthetic

<400> SEQUENCE: 124
gtctcgtggg ctcggagatg tgtataagag acagatgctt tgctgagacc atag        54
```

<210> SEQ ID NO 125
<211> LENGTH: 53
<212> TYPE: DNA
<213> ORGANISM: Artificial Sequence
<220> FEATURE:
<223> OTHER INFORMATION: synthetic

<400> SEQUENCE: 125
tcgtcggcag cgtcagatgt gtataagaga cagcaaagtg ctgggattac aga        53

<210> SEQ ID NO 126
<211> LENGTH: 20
<212> TYPE: DNA
<213> ORGANISM: Artificial Sequence
<220> FEATURE:
<223> OTHER INFORMATION: synthetic

<400> SEQUENCE: 126
tttgtatctt taaaaccatg        20

<210> SEQ ID NO 127
<211> LENGTH: 59
<212> TYPE: DNA
<213> ORGANISM: Artificial Sequence
<220> FEATURE:
<223> OTHER INFORMATION: synthetic

<400> SEQUENCE: 127
gtctcgtggg ctcggagatg tgtataagag acagtgcaaa gttttatgta gtttaagtg    59

<210> SEQ ID NO 128
<211> LENGTH: 58
<212> TYPE: DNA
<213> ORGANISM: Artificial Sequence
<220> FEATURE:
<223> OTHER INFORMATION: synthetic

<400> SEQUENCE: 128
gtctcgtggg ctcggagatg tgtataagag acagaatttg caaagttttta tgtagttt    58

<210> SEQ ID NO 129
<211> LENGTH: 53
<212> TYPE: DNA
<213> ORGANISM: Artificial Sequence
<220> FEATURE:
<223> OTHER INFORMATION: synthetic

<400> SEQUENCE: 129
tcgtcggcag cgtcagatgt gtataagaga cagtgggact cttggttctg tat          53

<210> SEQ ID NO 130
<211> LENGTH: 20
<212> TYPE: DNA
<213> ORGANISM: Artificial Sequence
<220> FEATURE:
<223> OTHER INFORMATION: synthetic

<400> SEQUENCE: 130
ttcttatgtg tgaaaccaag        20

<210> SEQ ID NO 131
<211> LENGTH: 57
<212> TYPE: DNA
<213> ORGANISM: Artificial Sequence
<220> FEATURE:
<223> OTHER INFORMATION: synthetic

```
<400> SEQUENCE: 131
gtctcgtggg ctcggagatg tgtataagag acagttttg ttgttgtttt acttgaa         57

<210> SEQ ID NO 132
<211> LENGTH: 53
<212> TYPE: DNA
<213> ORGANISM: Artificial Sequence
<220> FEATURE:
<223> OTHER INFORMATION: synthetic

<400> SEQUENCE: 132
tcgtcggcag cgtcagatgt gtataagaga cagttgggac tcttggttct gta            53

<210> SEQ ID NO 133
<211> LENGTH: 52
<212> TYPE: DNA
<213> ORGANISM: Artificial Sequence
<220> FEATURE:
<223> OTHER INFORMATION: synthetic

<400> SEQUENCE: 133
tcgtcggcag cgtcagatgt gtataagaga cagaaattct tcttgggctc ag             52

<210> SEQ ID NO 134
<211> LENGTH: 20
<212> TYPE: DNA
<213> ORGANISM: Artificial Sequence
<220> FEATURE:
<223> OTHER INFORMATION: synthetic

<400> SEQUENCE: 134
ctctcttctg taaaaccaag                                                 20

<210> SEQ ID NO 135
<211> LENGTH: 54
<212> TYPE: DNA
<213> ORGANISM: Artificial Sequence
<220> FEATURE:
<223> OTHER INFORMATION: synthetic

<400> SEQUENCE: 135
gtctcgtggg ctcggagatg tgtataagag acaggctcat tactgggtta agca           54

<210> SEQ ID NO 136
<211> LENGTH: 53
<212> TYPE: DNA
<213> ORGANISM: Artificial Sequence
<220> FEATURE:
<223> OTHER INFORMATION: synthetic

<400> SEQUENCE: 136
tcgtcggcag cgtcagatgt gtataagaga caggaaattc ttcttgggct cag            53

<210> SEQ ID NO 137
<211> LENGTH: 53
<212> TYPE: DNA
<213> ORGANISM: Artificial Sequence
<220> FEATURE:
<223> OTHER INFORMATION: synthetic

<400> SEQUENCE: 137
tcgtcggcag cgtcagatgt gtataagaga cagtctaggc tcttgacacc atc            53

<210> SEQ ID NO 138
```

```
<211> LENGTH: 20
<212> TYPE: DNA
<213> ORGANISM: Artificial Sequence
<220> FEATURE:
<223> OTHER INFORMATION: synthetic

<400> SEQUENCE: 138
tgggtttctt taaaaccaag                                              20

<210> SEQ ID NO 139
<211> LENGTH: 55
<212> TYPE: DNA
<213> ORGANISM: Artificial Sequence
<220> FEATURE:
<223> OTHER INFORMATION: synthetic

<400> SEQUENCE: 139
gtctcgtggg ctcggagatg tgtataagag acaggaacaa ctagacccaa tgtga       55

<210> SEQ ID NO 140
<211> LENGTH: 53
<212> TYPE: DNA
<213> ORGANISM: Artificial Sequence
<220> FEATURE:
<223> OTHER INFORMATION: synthetic

<400> SEQUENCE: 140
tcgtcggcag cgtcagatgt gtataagaga caggtctagg ctcttgacac cat         53

<210> SEQ ID NO 141
<211> LENGTH: 29
<212> TYPE: DNA
<213> ORGANISM: Artificial Sequence
<220> FEATURE:
<223> OTHER INFORMATION: synthetic

<400> SEQUENCE: 141
ggtttcatcc atccgacatt gaagttgac                                    29

<210> SEQ ID NO 142
<211> LENGTH: 28
<212> TYPE: DNA
<213> ORGANISM: Artificial Sequence
<220> FEATURE:
<223> OTHER INFORMATION: synthetic

<400> SEQUENCE: 142
gaccagtcct tgctgaaaga caagtctg                                     28

<210> SEQ ID NO 143
<211> LENGTH: 29
<212> TYPE: DNA
<213> ORGANISM: Artificial Sequence
<220> FEATURE:
<223> OTHER INFORMATION: synthetic

<400> SEQUENCE: 143
gggtgaattc agtgtagtac aagagatag                                    29

<210> SEQ ID NO 144
<211> LENGTH: 18
<212> TYPE: DNA
<213> ORGANISM: Artificial Sequence
<220> FEATURE:
<223> OTHER INFORMATION: synthetic

<400> SEQUENCE: 144
```
ggcatgcaga tcccacag                                                      18

<210> SEQ ID NO 145
<211> LENGTH: 22
<212> TYPE: DNA
<213> ORGANISM: Artificial Sequence
<220> FEATURE:
<223> OTHER INFORMATION: synthetic

<400> SEQUENCE: 145
aagtcacgga gcgagagagc ac                                                 22

<210> SEQ ID NO 146
<211> LENGTH: 19
<212> TYPE: DNA
<213> ORGANISM: Artificial Sequence
<220> FEATURE:
<223> OTHER INFORMATION: synthetic

<400> SEQUENCE: 146
ggccaccaag gagaacttg                                                     19

<210> SEQ ID NO 147
<211> LENGTH: 32
<212> TYPE: DNA
<213> ORGANISM: Artificial Sequence
<220> FEATURE:
<223> OTHER INFORMATION: synthetic

<400> SEQUENCE: 147
cctgtcagtg attgggttcc gaatcctcct cc                                      32

<210> SEQ ID NO 148
<211> LENGTH: 24
<212> TYPE: DNA
<213> ORGANISM: Artificial Sequence
<220> FEATURE:
<223> OTHER INFORMATION: synthetic

<400> SEQUENCE: 148
catgagcaga ttaaacccgg ccac                                               24

<210> SEQ ID NO 149
<211> LENGTH: 22
<212> TYPE: DNA
<213> ORGANISM: Artificial Sequence
<220> FEATURE:
<223> OTHER INFORMATION: synthetic

<400> SEQUENCE: 149
atgtctcgct ccgtggcctt ag                                                 22

<210> SEQ ID NO 150
<211> LENGTH: 19
<212> TYPE: DNA
<213> ORGANISM: Artificial Sequence
<220> FEATURE:
<223> OTHER INFORMATION: synthetic

<400> SEQUENCE: 150
gggcattcct gaagctgac                                                     19

<210> SEQ ID NO 151
<211> LENGTH: 22
<212> TYPE: DNA

```
<213> ORGANISM: Artificial Sequence
<220> FEATURE:
<223> OTHER INFORMATION: synthetic

<400> SEQUENCE: 151
ccttagctgt gctcgcgcta ct                                          22

<210> SEQ ID NO 152
<211> LENGTH: 18
<212> TYPE: DNA
<213> ORGANISM: Artificial Sequence
<220> FEATURE:
<223> OTHER INFORMATION: synthetic

<400> SEQUENCE: 152
agggactgag ggtggaag                                               18

<210> SEQ ID NO 153
<211> LENGTH: 17
<212> TYPE: DNA
<213> ORGANISM: Artificial Sequence
<220> FEATURE:
<223> OTHER INFORMATION: synthetic

<400> SEQUENCE: 153
cagcctgctc tgccttg                                                17

<210> SEQ ID NO 154
<211> LENGTH: 23
<212> TYPE: DNA
<213> ORGANISM: Artificial Sequence
<220> FEATURE:
<223> OTHER INFORMATION: synthetic

<400> SEQUENCE: 154
catgcaagcc cataaccgct gtg                                         23

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
aagtcacgga gcgagaga                                               18

<210> SEQ ID NO 156
<211> LENGTH: 23
<212> TYPE: DNA
<213> ORGANISM: Artificial Sequence
<220> FEATURE:
<223> OTHER INFORMATION: synthetic

<400> SEQUENCE: 156
gttggctaag aatctgagaa ggg                                         23

<210> SEQ ID NO 157
<211> LENGTH: 18
<212> TYPE: DNA
<213> ORGANISM: Artificial Sequence
<220> FEATURE:
<223> OTHER INFORMATION: synthetic

<400> SEQUENCE: 157
ggcatgcaga tcccacag                                               18
```

<210> SEQ ID NO 158
<211> LENGTH: 21
<212> TYPE: DNA
<213> ORGANISM: Artificial Sequence
<220> FEATURE:
<223> OTHER INFORMATION: synthetic

<400> SEQUENCE: 158
tctgggcggt gctacaactg g                                     21

<210> SEQ ID NO 159
<211> LENGTH: 24
<212> TYPE: DNA
<213> ORGANISM: Artificial Sequence
<220> FEATURE:
<223> OTHER INFORMATION: synthetic

<400> SEQUENCE: 159
agagagagag acgcatggtc aacc                                  24

<210> SEQ ID NO 160
<211> LENGTH: 24
<212> TYPE: DNA
<213> ORGANISM: Artificial Sequence
<220> FEATURE:
<223> OTHER INFORMATION: synthetic

<400> SEQUENCE: 160
ccactgtttt acttctagcc agtc                                  24

<210> SEQ ID NO 161
<211> LENGTH: 22
<212> TYPE: DNA
<213> ORGANISM: Artificial Sequence
<220> FEATURE:
<223> OTHER INFORMATION: synthetic

<400> SEQUENCE: 161
cagggactga gggtggaagg tc                                    22

<210> SEQ ID NO 162
<211> LENGTH: 22
<212> TYPE: DNA
<213> ORGANISM: Artificial Sequence
<220> FEATURE:
<223> OTHER INFORMATION: synthetic

<400> SEQUENCE: 162
cagggactga gagtgaaagg tc                                    22

<210> SEQ ID NO 163
<211> LENGTH: 20
<212> TYPE: DNA
<213> ORGANISM: Artificial Sequence
<220> FEATURE:
<223> OTHER INFORMATION: synthetic

<400> SEQUENCE: 163
ttgacactgc caaacctatt                                       20

<210> SEQ ID NO 164
<211> LENGTH: 20
<212> TYPE: DNA
<213> ORGANISM: Artificial Sequence
<220> FEATURE:

<223> OTHER INFORMATION: synthetic

<400> SEQUENCE: 164
tgacactgcc aaacctatta                                               20

<210> SEQ ID NO 165
<211> LENGTH: 20
<212> TYPE: DNA
<213> ORGANISM: Artificial Sequence
<220> FEATURE:
<223> OTHER INFORMATION: synthetic

<400> SEQUENCE: 165
acactgccaa acctattagg                                               20

<210> SEQ ID NO 166
<211> LENGTH: 20
<212> TYPE: DNA
<213> ORGANISM: Artificial Sequence
<220> FEATURE:
<223> OTHER INFORMATION: synthetic

<400> SEQUENCE: 166
ccccaccatt cctaccactt                                               20

<210> SEQ ID NO 167
<211> LENGTH: 20
<212> TYPE: DNA
<213> ORGANISM: Artificial Sequence
<220> FEATURE:
<223> OTHER INFORMATION: synthetic

<400> SEQUENCE: 167
tgcttgtaga gaggcctgag                                               20

<210> SEQ ID NO 168
<211> LENGTH: 20
<212> TYPE: DNA
<213> ORGANISM: Artificial Sequence
<220> FEATURE:
<223> OTHER INFORMATION: synthetic

<400> SEQUENCE: 168
gagtccgagc agaagaagaa                                               20

<210> SEQ ID NO 169
<211> LENGTH: 13
<212> TYPE: PRT
<213> ORGANISM: Artificial Sequence
<220> FEATURE:
<223> OTHER INFORMATION: synthetic

<400> SEQUENCE: 169

Ile Thr Gln Gly Leu Ala Val Ser Thr Ile Ser Ser Phe
1               5                   10

<210> SEQ ID NO 170
<211> LENGTH: 22
<212> TYPE: DNA
<213> ORGANISM: Artificial Sequence
<220> FEATURE:
<223> OTHER INFORMATION: synthetic

<400> SEQUENCE: 170
aataggtttg gcagtgtcaa cc                                            22

<210> SEQ ID NO 171
<211> LENGTH: 20
<212> TYPE: DNA
<213> ORGANISM: Artificial Sequence
<220> FEATURE:
<223> OTHER INFORMATION: synthetic

<400> SEQUENCE: 171
cagcagcgtg tttcttgcca                                               20

<210> SEQ ID NO 172
<211> LENGTH: 20
<212> TYPE: DNA
<213> ORGANISM: Artificial Sequence
<220> FEATURE:
<223> OTHER INFORMATION: synthetic

<400> SEQUENCE: 172
ttgggatctt taaaaccaag                                               20

<210> SEQ ID NO 173
<211> LENGTH: 23
<212> TYPE: DNA
<213> ORGANISM: Artificial Sequence
<220> FEATURE:
<223> OTHER INFORMATION: synthetic

<400> SEQUENCE: 173
gagtggtaag aaacacgctg ctg                                           23

<210> SEQ ID NO 174
<211> LENGTH: 20
<212> TYPE: DNA
<213> ORGANISM: Artificial Sequence
<220> FEATURE:
<223> OTHER INFORMATION: synthetic

<400> SEQUENCE: 174
gaggaaatgc cctcttctgt                                               20

<210> SEQ ID NO 175
<211> LENGTH: 20
<212> TYPE: DNA
<213> ORGANISM: Artificial Sequence
<220> FEATURE:
<223> OTHER INFORMATION: synthetic

<400> SEQUENCE: 175
ttgaccagtg agccagtaaa                                               20

<210> SEQ ID NO 176
<211> LENGTH: 18
<212> TYPE: DNA
<213> ORGANISM: Artificial Sequence
<220> FEATURE:
<223> OTHER INFORMATION: synthetic

<400> SEQUENCE: 176
ctgccaggga ctgagagt                                                 18

<210> SEQ ID NO 177
<211> LENGTH: 18
<212> TYPE: DNA
<213> ORGANISM: Artificial Sequence
<220> FEATURE:
<223> OTHER INFORMATION: synthetic

```
<400> SEQUENCE: 177
gtggatgtgg aggaagag                                                      18

<210> SEQ ID NO 178
<211> LENGTH: 20
<212> TYPE: DNA
<213> ORGANISM: Artificial Sequence
<220> FEATURE:
<223> OTHER INFORMATION: synthetic

<400> SEQUENCE: 178
ggagcagctg gtcagagggg                                                    20

<210> SEQ ID NO 179
<211> LENGTH: 20
<212> TYPE: DNA
<213> ORGANISM: Artificial Sequence
<220> FEATURE:
<223> OTHER INFORMATION: synthetic

<400> SEQUENCE: 179
gggaaggggg acactgggga                                                    20
```

LYMPHOHEMATOPOIETIC ENGINEERING USING CAS9 BASE EDITORS

CROSS-REFERENCE TO RELATED APPLICATIONS

This application represents the U.S. National Stage of International Application No. PCT/US2019/022049, filed Mar. 13, 2019 which claims priority to from the U.S. Provisional Patent Application No. 62/642,151, filed on Mar. 13, 2018, the disclosures of which is incorporated by reference herein in their entirety for all purposes.

BACKGROUND

The precise modulation of primary human cells has multiple applications in the fields of immunotherapy, autoimmunity and enzymopathy. Modulation of patient immune cells at the genetic level is an attractive route for therapy due to the permanency of treatment and the low risk of rejection by the patient. One approach for the gene editing of immune cells is to use Clustered Regularly Interspaced Short Palindromic Repeat (CRISPR) systems to induce a double stranded break (DSB) within a gene of interest, thereby resulting in the formation of small insertions or deletions (collectively referred to as 'indels') created by highly variable repair via the Non-Homologous End Joining (NHEJ) pathway. Alternatively, precise genome alterations can be achieved by introduction of a DSB along with co-delivery of a DNA template for repair via homology directed repair (HDR). While this approach is efficient and reliable when simply disrupting a single gene by NHEJ, precision alteration of single nucleotides by HDR is far less efficient. Furthermore, inducing multiple DSBs during multiplexed gene editing procedures can cause undesirable genotoxicity and the formation of potentially oncogenic gross chromosomal translocations. Accordingly, there remains a need in the field for more controlled and safer methods of multiplexed genetic engineering of human immune cells with limited induction of toxic DSBs.

SUMMARY OF THE DISCLOSURE

In a first aspect, provided herein is a method for producing a genetically engineered lymphohematopoietic cell. The method can comprise or consist essentially of (a) introducing into a lymphohematopoietic cell: (i) a plasmid, mRNA, or protein encoding a base editor fusion protein comprising a deaminase domain fused to a Cas9 nickase domain, wherein the nickase domain comprises a base excision repair inhibitor domain; and (ii) one or more splice acceptor-splice donor (SA-SD) gRNAs having complementarity to a target nucleic acid sequence to be genetically modified; and (b) culturing the introduced cell under conditions that promote disruption of splice sites targeted by the one or more SA-SD gRNAs, whereby the target nucleic acid sequence is modified by the base editor fusion protein and the one or more splice acceptor-splice donor (SA-SD) gRNAs relative to an untransfected lymphohematopoietic cell, and whereby a genetically engineered lymphohematopoietic cell is produced. In some cases, the method further comprises introducing into the lymphohematopoietic cell one or more gRNAs designed to produce one or more targeted knock-ins or missense mutations, whereby the genetically engineered lymphohematopoietic cell comprises at least one gene knock-out and one or more gene knock-ins or missense mutations. In some cases, the method further comprises introducing into the lymphohematopoietic cell one or more gRNAs designed to produce one or more targeted knock-ins and one or more missense mutations, whereby the genetically engineered lymphohematopoietic cell comprises at least one gene knock-out, at least one gene knock-in, and at least one missense mutation. The base editor fusion protein can be BE3, BE4, or an adenine base editor (ABE). The lymphohematopoietic cell can be a T cell, Natural Killer (NK) cell, B cell, or CD34+ hematopoietic stem progenitor cell (HSPC). The one or more SA-SD gRNAs can be chemically modified to comprise 2'-O-methyl phosphorthioate modifications on at least one 5' nucleotide and at least one 3' nucleotide of each gRNA. The base editor fusion protein and one or more splice acceptor-splice donor (SA-SD) gRNAs can exhibit about 50% to about 90% C-to-T conversion efficiency. The one or more SA-SD gRNAs can be selected from the sequences set forth in Table 1.

In another aspect, provided herein is a method for producing a genetically modified T cell. The method can comprise or consist essentially of (a) introducing into a human T cell: (i) a plasmid, mRNA, or protein encoding a base editor fusion protein comprising a deaminase domain fused to a Cas9 nickase domain, wherein the nickase domain comprises a base excision repair inhibitor domain; (ii) one or more splice acceptor-splice donor (SA-SD) gRNAs to disrupt expression of each of TRAC, B2M, and PDCD1, (iii) a donor DNA template encoding a T cell receptor (TCR) and a chimeric antigen receptor (CAR), and (iv) two gRNAs complementary to a target insertion site, (b) culturing the T cell of (a) under conditions that promote disruption of splice sites targeted by the SA-SD gRNA, whereby expression of TRAC, B2M, and PDCD1 gene products is reduced relative to an untransfected T cell; and (c) culturing the transfected T cell under conditions that promote targeted knock-in of the donor DNA template at the target insertion site. The base editor fusion protein can be BE3, BE4, or an adenine base editor (ABE). The one or more SA-SD gRNAs can be selected from the sequences set forth in Table 1. One or more of the SA-SD gRNAs and gRNAs complementary to the target insertion site can be chemically modified to comprise 2'-O-methyl phosphorthioate modifications on at least one 5' nucleotide and at least one 3' nucleotide of each gRNA. The donor DNA template can be provided as a rAAV. The TCR can specifically bind to a tumor antigen. The CAR can comprise a CAR antigen binding domain that specifically binds to a tumor antigen. The TCR and the CAR can bind to different antigens.

In a further aspect, provided herein is a genetically modified cell obtained according to the methods of this disclosure.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, where.

Figure 1:
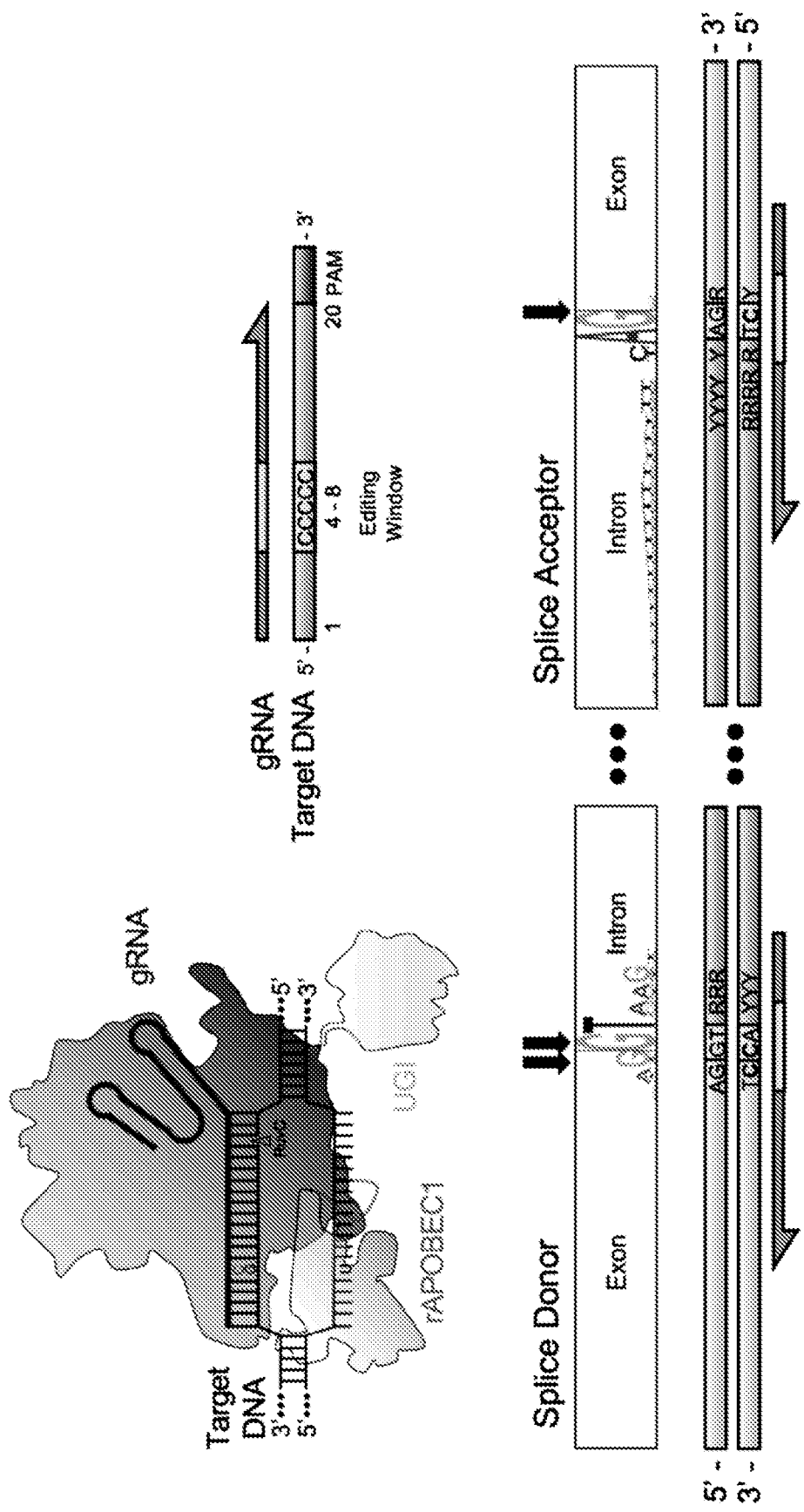
FIG. 1 presents a diagram depicting Cas9 base editor (BE) bound to target DNA (left) and protospacer depicting the base editing window achieved with BE3 and BE4 (right). Also presented are logo diagrams depicting the consensus sequence of mammalian splice donor (SD) and splice acceptor (SA) elements and the related orientation of protospacers utilized for BE knockout via splice site disruption.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods, systems, and compositions described herein are based at least in part on the inventors' development of protocols for genome engineering of primary human lymphohematopoietic cells using CRISPR-Cas9 base editors. To make point mutations without using homology directed repair (HDR), researchers have developed CRISPR base editors that fuse Cas9 nickase or dCas9 to a cytidine deaminase like APOBEC1. Unlike CRISPR, base editing does not cut double-stranded DNA but instead uses deaminase enzymes to precisely rearrange some of the atoms in one of the four bases that make up DNA or RNA, converting the base without altering the bases around it. Base editors are targeted to a specific locus by a guide RNA (gRNA), and they can convert cytidine to uridine within a small editing window near the protospacer adjacent motif (PAM) site. Uridine is subsequently converted to thymidine through base excision repair, creating a C→T change (or G→A on the opposite strand). Third-generation base editors (BE3 systems), in which base excision repair inhibitor UGI is fused to the Cas9 nickase, nick the unmodified DNA strand so that the cell is encouraged to use the edited strand as a template for mismatch repair. As a result, the cell repairs the DNA using a U-containing strand (introduced by cytidine deamination) as a template, copying the base edit. Fourth generation base editors (BE4 systems) employ two copies of base excision repair inhibitor UGI. Adenine base editors (ABEs) have been developed that efficiently convert targeted A•T base pairs to G•C (0-100% efficiency in human cells) in genomic DNA with high product purity (typically at least 99.9%) and low rates of indels (typically no more than 0.1%). See, for example, Gaudelli et al., *Nature* 551:464-471 (2017).

As described in the paragraphs and Examples that follow, the inventors' streamlined approach to genome engineering employs base editors (e.g., 3rd- and 4th-generation base editors, adenine base editor) for targeted gene disruption by knock-out and missense mutation and targeted gene knock-in in the presence of a DNA donor template. Advantages of these methods, systems, and compositions are multifold. In particular, the methods are useful for making a trio of genetic edits in a single method: targeted gene knock-out, targeted missense mutation, and targeted gene knock-in. The methods described herein are well-suited for studying lymphohematopoietic cell biology and gene function, modeling diseases such as primary immunodeficiencies, as well as correcting disease-causing point mutations, and generating novel cell products (e.g., T cell products) for therapeutic applications. Without being bound to a particular theory or mechanism of action, it is believed that use of a predetermined viral integration pattern and limited induction of toxic double-stranded breaks, the methods, systems, and compositions described herein permit safer, controllable cell engineering.

Accordingly, provided herein are methods for targeted disruption of transcription or translation of a target gene. In particular, the methods comprise targeted disruption of transcription or translation of a target gene via disruption of a start codon, introduction of a premature stop codon, and/or targeted disruption of intron/exon splice sites. In some cases, provided herein is a method comprising combining a nucleic acid sequence encoding a base editing fusion protein with guide RNAs, whereby unexpectedly high rates of base editing are obtained; especially in primary cells such CD34+ HSPCs, T cells, Natural Killer cells, and B cells. Using the methods described herein, one may knock-in and/or knock-out one or more genes of interest in primary cells with improved efficiency and a reduced rate of off-target indel formation. In preferred embodiments, the methods are used for multiplexed base editing comprising gene knock-in, gene knock-out, and missense mutation.

In a first aspect, provided herein is a method for producing a genetically engineered lymphohematopoietic cell. In particular, the method comprises transfecting base editing components into a lymphohematopoietic cell, where the components comprise (i) a plasmid encoding a base editor fusion protein comprising a deaminase domain fused to a Cas9 nickase domain and a base excision repair inhibitor domain, where the Cas9 nickase domain is optionally fused to the base excision repair domain; and (ii) one or more gRNAs having complementarity to a target nucleic acid sequence to be genetically modified. When the transfected cell is cultured under conditions that promote disruption of splice sites targeted by the one or more gRNAs, the target nucleic acid sequence is modified by the base editor fusion protein and the one or more gRNAs relative to an untransfected cell, and whereby a genetically engineered lymphohematopoietic cell is produced. As used herein, the term "lymphohematopoietic cell" refers to T cells, Natural Killer (NK) cells, B cells, CD34+ hematopoietic stem progenitor cells (HSPCs), and other cells involved in the production of lymphocytes and cells of blood, bone marrow, spleen, lymph nodes, and thymus.

As used herein, "base editors" (also known as "nucleobase editors") are Cas9 fusion proteins that comprise comprises a Cas9 nickase domain or dead Cas9 (dCas9) fused to a deaminase. In some embodiments, the fusion protein comprises a Cas9 nickase further fused to a UGI domain. In some embodiments, the UGI domain is also provided in the system but is not fused to the Cas9 domain. In some cases, the base editing fusion protein is base editor 3 (BE3) or base editor 4 (BE4), where BE3 and BE4 refer to third generation base editors and fourth generation base editors, respectively. B3 and B4 can produce C>G or A or indel mutations. In other cases, the base editing fusion protein is an adenine base editor (ABE) such as an ABE that converts A•T to G•C base pairs in DNA in bacteria and human cells. See, for example, Gaudelli et al., *Nature* 551:464-471 (2017). It will be understood that other base editors, including those that introduce null mutations at ATG "start" codons to disrupt expression of the targeted gene, are suitable for use according to the methods described herein.

In certain embodiments, the methods comprise knocking out genes by targeting splice acceptor-splice donor (SA-SD) sites or premature STOP (pmSTOP) sites. For such methods, CRISPR gRNA molecules are designed to disrupt one or more slice acceptor/donor sites within the target nucleotide sequence. A CRISPR guide RNA molecule (gRNA) comprises a sequence of at least 10 contiguous nucleotides, and often a sequence of 17-23 contiguous nucleotides, that is complementary to a target sequence in the genome of an organism and comprises a target base pair. A gRNA comprises a nucleotide sequence that is partially or wholly complementary to a gRNA target site. A gRNA target site also comprises a Protospacer Adjacent Motif (PAM) located immediately downstream from the target site. Examples of PAM sequence are known (see, e.g., Shah et al., *RNA Biology* 10 (5): 891-899, 2013).

Disruptions at SA-SD sites are particularly advantageous because one may knock out coding sequence and non-coding RNAs (ncRNAs) without stop codon read through. Exemplary SA-SD gRNAs designed toward human long non-coding RNAs and human protein coding genes relevant to immunotherapy are set forth in Table 1. As demonstrated in the Examples that follow, disruption using gRNAs targeting SA-SD sites is superior to introduction of premature STOP codons in terms of knock-out efficiency. Efficiency of base editing can be determined on the genomic level by EditR analysis of Sanger sequencing traces or by next generation sequencing (NGS), and also on the protein level by flow cytometry. Splice acceptor-splice donor base editing gRNAs that target the splice donor regions and the splice acceptor region exhibit base conversion efficiency of at least 5% and, in some cases, at least 80% or greater (e.g., 5%, 10%, 15%, 20%, 25%, 30%, 35%, 40%, 45%, 50%, 55%, 60%, 65%, 70%, 75%, 80%, 85%, 90%, 95%, 99%). In some cases, SA-SD gRNAs are significantly more efficient at C-to-T conversions than gRNAs that introduce premature stop codons disrupting.

Guide RNAs for targeting SA-SD sites can be designed using an R based program that identifies gRNAs targeting all ncRNAs and protein coding gene SA-SD sites. In some cases, the user supplies the reference genome, Ensembl transcript ID of the reference sequence, protospacer adjacent motif (PAM) site, and distance to subset upstream and downstream of exon-intron boundary. The program extracts sequences of 20 base pairs+the PAM length upstream and 15 base pairs downstream of an exon-intron boundary, as well as the splice site motif. In some embodiments, a guide molecule can be from 20 to 120 bases in length, or more. In certain embodiments, a guide molecule can be from 20 to 60 bases in length, or 20 to 50 bases, or 30 to 50 bases, or 39 to 46 bases.

In some cases, it is advantageous to use chemically modified gRNAs having increased stability when transfected into mammalian cells. For example, gRNAs can be chemically modified to comprise 2'-O-methyl phosphorthioate modifications on at least one 5' nucleotide and at least one 3' nucleotide of each gRNA. In some cases, the three terminal 5' nucleotides and three terminal 3' nucleotides are chemically modified to comprise 2'-O-methyl phosphorthioate modifications.

Figure 16:
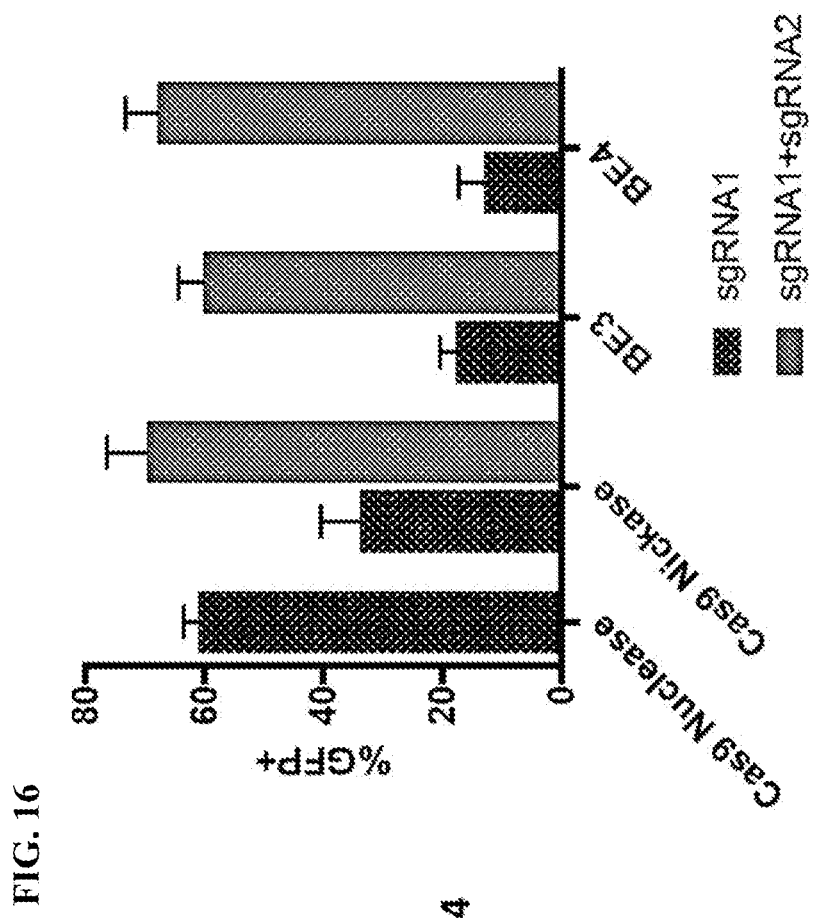
FIG. 16 illustrates targeted knock-in (KI) using BE nickase activity and efficiency relative to Cas9 nuclease and Cas9 nickase.
Figure 16:
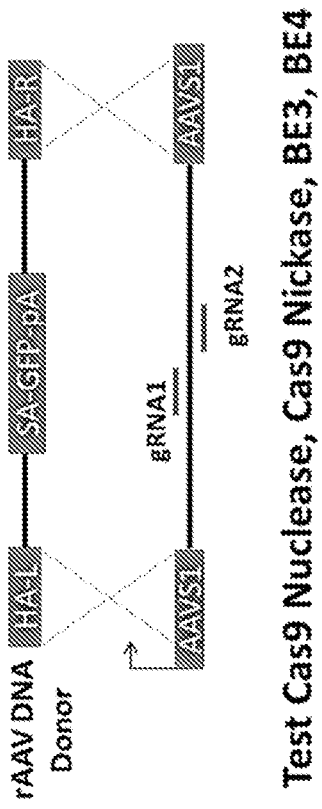

In certain embodiments, the methods employ base editing nickase activity to mediate insertion of a donor sequence by (i) homology directed repair (HDR) from a template or (ii) integration of a viral vector. For such methods, the Cas9 nickase domain facilitates targeted gene knock-in in the presence of a DNA donor template using gRNAs to target the insertion site. In some cases, the donor sequence is integrated at an endogenous safe-harbor locus such as C—C Motif Chemokine Receptor 5 (CCR5), Adeno-Associated Virus Integration Site 1 (AAVS1), ROSAβgeo26 (Rosa26), albumin (ALB), T-Cell Receptor Alpha Constant (TRAC), and/or Hypoxanthine Phosphoribosyltransferase 1 (HPRT). For example, guide RNA(s) may be designed to target the AAVS1 locus. In such cases, the guide RNAs have complementarity to the DNA target site. Referring to FIG. 16, which illustrates targeted knock-in (KI), BE nickase activity is highly effective to stimulate HDR when combined with rAAV DNA donor delivery. In some cases, BE efficiency using two guide RNAs complementary to the target insertion site was greatly improved relative to use of a single gRNA, or use of Cas9 nuclease or Cas9 nickase.

Figure 12:
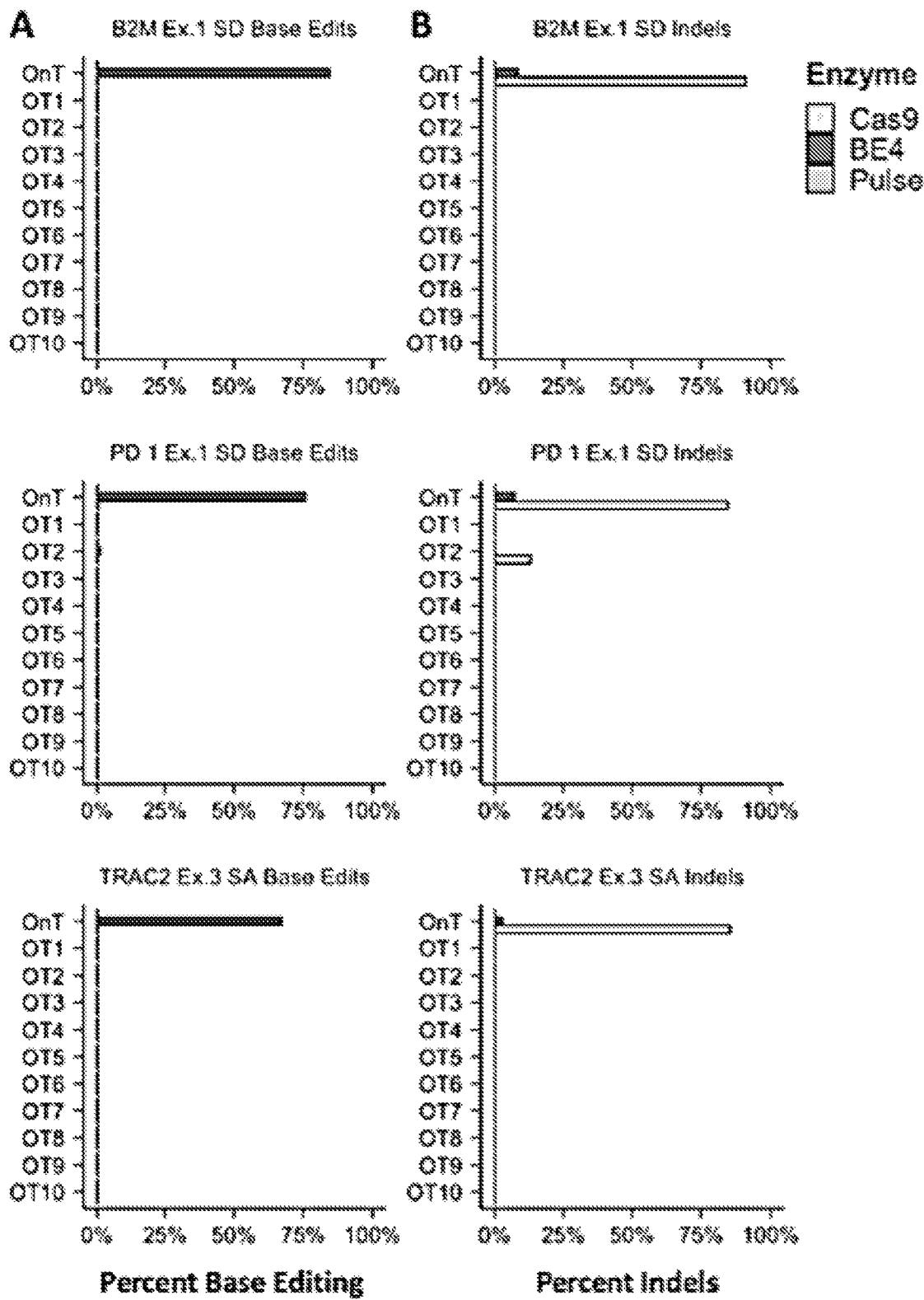
FIGS. 12A-12B demonstrate assessment of computationally predicted off-target base editing and indel formation. Base editing (A) and indel (B) frequency at on-target and top 10 computationally predicted off-target sgRNA binding sites, assessed using next generation sequencing, using optimal sgRNAs targeting TRAC, B2M or PDCD1 combined with Cas9 or BE4 mRNA in T cells.

Embodiments include multiplex gene editing methods that are simultaneous. For example, provided herein are methods for multiplex engineering in human cells using base editing. In some cases, the method comprises multiplex gene editing using a base editor fusion protein (e.g., BE3, BE4, ABE) and gRNAs in which one or more genes are disrupted (for knock-out) and one or more genes is knocked-in using a donor DNA template for insertion. Referring to FIG. 12, base editor 3 (BE3) and base editor 4 (BE4) were used with three SA-SD gRNAs to successfully knock-out expression of TRAC, B2M, and PDCD1 in human T cells. BE3 and BE4 were also used with these three SA-SD gRNAs with two AAVS1 targeting gRNAs to knock-in a donor DNA template. These data demonstrate that the base editing methods provided herein are useful for multiplexed disruption of multiple genes relevant to immunotherapy in cells (e.g., T cells), with or without knock-in of a target DNA template or missense mutation.

Provided herein are also methods for genome engineering (e.g., for altering or manipulating the expression of one or more genes or one or more gene products) in prokaryotic or eukaryotic cells, in vitro, in vivo, or ex vivo. In particular, the methods provided herein are useful for targeted base editing disruption in mammalian cells including human T cells, natural killer (NK) cells, CD34+ hematopoietic stem progenitor cells (HSPCs) (e.g., umbilical cord blood HSPCs), and fibroblasts (e.g., MPS1 fibroblasts, Fanconi Anemia fibroblasts). Importantly, as shown in FIGS. 21A-21D, fibroblasts derived from a Fanconi Anemia patient (and, thus, DNA repair-deficient) are still amenable to base editing using, for example, BE3, BE4, or ABE. Accordingly, also provided herein are genetically engineered lymphohematopoietic cells such as T cells that have been modified according to the methods described herein.

In some cases, the methods are configured to produce genetically engineered T cells that are suitable as "universally acceptable" cells for therapeutic application. As used herein, the term "universally acceptable" refers general acceptance of cell products in immunological terms, where cross-matching of patients and cells is not required, and no immunosuppression is needed. To obtain such cells, the method can comprise, for example, transfecting into a human T cell: (i) a plasmid, mRNA, or protein encoding base editor fusion protein comprising a deaminase domain fused to a Cas9 nickase domain, wherein the nickase domain comprises a base excision repair inhibitor domain; (ii) one or more splice acceptor-splice donor (SA-SD) gRNAs to disrupt expression of each of TRAC, B2M, and PDCD1, (iii) a donor DNA template encoding a T cell receptor (TCR) and a chimeric antigen receptor (CAR), and (iv) two gRNAs complementary to a target insertion site. The method further comprises culturing the transfected T cell under conditions that promote disruption of splice sites targeted by the SA-SD gRNA, whereby expression of TRAC, B2M, and PDCD1 gene products is reduced relative to an untransfected T cell; and culturing the transfected T cell under conditions that promote targeted knock-in of the donor DNA template at the target insertion site. In this example, the resulting genetically modified T cell expresses a CAR/TCR and lacks expression of TRAC, PDCD1, and B2M. In some cases, the method further comprises introducing gRNA(s) designed to disrupt expression of CTLA-4. Sequences of exemplary gRNAs for editing target bases in genes TRAC, PDCD1, and B2M are set forth in Table 1.

TABLE 1

Single-guide RNAs (sgRNAs) for T Cell and CD34+ Cell Base Editing

| gRNA Gene name | 5'-gRNA Sequence-3' | Orientation | Target base(s) | Predicted Outcome |
|---|---|---|---|---|
| PDCD1Ex. 1 SD | CACCTACCTAAGAACCATCC (SEQ ID NO: 1) | Antisense | C7 | Splice donor disruption: GT → AT |
| PDCD1Ex. 2 SA | GGAGTCTGAGAGATGGAGAG (SEQ ID NO: 2) | Antisense | C6 | Splice acceptor disruption: AG → AA |
| PDCD1Ex. 3 SA | TTCTCTCTGGAAGGGCACAA (SEQ ID NO: 3) | Antisense | C7 | Splice acceptor disruption: AG → AA |
| PDCD1Ex. 3 SD | GACGTTACCTCGTGCGGCCC (SEQ ID NO: 4) | Antisense | C8 | Splice donor disruption: GT → AT |
| PDCD1Ex. 4 SA | CCTGCAGAGAAACACACTTG (SEQ ID NO: 5) | Antisense | C2 | Splice acceptor disruption: AG → AA |
| PDCD1Ex, 2 pmSTOP | GGGGTTCCAGGGCCTGTCTG (SEQ ID NO: 6) | Antisense | C7, C8 | pmSTOP induction: TGG (Trp) → TAG, TGA, TAA |
| PDCD1Ex. 3 pmSTOP_1 | CAGTTCCAAACCCTGGTGGT (SEQ ID NO: 7) | Sense | C7 | pmSTOP induction: CAA (Gln) → TAA |

TABLE 1-continued

Single-guide RNAs (sgRNAs) for T Cell and CD34+ Cell Base Editing

| Gene | gRNA name | 5'-gRNA Sequence-3' | Orientation | Target base(s) | Predicted Outcome |
|---|---|---|---|---|---|
| PDCD1 | Ex. 3 pmSTOP_2 | GGACCCAGACTAGCAGCACC (SEQ ID NO: 8) | Antisense | C5, C6 | pmSTOP induction: TGG (Trp) → TAG, TGA, TAA |
| TRAC | Ex. 1 SD | CTTACCTGGGCTGGGGAAGA (SEQ ID NO: 9) | Antisense | C5 | Splice donor disruption: GT → AT |
| TRAC | Ex. 3 SA | TTCGTATCTGTAAAACCAAG (SEQ ID NO: 10) | Antisense | C8 | Splice acceptor disruption: AG → AA |
| TRAC | Ex. 3 pmSTOP_1 | TTTCAAAACCTGTCAGTGAT (SEQ ID NO: 11) | Sense | C4 | pmSTOP induction: CAA (Gln) → TAA |
| TRAC | Ex. 3 pmSTOP_2 | TTCAAAACCTGTCAGTGATT (SEQ ID NO: 12) | Sense | C3 | pmSTOP induction: CAA (Gln) → TAA |
| B2M | Ex. 1 SD | ACTCACGCTGGATAGCCTCC (SEQ ID NO: 13) | Antisense | C6 | Splice donor disruption: GT → AT |
| B2M | Ex. 3 SA | TCGATCTATGAAAAGACAG (SEQ ID NO: 14) | Antisense | C6 | Splice acceptor disruption: AG → AA |
| B2M | Ex. 2 pmSTOP | CTTACCCCACTTAACTATCT (SEQ ID NO: 15) | Antisense | C7, C8 | pmSTOP induction: TGG (Trp) → TAG, TGA, TAA |

Base editing fusion proteins comprise a deaminase domain fused to a Cas9 nickase domain or an inactivated Cas9 nuclease domain (referred to as dead Cas9 or dCas9), where, in some cases, the deaminase domain is an apolipoprotein B mRNA-editing complex (APOBEC) family deaminase. The APOBEC cytidine deaminase domains allow for targeted gene disruption in which a single base substitution of thymidine in place of cytidine.

In another aspect, provided herein are methods for targeting diseases for base editing correction. The target sequence can be any disease-associated polynucleotide or gene, as have been established in the art. Examples of useful applications of mutation or 'correction' of an endogenous gene sequence include alterations of disease-associated gene mutations, alterations in sequences encoding splice sites, alterations in regulatory sequences, alterations in sequences to cause a gain-of-function mutation, and/or alterations in sequences to cause a loss-of-function mutation, and targeted alterations of sequences encoding structural characteristics of a protein.

In another aspect, provided herein are methods for using base editing to obtain cleavage resistant Fc receptors. For example, the mutagenic domain of a base editing enzyme is, in some cases, used to introduce mutations that yield a FCγRIIIa (Fc Fragment Of IgG Receptor IIIa) gene product (also known as CD16a) having higher affinity. Accordingly, the method can comprise introducing into a natural killer cell components for base editing (e.g., BE3, BE4, gRNAs, donor template) to introduce mutations in CD16a that enhance the NK cell's antibody-dependent cell-mediated cytotoxicity (ADCC). Referring to FIGS. 18A-18D, base editing according to the methods provided herein successfully modified CD3⁻CD56⁺ NK cells by modifying CD16a into a cleavage-resistant form. 40% C to T editing efficiency was obtained using BE3-VQR and CD16a gRNAs.

In some cases, it will be advantageous to genetically modify a cell using the methods described herein such that cell expresses a chimeric antigen receptor (CAR) and/or T cell receptor (TCR). The "chimeric antigen receptor (CAR)" is sometimes called a "chimeric receptor", a "T-body", or a "chimeric immune receptor (CIR)." As used herein, the term "chimeric antigen receptor (CAR)" refers to an artificially constructed hybrid protein or polypeptide comprising an extracellular antigen binding domains of an antibody (e.g., single chain variable fragment (scFv)) operably linked to a transmembrane domain and at least one intracellular domain. Generally, the antigen binding domain of a CAR has specificity for a particular antigen expressed on the surface of a target cell of interest. For example, T cells can be engineered to express CAR specific for CD19 on B-cell lymphoma. For allogenic antitumor cell therapeutics not limited by donor-matching, cells can be engineered to knock-in nucleic acids encoding a CAR but also knocking out genes responsible for donor matching (TCR and HLA markers).

As used herein, the terms "genetically modified" and "genetically engineered" are used interchangeably and refer to a prokaryotic or eukaryotic cell that includes an exogenous polynucleotide, regardless of the method used for insertion. In some cases, the effector cell has been modified to comprise a non-naturally occurring nucleic acid molecule that has been created or modified by the hand of man (e.g., using recombinant DNA technology) or is derived from such a molecule (e.g., by transcription, translation, etc.). An effector cell that contains an exogenous, recombinant, synthetic, and/or otherwise modified polynucleotide is considered to be an engineered cell.

In some embodiments, components including a base editor and a guide molecule can be delivered to a cell, in vitro, ex vivo, or in vivo. In some cases, a viral or plasmid vector system is employed for delivery of base editing components described herein. Preferably, the vector is a viral vector, such as a lenti- or baculo- or preferably adeno-viral/adeno-associated viral (AAV) vectors, but other means of delivery are known (such as yeast systems, microvesicles, gene guns/means of attaching vectors to gold nanoparticles) and are contemplated. In certain embodiments, nucleic acids encoding gRNAs and base editor fusion proteins are packaged for delivery to a cell in one or more viral delivery vectors. Suitable viral delivery vectors include, without limitation, adeno-viral/adeno-associated viral (AAV) vectors, lentiviral vectors. In some cases, non-viral transfer methods as are known in the art can be used to introduce nucleic acids or proteins in mammalian cells. Nucleic acids and proteins can be delivered with a pharmaceutically acceptable vehicle, or for example, encapsulated in a liposome. Other means of delivery are known (such as yeast systems, microvesicles, gene guns/means of attaching vectors to gold nanoparticles) and are contemplated. In some cases, cells are electroporated for uptake of gRNA and base editor (e.g., BE3, BE4, ABE). In some cases, DNA donor template is delivered as Adeno-Associated Virus Type 6 (AAV6) vector by addition of viral supernatant to culture medium after introduction of the gRNA, base editor, and vector by electroporation.

Rates of insertion or deletion (indel) formation can be determined by an appropriate method. For example, Sanger sequencing or next generation sequencing (NGS) can be used to detect rates of indel formation. Preferably, the contacting results in less than 20% off-target indel formation upon base editing. The contacting results in at least 2:1 intended to unintended product upon base editing.

Cells useful for the methods provided herein can be freshly isolated primary cells or obtained from a frozen aliquot of a primary cell culture. In some cases, cells are electroporated for uptake of gRNAs and the base editing fusion protein. As described in the Examples that follow, electroporation conditions for some assays (e.g., for T cells) can comprise 1400 volts, pulse width of 10 milliseconds, 3 pulses. Following electroporation, electroporated T cells are allowed to recover in a cell culture medium and then cultured in a T cell expansion medium. In some cases, electroporated cells are allowed to recover in the cell culture medium for about 5 to about 30 minutes (e.g., about 5, 10, 15, 20, 25, 30 minutes). Preferably, the recovery cell culture medium is free of an antibiotic or other selection agent. In some cases, the T cell expansion medium is complete CTS OpTmizer T-cell Expansion medium.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

In interpreting this disclosure, all terms should be interpreted in the broadest possible manner consistent with the context. It is understood that certain adaptations of the invention described in this disclosure are a matter of routine optimization for those skilled in the art, and can be implemented without departing from the spirit of the invention, or the scope of the appended claims.

As used herein, the terms "synthetic" and "engineered" are used interchangeably and refer to the aspect of having been manipulated by the hand of man.

So that the compositions and methods provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Unless otherwise defined, all technical terms used herein have the same meaning as commonly understood by one of ordinary skill in the art to which this invention belongs. As used herein and in the claims, the singular forms "a," "an," and "the" include the singular and the plural reference unless the context clearly indicates otherwise. Thus, for example, a reference to "an agent" includes a single agent and a plurality of such agents. Any reference to "or" herein is intended to encompass "and/or" unless otherwise stated.

Various exemplary embodiments of compositions and methods according to this invention are now described in the following non-limiting Examples. The Examples are offered for illustrative purposes only and are not intended to limit the scope of the present invention in any way. Indeed, various modifications in addition to those shown and described herein will become apparent to those skilled in the art from the foregoing description and the following examples and fall within the scope of the appended claims.

EXAMPLES

This section demonstrates successful use of third- and fourth-generation base editors to knockout four different genes in primary human lymphohematopoietic cells, with efficiencies as high as 80%. Splice site disruption has proven more effective than premature stop codons for gene knockout. By way of the Cas9 nickase function of later-generation base editors, targeted gene knock-in has also been achieved with up to 70% efficiency following administration of an AAV6 vector for donor template delivery. Collectively, the assays and results described herein demonstrate an improved multiplex gene editing platform to enhance both the safety and efficacy of engineered T cell-based immunotherapies.

Example 1—Splice Site Base Editing

Base editing has been previously used to induce premature stop (pmSTOP) codons for gene knockout in mice and in mammalian cells[15-18]. However, we reasoned that splice site disruption could have several advantages over induction of pmSTOP codons (FIG. 1). For instance, stop codon read-through has been shown to occur at frequencies up to 31% in some genes, and can be promoted under conditions of cellular stress[19, 20]. Splice site editing mitigates this concern as it alters gene processing at the RNA level21, which is less likely to be bypassed at the translational level. Additionally, current base editors do not produce strict C to T edits, with even the most recent base editors producing up to 25% non-target editing (C to G/A)[22]. In the context of pmSTOP, non-target edits preclude premature stop codon formation, thereby lowering the efficiency of protein knockout, and instead create potentially undesirable amino acid changes.

Figure 2:
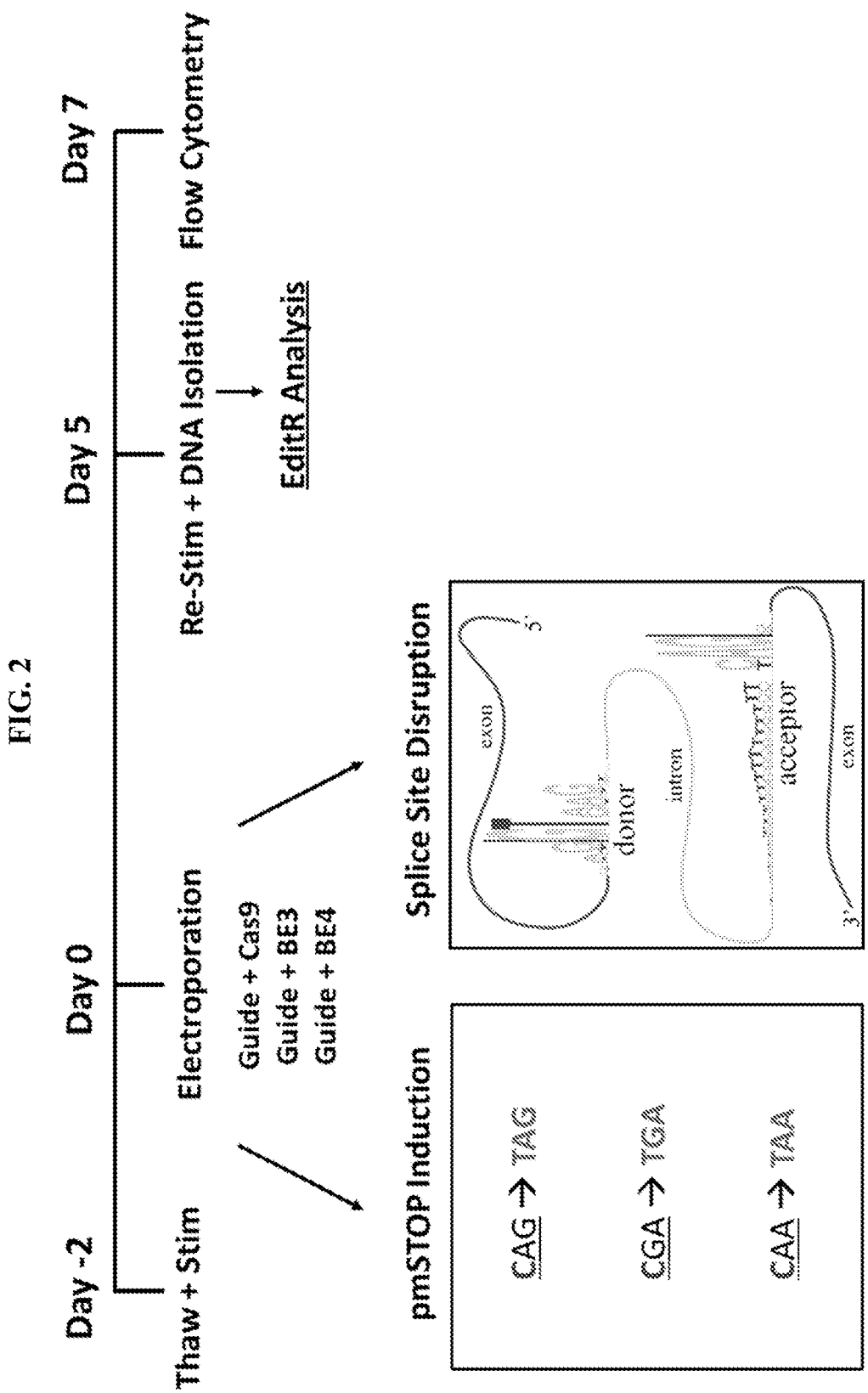
FIG. 2 illustrates an example of workflow for single gene knock-out by introduction of premature STOP (pmSTOP) codons or by splice site disruption via base editor.

To assess the performance of both pmSTOP introduction and splice-site disruption, we designed a panel of single guide RNAs (sgRNA) to convert amino acid codons to pmSTOPs or to disrupt splice donor (SD) and acceptor (SA) sequences within PDCD1, TRAC, and B2M (FIGS. 2A, 2E, 2I; Table 1). Individual sgRNAs were co-delivered as chemically modified RNA oligonucleotides[23] with first generation BE3[13] or BE4[22] mRNA to T cells by electroporation. Target C to T editing rates were assessed by Sanger sequencing and EditR, an analysis software developed by our group to expedite and economize analysis of base editing at the genetic level[24] (available at baseeditr.com on the World Wide Web).

Figures 3A, 3B, 3C, 3D, 3E, 3F, 3G, 3H, 3I, 3J, 3K, 3L:
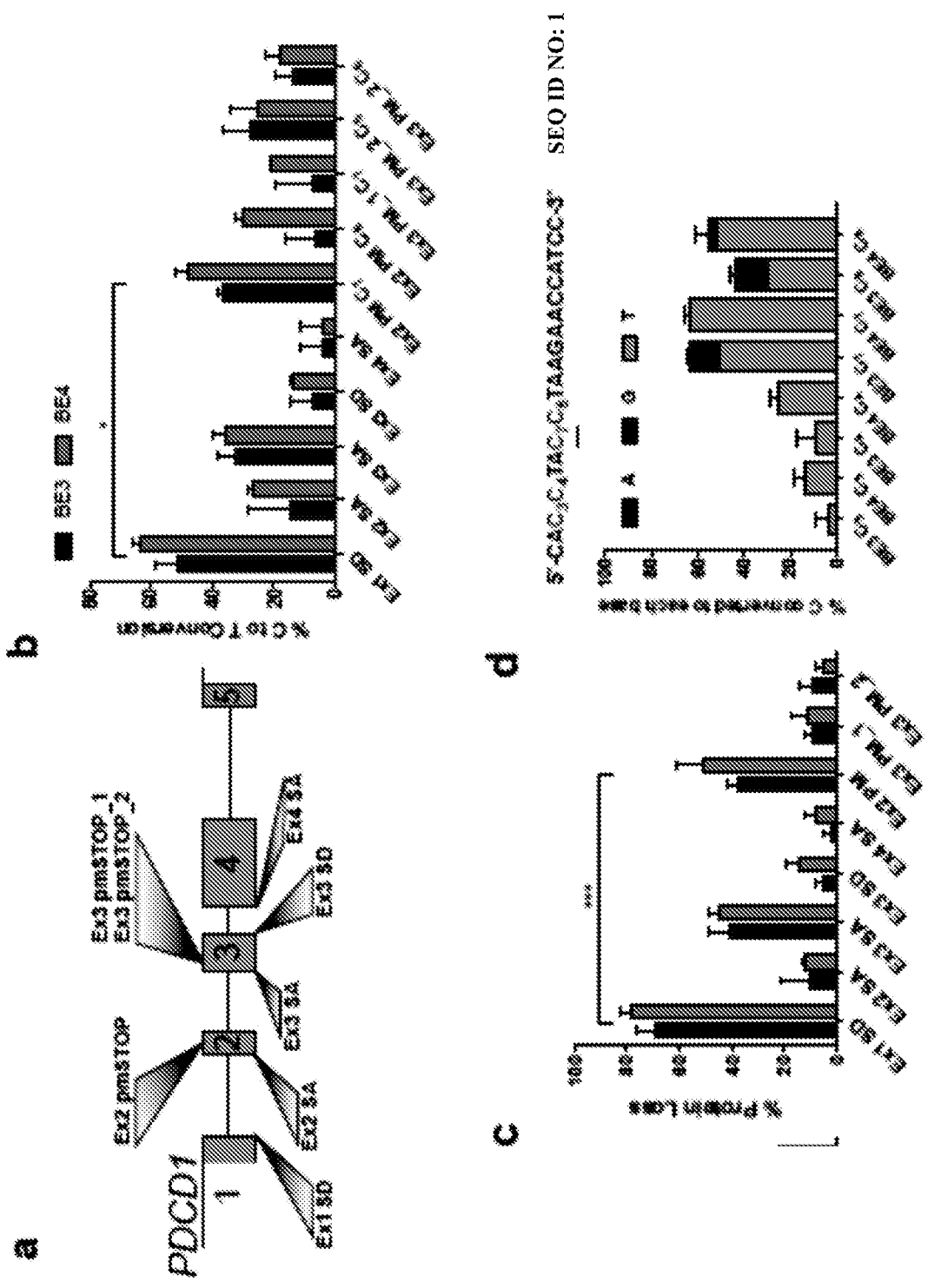
FIGS. 3A-3L demonstrate assessment of guide RNA activity for gene disruption at PDCD1, B2M, and TRAC. (a) Diagram of PDCD1 locus indicating the relative locations of each sgRNA. Colored portion of boxes represent protein coding region, vertical red line indicates stop codon. (b) Quantification of C to T conversion of target base for each PDCD1 sgRNA following co-delivery with either BE3 or BE4 mRNA as determined by EditR analysis of Sanger sequencing traces (n=3 independent T cell donors). (c) PDCD1 protein knockout frequency after delivery of the indicated sgRNAs and either BE3 or BE4 mRNA as determined by flow cytometry (n=3 independent T cell donors). (d) Quantification of C to T/A/G conversion at all Cs within the detected editing window (shown in red) of the PDCD1 Ex1 SD sgRNA following co-delivery with either BE3 or BE4 mRNA as determined by EditR analysis of Sanger sequencing traces (n=3 independent T cell donors). Underlined C indicates target nucleotide critical for proper splicing. (e) Diagram of TRAC locus indicating the relative locations of each sgRNA. (f) Quantification of C to T conversion at target base for each TRAC sgRNA following co-delivery with either BE3 or BE4 mRNA as determined by EditR analysis of Sanger sequencing traces (n=3 independent T cell donors). (g) TRAC protein knockout frequency after delivery of the indicated sgRNAs and either BE3 or BE4 mRNA as determined by flow cytometry for CD3 loss (n=3 independent T cell donors). (h) Quantification of C to T/A/G conversion at all cytosines within the detected editing window (shown in red) of the TRAC Ex3 SA sgRNA following co-delivery with either BE3 or BE4 mRNA as determined by EditR analysis of Sanger sequencing traces (n=3 independent T cell donors). (i) Diagram of B2M locus indicating the relative locations of each sgRNA. (j) Quantification of C to T conversion of target base for each B2M sgRNA following co-delivery of either BE3 or BE4 mRNA as determined by EditR analysis of Sanger sequencing traces (n=3 independent T cell donors). (k) B2M protein knockout frequency after delivery of the indicated sgRNAs and either BE3 or BE4 mRNA as determined by flow cytometry for B2M loss (n=3 independent T cell donors). (l) Quantification of C to T/A/G conversion at all cytosines within the detected editing window (shown in red) of the B2M Ex1 SD sgRNA following co-delivery with either BE3 or BE4 mRNA as determined by EditR analysis of Sanger sequencing traces (data represented as mean±SD, n=3 independent biological T cell donors). P-values calculated by Student's paired two-tailed t-test between the highest-editing guide and the second highest-editing treatment (n.s. P>0.05, * P≤0.05,  P≤0.01, * P≤0.001, **** P≤0.0001).
Figures 7A, 7B, 7C:
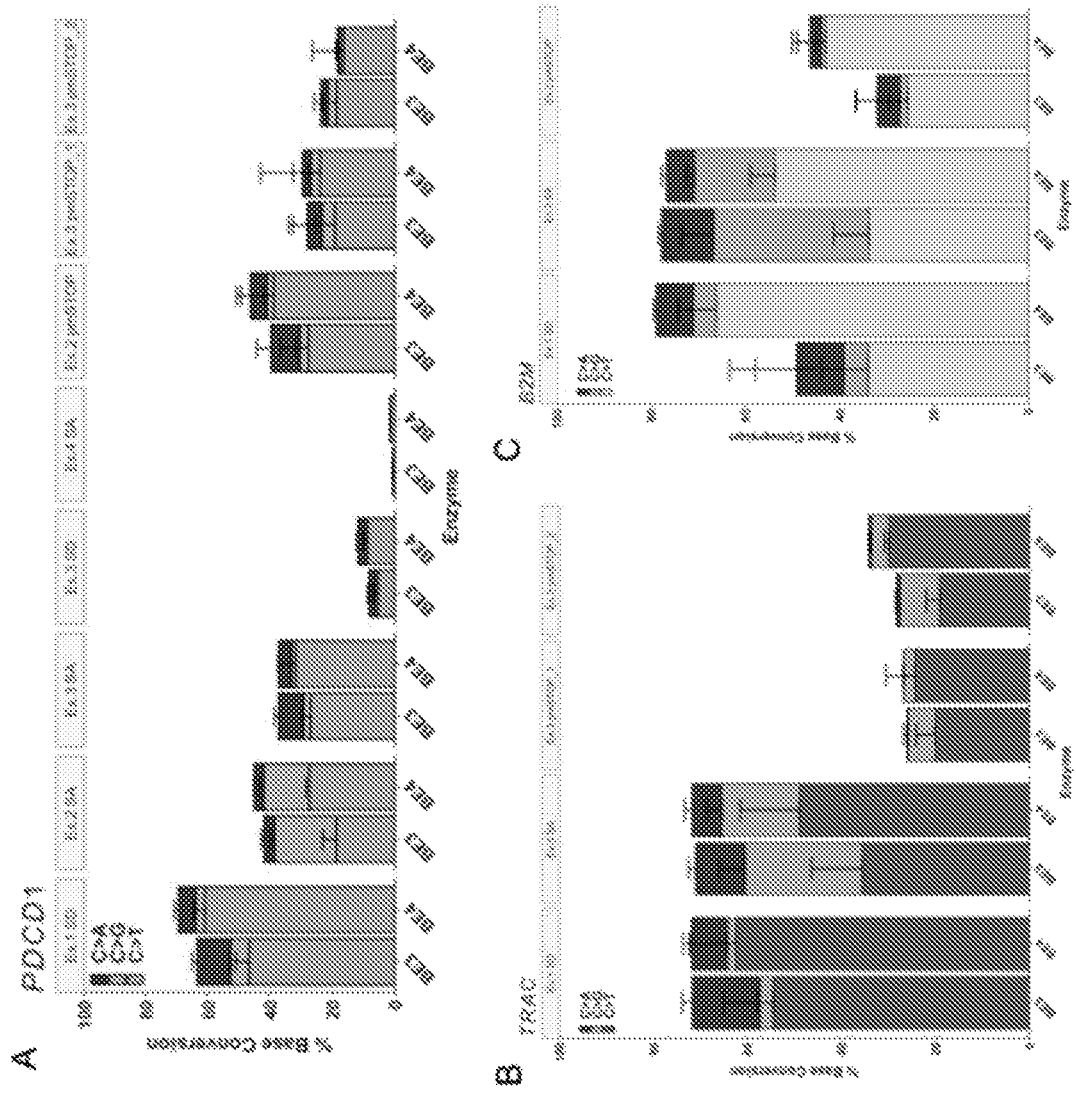
FIGS. 7A-7C demonstrate non-target editing for each sgRNA in FIGS. 3A-3L. Data is analyzed from NGS. Height of stacked bars represents mean, with error bars±1 standard deviation. n=3 independent donors.

First, we targeted the checkpoint gene PDCD1 (also known as PD-1) by designing eight sgRNAs; three of which were predicted to introduce pmSTOP codons, two targeted disruption of SD sites (GT:$\underline{C}$A), and three targeted disruption of SA sites (AG:T$\underline{C}$) (FIG. 3A). We found that co-delivery of sgRNAs with BE3 or BE4 mRNA mediated measurable editing of target Cs at all target loci, with several candidate sgRNAs exhibiting significantly higher rates of editing than others (FIG. 3B; FIGS. 7A-7C). Specifically, we found that targeting the SD site of PDCD1 exon 1 resulted in the highest rate of target C to T editing with both BE3 (51.3±7.0%, M±SD) and BE4 (63.7±2.1%) mRNA (FIG. 3B). The next two most efficient sgRNAs targeted the exon 3 SA site (32.6±5.5% for BE3; 36.0±4.0% for BE4) and a candidate pmSTOP site in exon 2 (37.1±1.2% for BE3; 48.5±3.7% for BE4) (FIG. 3B). To determine whether genetic editing results in protein loss we assessed expression of PD-1 protein by flow cytometry. Concordant with our genetic analysis, targeting PDCD1 exon 1 SD resulted in the highest rate of protein loss (69.5±7.0% for BE3; 78.6±4.1% for BE4), followed by exon 3 SA (40.6±7.8% for BE3; 44.7±3.8% for BE4), and exon 2 pmSTOP (37.9±3.4% for BE3; 51.5±9.0% for BE4) (FIG. 3C).

Informed by our PDCD1 results, we designed a focused panel of sgRNAs targeting TRAC (FIG. 3E). Here we found that C to T conversion was highest at the exon 1 SD site (47.6±4.6% for BE3; 60.0±11.3% for BE4) and exon 3 SA site (40.3±9.7% for BE3; 62.3±11.0% for BE4), with BE4 exhibiting higher editing rates than BE3 at each target (FIG. 3F). Efficient editing was also observed at two pmSTOP candidate sites in exon 3, albeit at lower efficiencies than that of either splice-site disrupting sgRNA (FIG. 3F). Both the exon 1 SD and exon 3 SA sites were edited at similar frequencies, yet disruption of the exon 3 SA site resulted in the highest rate of TCR disruption as measured by loss of cell-surface CD3 expression (69±15.3% for BE3; 83.7±5.8% for BE4) (FIG. 3G).

We next targeted B2M using a similar strategy (FIG. 3I). BE4 mRNA delivered with an sgRNA targeting the exon 1 SD site showed the most efficient C to T conversion of the target base (58.3±2.5% for BE3; 70.3±3.2% for BE4) (FIG. 3J), resulting in efficient knockout of B2M protein (79.1±1.3% for BE3; 80.0±3.2% for BE4) (FIG. 3K). We also identified a candidate pmSTOP site in exon 2 that resulted in relatively efficient C to T editing (43.3±5.7% for BE3; 55.7±5.0% for BE4), and protein knockout (56.2±5.1% for BE3; 61.5±1.8% for BE4) (FIGS. 3J, 3K). Notably, targeting the SA site of noncoding exon 3 produced efficient C to T editing but did not result in a detectable reduction in protein expression (FIGS. 3J, 3K).

Figures 8A, 8B, 8C:
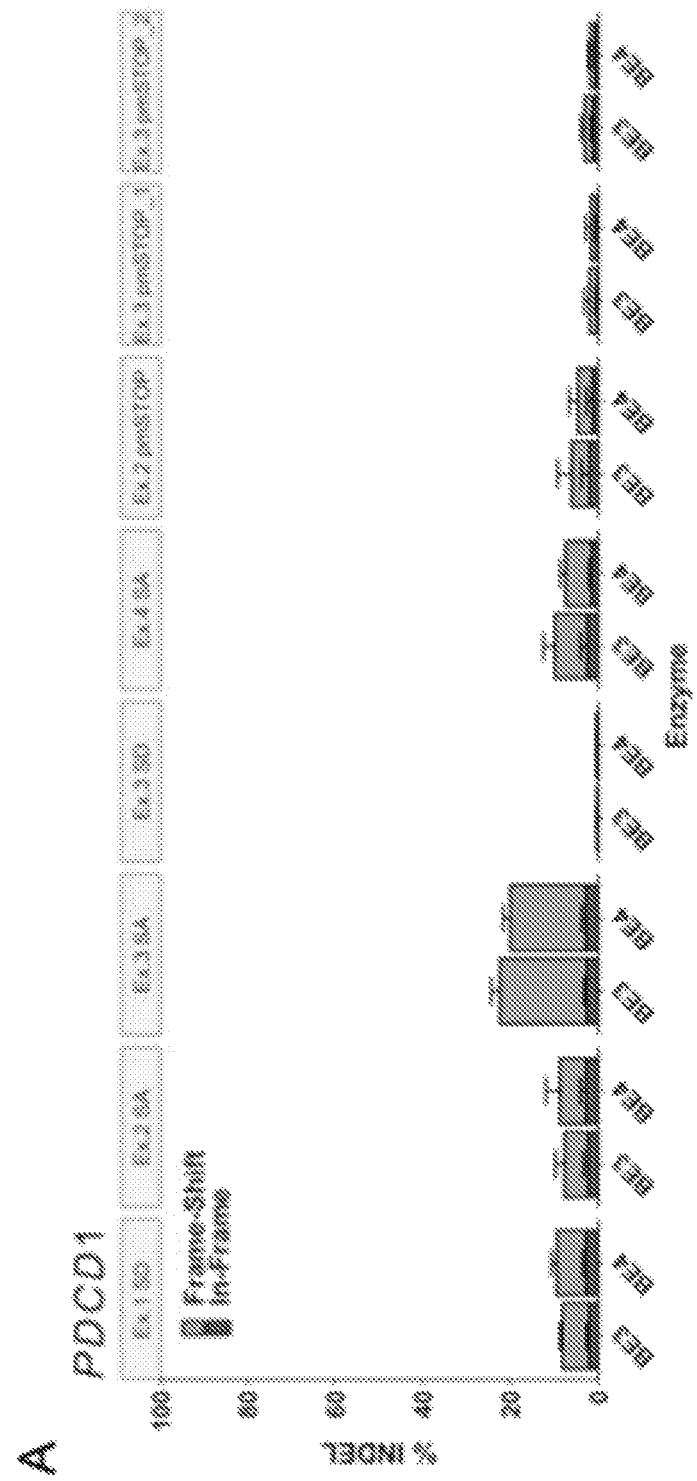
FIGS. 8A-8C present indels for all samples in FIGS. 3A-3L. Data is analyzed from NGS. Height of stacked bars represents mean, with error bars±1 standard deviation. n=3 independent donors.

Non-target editing (i.e. C to A or G) has been reported for BE3[13] and is reduced with BE4, which contains a second uracil glycosylase inhibitor (UGI) fused in series at the C-terminus[22]. We evaluated non-target editing rates for all Cs within the editing window (predominantly bases 4-8 of protospacer) of our most efficient sgRNAs with BE3 and BE4. As expected, BE4 showed reduced non-target editing compared to BE3 at all loci (−14%±6.6%, P<2.2e-16, Paired one-way t-test) (FIGS. 3D, 3H, 3L; FIGS. 7A-7C). Despite having only nickase function, low-level indel formation has been observed with both BE3 and BE4[13, 22]. Thus, we used next-generation sequencing (NGS) to measure indel frequency at all target sites after editing (FIGS. 8A-8C). Indels were detectable with both BE3 and BE4 at levels that varied based on target site. Consistent with prior publications, BE4 exhibited an overall reduced indel frequency (−4.8%±6.1%, P<4.6e-16, Paired one-way t-test) (FIGS. 8A-8C)[22].

Figure 9:
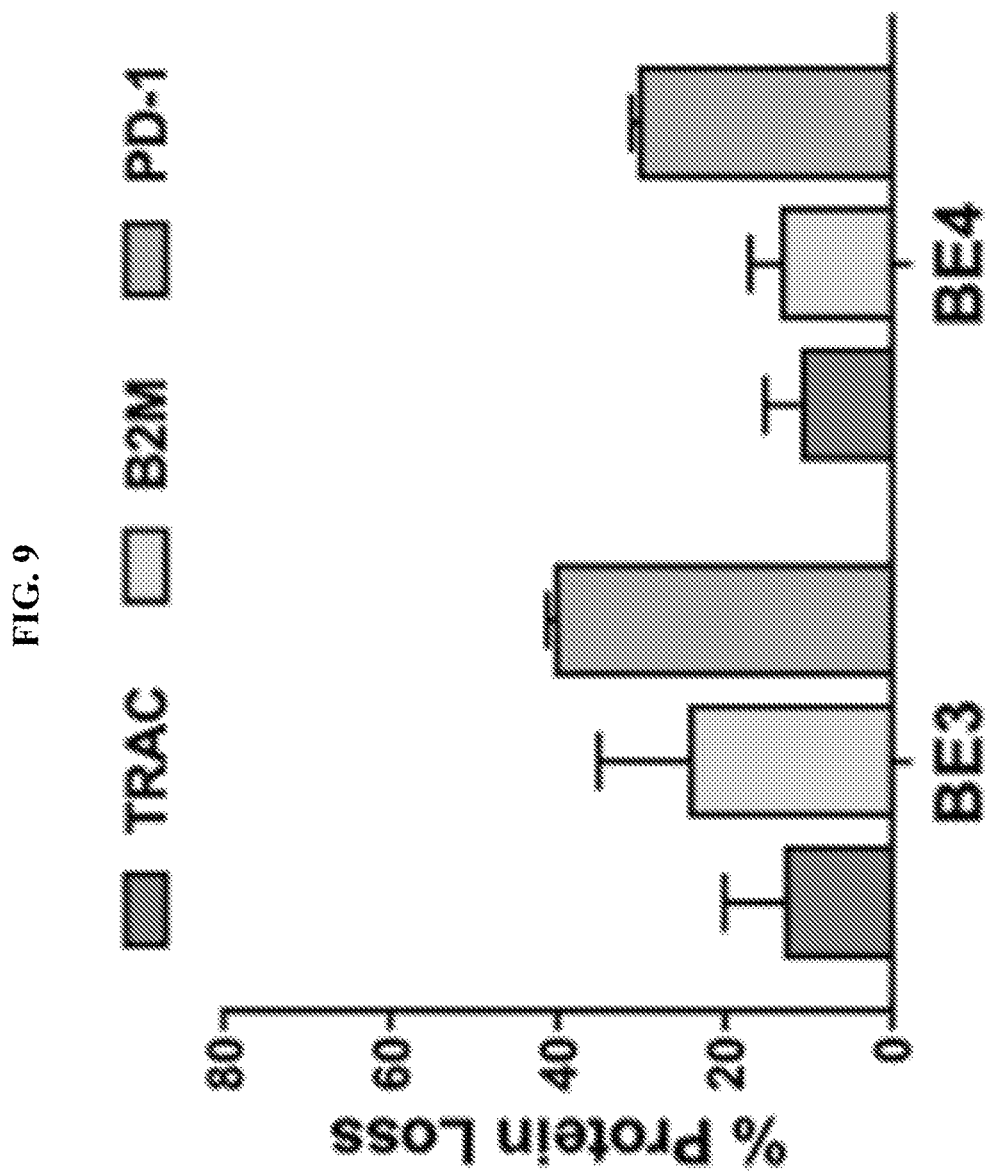
FIG. 9 demonstrates multiplex base editing of T cells using first generation, low-dose (1.5 µg) BE3 or BE4 mRNA. Bar graph depicting base editor mediated knockout of TRAC, B2M and PDCD1 at the protein level. Protein expression was assessed via flow cytometry as described in the methods section. n=2 independent donors.
Figure 10:
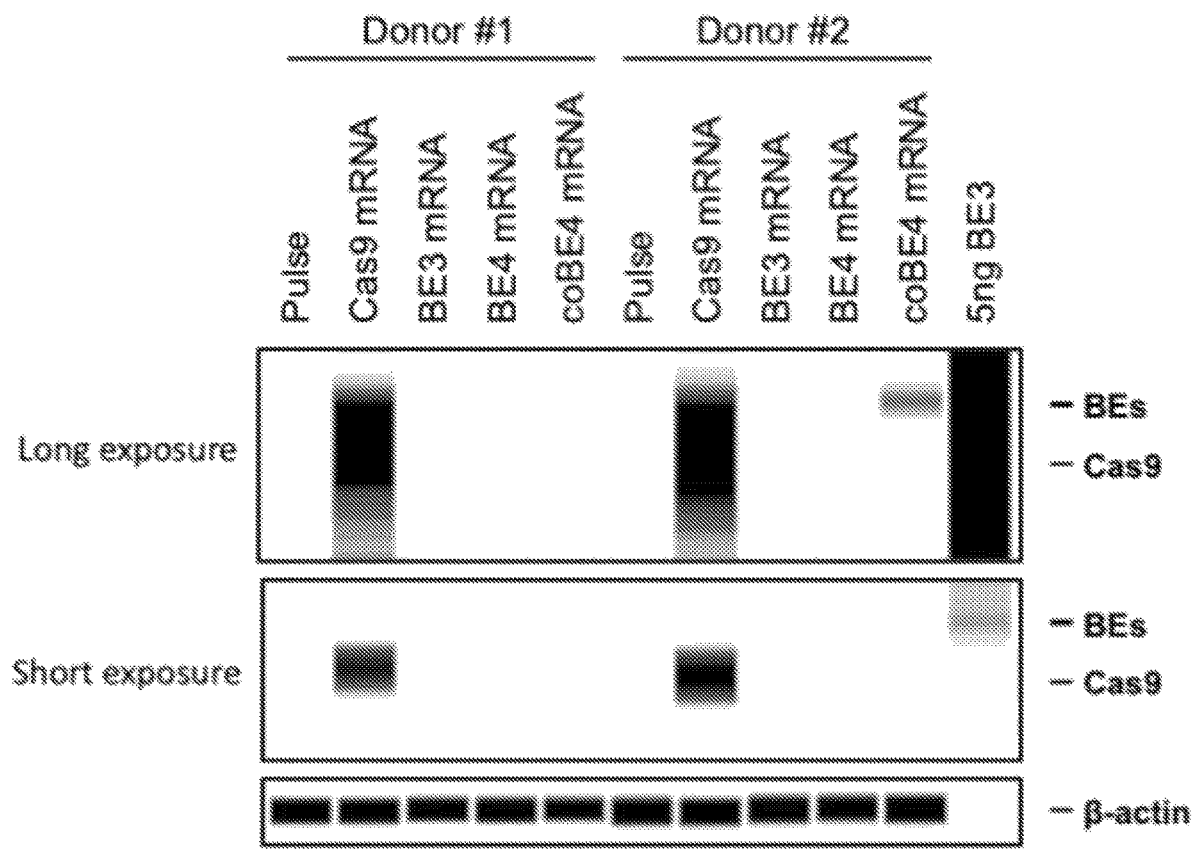
FIG. 10 demonstrates base editor protein levels following electroporation of T cells. Digital western blot results assessing the protein level achieved using mRNA encoding Cas9, BE3, BE4, and codon-optimized BE4 at 24 post-electroporation of stimulated T cells in two independent donors. Purified BE3 protein was also used as a positive control for antibody detection of BE protein.

Toward our goal of validating a multiplex editing strategy that could be utilized to generate allogeneic, "off-the-shelf" T cells with enhanced function, we co-delivered our top sgRNA for each gene along with first-generation BE3 or BE4 mRNA. Surprisingly, knockout efficiency at each target was substantially reduced for both BE3 and BE4 when delivered in a multiplex setting (FIG. 9). To determine if the reduced editing efficiency was due to low protein levels, we delivered equal doses of BE3, BE4, and nuclease active *Streptococcus pyogenes* Cas9 (SpCas9) mRNA to T cells and measured protein expression at 24 hrs after electroporation. Strikingly, while SpCas9 protein expression was readily detectable at these time points, BE3 and BE4 protein were undetectable (FIG. 10). To address this issue, we first delivered BE3 and BE4 mRNA at a dose 2× higher (3 µg) than that used in our initial multiplex experiments (1.5 µg). This strategy improved editing efficiency at each locus, but the efficiencies were still lower than those observed in our single gene targeting experiments (FIG. 4A).

During the course of these experiments, independent reports emerged identifying problems related to the use of first-generation BE3 and BE4 expression vectors that severely reduce both transcriptional and translational efficiency in human cells[17, 25]. To circumvent these issues, we delivered purified BE4 protein as a ribonucleoprotein (RNP) complex with our most effective sgRNA for each target. By optimizing our electroporation protocol for RNP delivery, we found that BE4 RNP mediated improved editing efficiency over a 2× dose of first-generation BE4 mRNA (FIG. 4C). Next, we codon optimized the sequence of BE4 (coBE4) and observed increased protein expression when delivered as mRNA (FIG. 10). When coBE4 mRNA was delivered at both our standard dose (1.5 µg) and a higher dose (4 µg) with all three of our optimal sgRNAs, we achieved substantially higher rates of multiplex target C to T editing at all three loci across multiple independent T cell donors, exceeding 90% in some instances (FIG. 4A). Non-target editing observed with first-generation BE3 and BE4 mRNA was reduced slightly when using BE4 RNP, and even further reduced with both doses of coBE4 mRNA (FIG. 4A). We next evaluated the rate of indel formation at each target site after multiplex base editing and, in accordance with previous studies, found lower rates of indel formation at each site with all forms of BE4 compared to BE3 and SpCas9 nuclease (FIGS. 4B, 4C). Both low and high doses of coBE4 mRNA exhibited the lowest overall frequency of indel formation at all sites examined (FIG. 4B).

Figures 4A, 4B, 4C, 4D, 4E, 4F:
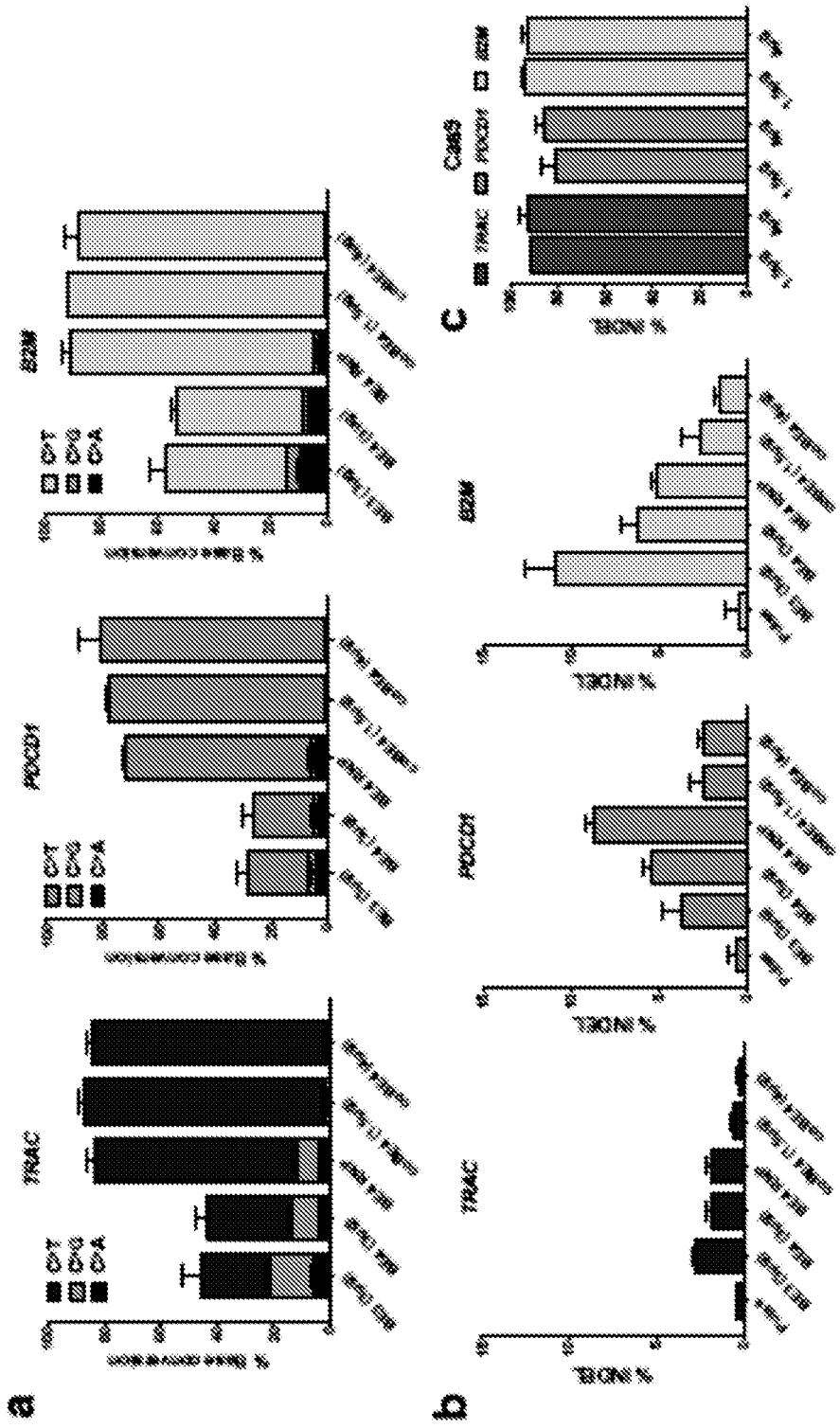
FIGS. 4A-4F demonstrates optimization of multiplex editing using optimal sgRNAs (TRAC Ex3 SA, B2M Ex1 SD, and PDCD1 Ex1 SD). (a) Conversion frequency of target cytosine to all other bases at TRAC, PDCD1, and B2M as analyzed by NGS following co-delivery of three target sgRNA with first generation BE3 (BE3) or BE4 (BE4) mRNA delivered at 3 µg dose; BE4 protein complexed with sgRNA (BE4 RNP); or codon optimized BE4 mRNA (coBE4) delivered at 1.5 µg or 4 µg doses. (b) Indel frequency at TRAC, PDCD1, and B2M as analyzed by NGS following delivery of three target sgRNA and first-generation BE3 (BE3) or BE4 (BE4) mRNA delivered at 3 µg dose; BE4 protein complexed with sgRNA (BE4 RNP); or codon optimized BE4 mRNA (coBE4) delivered at 1.5 µg or 4 µg doses. (c) Indel frequency at TRAC, PDCD1, and B2M as analyzed by NGS following co-delivery of three target sgRNA and SpCas9 nuclease mRNA at 1.5 µg or 4 µg dose. (d) Frequency of TRAC, PDCD1, and B2M protein loss measured by flow cytometry seven days after delivery of three target sgRNA and first-generation BE3 (BE3) and BE4 (BE4) mRNA delivered at 3 µg dose; BE4 protein complexed with sgRNA (BE4 RNP); and codon optimized BE4 mRNA (coBE4) delivered at 1.5 µg dose and 4 µg dose. (e) SPICE representation of multiplex flow cytometric analysis performed seven days post electroporation. (f) Quantification of fractions of WT, single, double, and triple gene KO. Data represented as mean±SD, n=2 two independent biological T cell donors.
Figure 11:
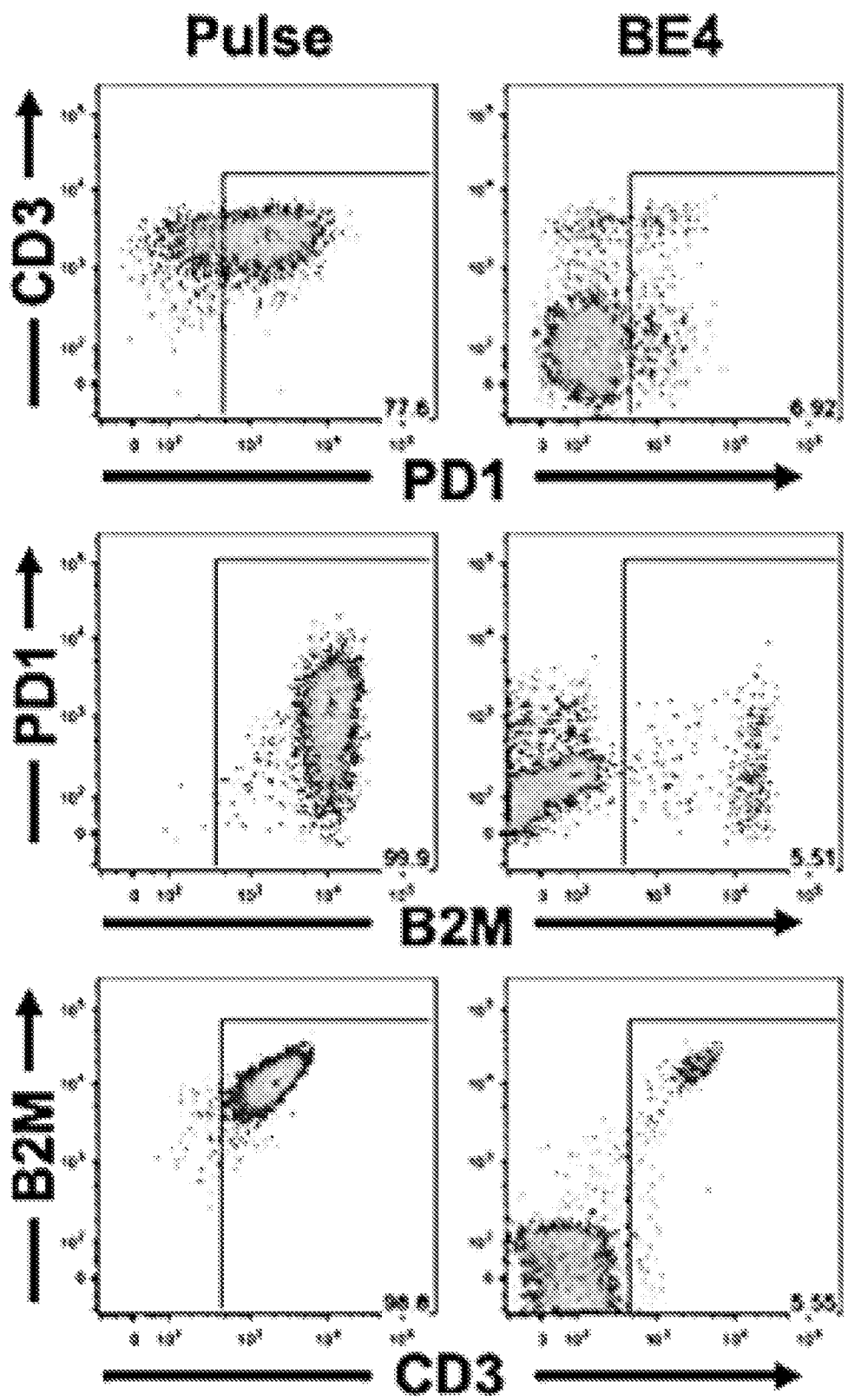
FIG. 11 presents representative flow plots of PDCD1, B2M, and TRAC upon re-stimulation. Five days post electroporation T cells are re-stimulated to induce expression of PDCD1, allowing for the assessment of PD-1 protein knock-out frequencies. Shown here are representative flow cytometry plots of TRAC, B2M, and PDCD1 expression of donor-matched T cell following multiplex co-BE4 mRNA editing and pulse-only control (left column).

Multiplex protein knockout was analyzed for each target gene by flow cytometry, and the frequency of protein loss correlated well with genetic editing frequencies (FIG. 4D, r=0.90, df=28, P=1.3e-11). BE4 RNP demonstrated more efficient protein knockout than first-generation BE3 and BE4 mRNA, yet coBE4 mRNA was most efficient, exceeding 90% protein loss for each gene at both low and high mRNA doses (FIG. 4D; FIG. 11). A key consideration of multiplex editing is the resultant proportion of cells carrying each potential combination of gene knockout. To better understand this phenomenon in our experiments, we evaluated protein expression of all target genes simultaneously by flow cytometry and used SPICE analysis to determine the proportion of individual cells having no knockout, single gene knockout, double gene knockout, or triple gene knockout; as well as the combination of proteins lost within each of these fractions (FIG. 4E). While first-generation BE4 mRNA generated an endpoint cell population with a diverse combination of knockout phenotypes, the frequency of triple knockout cells was low (21.9±1.1%). The proportion of triple knockout cells was substantially higher using BE4 RNP (68.6±0.37%), and even further increased with coBE4 mRNA at 1.5 µg (86.6±3.75%) and 4 µg (89.57±4.2%) (FIG. 4F).

Off-target (OT) DSB induction is an important challenge facing nuclease platforms[26]. To determine the specificity of our optimal sgRNAs, we delivered each individually with SpCas9 nuclease or BE4 mRNA and evaluated editing at the top 10 predicted OT sites by NGS (Table 2). No editing was observed at any of the predicted B2M or TRAC OT sites in either the SpCas9 nuclease or BE4 treatment conditions (FIG. 12). At the predicted PDCD1 OT sites we observed a single OT edit with an indel frequency of 13.0% using SpCas9 mRNA (FIG. 12). Strikingly, C to T editing at this site was only 0.9% with BE4 mRNA, and indel formation was near the low detection limit of our assay (0.2%) (FIG. 12).

TABLE 2

| | | Computationally predicted candidate off-target sites | | | | |
|---|---|---|---|---|---|---|
| Site Name | Primer Name | Primer Sequence | Off-Target Sequence | Alignment | Gene | Coordinates |
| B2M_Ex1_SD_OnT | B2M_Ex1_SD_Fwd_1 | TCGTCGGCAGCGTCAGATGTGT ATAAGAGACAGATCCAGCCCTG GACTAGC (SEQ ID NO: 16) | ACTCAcGCTGGATAGC CTCC (SEQ ID NO: 13) | ........................ | B2M | chr15:45003795-45003817 |
| B2M_Ex1_SD_OnT | B2M_Ex1_SD_Rev_1 | GTCTCGTGGGCTCGGAGATGTG TATAAGAGACAGCTCTCTCTAAC CTGGCACTG (SEQ ID NO: 17) | ACTCAcGCTGGATAGC CTCC (SEQ ID NO: 13) | ........................ | B2M | chr15:45003795-45003817 |
| B2M_Ex1_SD_OnT | B2M_Ex1_SD_Fwd_2 | TCGTCGGCAGCGTCAGATGTGT ATAAGAGACAGATCCAGCCCTG GACTAGC (SEQ ID NO: 16) | ACTCAcGCTGGATAGC CTCC (SEQ ID NO: 13) | ........................ | B2M | chr15:45003795-45003817 |
| B2M_Ex1_SD_OnT | B2M_Ex1_SD_Rev_2 | GTCTCGTGGGCTCGGAGATGTG TATAAGAGACAGCCCTCTCTAA CCTGGCACT (SEQ ID NO: 18) | ACTCAcGCTGGATAGC CTCC (SEQ ID NO: 13) | ........................ | B2M | chr15:45003795-45003817 |
| B2M_Ex1_SD_OT1 | B2M_Ex1_SD_Fwd_1 | TCGTCGGCAGCGTCAGATGTGT ATAAGAGACAGCCCAGACATGA GAAGGTTAT (SEQ ID NO: 19) | TCTGCCCCTGGATAG CCTCC (SEQ ID NO: 20) | T..GC.C.............. | PDE11A | chr2:178777091-178777113 |
| B2M_Ex1_SD_OT1 | B2M_Ex1_SD_Rev_1 | GTCTCGTGGGCTCGGAGATGTG TATAAGAGACAGCTTTACAGGC TCCCCTTC (SEQ ID NO: 21) | TCTGCCCCTGGATAG CCTCC (SEQ ID NO: 20) | T..GC.C.............. | PDE11A | chr2:178777091-178777113 |
| B2M_Ex1_SD_OT1 | B2M_Ex1_SD_Fwd_2 | TCGTCGGCAGCGTCAGATGTGT ATAAGAGACAGCCCAGACATGA GAAGGTTAT (SEQ ID NO: 19) | TCTGCCCCTGGATAG CCTCC (SEQ ID NO: 20) | T..GC.C.............. | PDE11A | chr2:178777091-178777113 |
| B2M_Ex1_SD_OT1 | B2M_Ex1_SD_Rev_2 | GTCTCGTGGGCTCGGAGATGTG TATAAGAGACAGGTCTAGGCGT CCTCATCAC (SEQ ID NO: 22) | TCTGCCCCTGGATAG CCTCC (SEQ ID NO: 20) | T..GC.C.............. | PDE11A | chr2:178777091-178777113 |
| B2M_Ex1_SD_OT2 | B2M_Ex1_SD_Fwd_1 | TCGTCGGCAGCGTCAGATGTGT ATAAGAGACAGGGATGTTCTTT GGTGTTTGT (SEQ ID NO: 23) | ACTCACCTTCCATAGC CTCC (SEQ ID NO: 24) | .......CT.CC.............. | ZNF519 | chr18:14090054-14090076 |
| B2M_Ex1_SD_OT2 | B2M_Ex1_SD_Rev_1 | GTCTCGTGGGCTCGGAGATGTG TATAAGAGACAGGACTCCGTCT CTGAACACTC (SEQ ID NO: 25) | ACTCACCTTCCATAGC CTCC (SEQ ID NO: 24) | .......CT.CC.............. | ZNF519 | chr18:14090054-14090076 |
| B2M_Ex1_SD_OT2 | B2M_Ex1_SD_Fwd_2 | TCGTCGGCAGCGTCAGATGTGT ATAAGAGACAGGAATGTTGGGA TGTTCTTTG (SEQ ID NO: 26) | ACTCACCTTCCATAGC CTCC (SEQ ID NO: 24) | .......CT.CC.............. | ZNF519 | chr18:14090054-14090076 |
| B2M_Ex1_SD_OT2 | B2M_Ex1_SD_Rev_2 | GTCTCGTGGGCTCGGAGATGTG TATAAGAGACAGGACTCCGTCT CTGAACACTC (SEQ ID NO: 25) | ACTCACCTTCCATAGC CTCC (SEQ ID NO: 24) | .......CT.CC.............. | ZNF519 | chr18:14090054-14090076 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| B2M_Ex1_SD_OT3 | B2M_Ex1_SD_OT3_Fwd_1 | TCGTCGGCAGCGTCAGATGTGTATAAGAGACAGACAGATAGTTGCCATTTCTGCTTG (SEQ ID NO: 27) | GCTCCTGCTGCATAGCCTCC (SEQ ID NO: 28) | G...CT.....C......... | KLF13 | chr15:31648182-31648204 |
| B2M_Ex1_SD_OT3 | B2M_Ex1_SD_OT3_Rev_1 | GTCTCGTGGGCTCGGAGATGTGTATAAGAGACAGAGGAGGTGAAAGACTGAAAAA (SEQ ID NO: 29) | GCTCCTGCTGCATAGCCTCC (SEQ ID NO: 28) | G...CT.....C......... | KLF13 | chr15:31648182-31648204 |
| B2M_Ex1_SD_OT3 | B2M_Ex1_SD_OT3_Fwd_2 | TCGTCGGCAGCGTCAGATGTGTATAAGAGACAGAATAGTTGCCATTTCTGCTT (SEQ ID NO: 30) | GCTCCTGCTGCATAGCCTCC (SEQ ID NO: 28) | G...CT.....C......... | KLF13 | chr15:31648182-31648204 |
| B2M_Ex1_SD_OT3 | B2M_Ex1_SD_OT3_Rev_2 | GTCTCGTGGGCTCGGAGATGTGTATAAGAGACAGGAGGGTGAAAGACTGAAAAA (SEQ ID NO: 29) | GCTCCTGCTGCATAGCCTCC (SEQ ID NO: 28) | G...CT.....C......... | KLF13 | chr15:31648182-31648204 |
| B2M_Ex1_SD_OT4 | B2M_Ex1_SD_OT4_Fwd_1 | TCGTCGGCAGCGTCAGATGTGTATAAGAGACAGTCTTTTTGTGAAGGCTTTTC (SEQ ID NO: 31) | TCTCACTGTGGTTAGCCTCC (SEQ ID NO: 32) | T......TG....T....... | NA | chr11:123367986-123368008 |
| B2M_Ex1_SD_OT4 | B2M_Ex1_SD_OT4_Rev_1 | GTCTCGTGGGCTCGGAGATGTGTATAAGAGACAGTTTGTCACCAGCTGATTGTA (SEQ ID NO: 33) | TCTCACTGTGGTTAGCCTCC (SEQ ID NO: 32) | T......TG....T....... | NA | chr11:123367986-123368008 |
| B2M_Ex1_SD_OT4 | B2M_Ex1_SD_OT4_Fwd_2 | TCGTCGGCAGCGTCAGATGTGTATAAGAGACAGTCTTTTTGTGAAGGCTTTTC (SEQ ID NO: 31) | TCTCACTGTGGTTAGCCTCC (SEQ ID NO: 32) | T......TG....T....... | NA | chr11:123367986-123368008 |
| B2M_Ex1_SD_OT4 | B2M_Ex1_SD_OT4_Rev_2 | GTCTCGTGGGCTCGGAGATGTGTATAAGAGACAGTGTCACCAGCTGATTGTAGA (SEQ ID NO: 34) | TCTCACTGTGGTTAGCCTCC (SEQ ID NO: 32) | T......TG....T....... | NA | chr11:123367986-123368008 |
| B2M_Ex1_SD_OT5 | B2M_Ex1_SD_OT5_Fwd_1 | TCGTCGGCAGCGTCAGATGTGTATAAGAGACAGCTCAAGAGCAAGAAACCAGT (SEQ ID NO: 35) | TCTCTCACTGGATAGCCTAC (SEQ ID NO: 36) | T....T.A............A. | NA | chr1:144373808-144373830 |
| B2M_Ex1_SD_OT5 | B2M_Ex1_SD_OT5_Rev_1 | GTCTCGTGGGCTCGGAGATGTGTATAAGAGACAGAGGACTTTGAAATACCAGCA (SEQ ID NO: 37) | TCTCTCACTGGATAGCCTAC (SEQ ID NO: 36) | T....T.A............A. | NA | chr1:144373808-144373830 |
| B2M_Ex1_SD_OT5 | B2M_Ex1_SD_OT5_Fwd_2 | TCGTCGGCAGCGTCAGATGTGTATAAGAGACAGGTGAGTCAGCAGCTCAAGA (SEQ ID NO: 38) | TCTCTCACTGGATAGCCTAC (SEQ ID NO: 36) | T....T.A............A. | NA | chr1:144373808-144373830 |
| B2M_Ex1_SD_OT5 | B2M_Ex1_SD_OT5_Rev_2 | GTCTCGTGGGCTCGGAGATGTGTATAAGAGACAGAGGACTTTGAAATACCAGCA (SEQ ID NO: 37) | TCTCTCACTGGATAGCCTAC (SEQ ID NO: 36) | T....T.A............A. | NA | chr1:144373808-144373830 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| B2M_Ex1_SD_OT6 | B2M_Ex1_SD_OT6 Fwd 1 | TCGTCGGCAGCGTCAGATGTGT ATAAGAGACAGCTCAAGAGCAA GAAACCAGT (SEQ ID NO: 35) | TCTCTCACTGGATAGC CTAC (SEQ ID NO: 36) | T...T.A...........A. | LINC01138 | chr1:147964949-147964971 |
| B2M_Ex1_SD_OT6 | B2M_Ex1_SD_OT6 Rev 1 | GTCTCGTGGGCTCGGAGATGTG TATAAGAGACAGAGGACTTTGA AATACCAGCA (SEQ ID NO: 37) | TCTCTCACTGGATAGC CTAC (SEQ ID NO: 36) | T...T.A...........A. | LINC01138 | chr1:147964949-147964971 |
| B2M_Ex1_SD_OT6 | B2M_Ex1_SD_OT6 Fwd 2 | TCGTCGGCAGCGTCAGATGTGT ATAAGAGACAGTGAGTCAGCA GCTCAAGA (SEQ ID NO: 38) | TCTCTCACTGGATAGC CTAC (SEQ ID NO: 36) | T...T.A...........A. | LINC01138 | chr1:147964949-147964971 |
| B2M_Ex1_SD_OT6 | B2M_Ex1_SD_OT6 Rev 2 | GTCTCGTGGGCTCGGAGATGTG TATAAGAGACAGAGGACTTTGA AATACCAGCA (SEQ ID NO: 37) | TCTCTCACTGGATAGC CTAC (SEQ ID NO: 36) | T...T.A...........A. | LINC01138 | chr1:147964949-147964971 |
| B2M_Ex1_SD_OT7 | B2M_Ex1_SD_OT7 Fwd 1 | TCGTCGGCAGCGTCAGATGTGT ATAAGAGACAGCTCAAGAGCAA GAAACCAGT (SEQ ID NO: 35) | TCTCTCACTGGATAGC CTAC (SEQ ID NO: 36) | T...T.A...........A. | NA | chr1:149543388-149543410 |
| B2M_Ex1_SD_OT7 | B2M_Ex1_SD_OT7 Rev 1 | GTCTCGTGGGCTCGGAGATGTG TATAAGAGACAGAGGACTTTGA AATACCAGCA (SEQ ID NO: 37) | TCTCTCACTGGATAGC CTAC (SEQ ID NO: 36) | T...T.A...........A. | NA | chr1:149543388-149543410 |
| B2M_Ex1_SD_OT7 | B2M_Ex1_SD_OT7 Fwd 2 | TCGTCGGCAGCGTCAGATGTGT ATAAGAGACAGTGAGTCAGCA GCTCAAGA (SEQ ID NO: 38) | TCTCTCACTGGATAGC CTAC (SEQ ID NO: 36) | T...T.A...........A. | NA | chr1:149543388-149543410 |
| B2M_Ex1_SD_OT7 | B2M_Ex1_SD_OT7 Rev 2 | GTCTCGTGGGCTCGGAGATGTG TATAAGAGACAGAGGACTTTGA AATACCAGCA (SEQ ID NO: 37) | TCTCTCACTGGATAGC CTAC (SEQ ID NO: 36) | T...T.A...........A. | NA | chr1:149543388-149543410 |
| B2M_Ex1_SD_OT8 | B2M_Ex1_SD_OT8 Fwd 1 | TCGTCGGCAGCGTCAGATGTGT ATAAGAGACAGAGCTCAGCTTG CTCCACT (SEQ ID NO: 39) | AGCCACCCTGGAGAG CCTCC (SEQ ID NO: 40) | .GC...C......G...... | LRRC8E | chr19:7964982-7965004 |
| B2M_Ex1_SD_OT8 | B2M_Ex1_SD_OT8 Rev 1 | GTCTCGTGGGCTCGGAGATGTG TATAAGAGACAGGCTTCTTGAG GCTGTTCA (SEQ ID NO: 41) | AGCCACCCTGGAGAG CCTCC (SEQ ID NO: 40) | .GC...C......G...... | LRRC8E | chr19:7964982-7965004 |
| B2M_Ex1_SD_OT8 | B2M_Ex1_SD_OT8 Fwd 2 | TCGTCGGCAGCGTCAGATGTGT ATAAGAGACAGAGCTCAGCTTG CTCCACT (SEQ ID NO: 39) | AGCCACCCTGGAGAG CCTCC (SEQ ID NO: 40) | .GC...C......G...... | LRRC8E | chr19:7964982-7965004 |
| B2M_Ex1_SD_OT8 | B2M_Ex1_SD_OT8 Rev 2 | GTCTCGTGGGCTCGGAGATGTG TATAAGAGACAGCTCTTGAGG CTGTTCAGG (SEQ ID NO: 42) | AGCCACCCTGGAGAG CCTCC (SEQ ID NO: 40) | .GC...C......G...... | LRRC8E | chr19:7964982-7965004 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| B2M_Ex1_SD_OT9 | B2M_Ex1_SD_OT9_Fwd_1 | TCGTCTCGGCAGCGTCAGATGTGTATAAGAGACAGCTTTCGCCAGCTCAAAAA (SEQ ID NO: 43) | ACTCCCGCTGGAAAGCCTGC (SEQ ID NO: 44) | ....C........A.....G. | NA | chr17:20755870-20755892 |
| B2M_Ex1_SD_OT9 | B2M_Ex1_SD_OT9_Rev_1 | GTCTCGTGGGCTCGGAGATGTGTATAAGAGACAGCAGCGAGCTCTACTGGTG (SEQ ID NO: 45) | ACTCCCGCTGGAAAGCCTGC (SEQ ID NO: 44) | ....C........A.....G. | NA | chr17:20755870-20755892 |
| B2M_Ex1_SD_OT9 | B2M_Ex1_SD_OT9_Fwd_2 | TCGTCTCGGCAGCGTCAGATGTGTATAAGAGACAGCTTTCGCCAGCTCAAAAA (SEQ ID NO: 43) | ACTCCCGCTGGAAAGCCTGC (SEQ ID NO: 44) | ....C........A.....G. | NA | chr17:20755870-20755892 |
| B2M_Ex1_SD_OT9 | B2M_Ex1_SD_OT9_Rev_2 | GTCTCGTGGGCTCGGAGATGTGTATAAGAGACAGCGAGCTCTACTGGTGCTG (SEQ ID NO: 46) | ACTCCCGCTGGAAAGCCTGC (SEQ ID NO: 44) | ....C........A.....G. | NA | chr17:20755870-20755892 |
| B2M_Ex1_SD_OT10 | B2M_Ex1_SD_OT10_Fwd_1 | TCGTCTCGGCAGCGTCAGATGTGTATAAGAGACAGGGTGGATTACAATGGAAACA (SEQ ID NO: 47) | CCTCCCGCTGTGTAGCCTCC (SEQ ID NO: 48) | C...C........TG...... | COL13A1 | chr10:71685789-71685811 |
| B2M_Ex1_SD_OT10 | B2M_Ex1_SD_OT10_Rev_1 | GTCTCGTGGGCTCGGAGATGTGTATAAGAGACAGCATGAAAGGGGTTATACAT (SEQ ID NO: 49) | CCTCCCGCTGTGTAGCCTCC (SEQ ID NO: 48) | C...C........TG...... | COL13A1 | chr10:71685789-71685811 |
| B2M_Ex1_SD_OT10 | B2M_Ex1_SD_OT10_Fwd_2 | TCGTCTCGGCAGCGTCAGATGTGTATAAGAGACAGGATTACAATGGAAACATCAA (SEQ ID NO: 50) | CCTCCCGCTGTGTAGCCTCC (SEQ ID NO: 48) | C...C........TG...... | COL13A1 | chr10:71685789-71685811 |
| B2M_Ex1_SD_OT10 | B2M_Ex1_SD_OT10_Rev_2 | GTCTCGTGGGCTCGGAGATGTGTATAAGAGACAGCATGAAAGGGGTTATACAT (SEQ ID NO: 49) | CCTCCCGCTGTGTAGCCTCC (SEQ ID NO: 48) | C...C........TG...... | COL13A1 | chr10:71685789-71685811 |
| PD-1_Ex_SD_OnT | PD-1_Ex.1_SD_OnT_Fwd_1 | TCGTCTCGGCAGCGTCAGATGTGTATAAGAGACAGCTGCCAGGGACTGAGAGT (SEQ ID NO: 51) | CACCTAcACTAAGAACCATCC (SEQ ID NO: 52) | ..................... | PDCD1 | chr2:242800908-242800930 |
| PD-1_Ex_SD_OnT | PD-1_Ex.1_SD_OnT_Rev_1 | GTCTCGTGGGCTCGGAGATGTGTATAAGAGACAGGTGGATGTGGAGGAAGAG (SEQ ID NO: 53) | CACCTAcACTAAGAACCATCC (SEQ ID NO: 52) | ..................... | PDCD1 | chr2:242800908-242800930 |
| PD-1_Ex_SD_OnT | PD-1_Ex.1_SD_OnT_Fwd_2 | TCGTCTCGGCAGCGTCAGATGTGTATAAGAGACAGCTGCCAGGGACTGAGAGT (SEQ ID NO: 51) | CACCTAcACTAAGAACCATCC (SEQ ID NO: 52) | ..................... | PDCD1 | chr2:242800908-242800930 |
| PD-1_Ex_SD_OnT | PD-1_Ex.1_SD_OnT_Rev_2 | GTCTCGTGGGCTCGGAGATGTGTATAAGAGACAGACGTGGATGTGGAGGAAG (SEQ ID NO: 54) | CACCTAcACTAAGAACCATCC (SEQ ID NO: 52) | ..................... | PDCD1 | chr2:242800908-242800930 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| PD-1_Ex_SD_OT1 | PD-1_Ex.1_SD_OT1_Fwd 1 | TCGTCGGCAGCGTCAGATGTGT ATAAGAGACAGTTTCACTTCTAT CCCACACC (SEQ ID NO: 55) | CGGCCACCTGAGAAC CATCC (SEQ ID NO: 56) | .GG.C.....G........ | CDKL5 | chrX:18663622-18663644 |
| PD-1_Ex_SD_OT1 | PD-1_Ex.1_SD_OT1_Rev 1 | GTCTCGTGGGCTCGGAGATGTG TATAAGAGACAGAAAGTTCTCT GGTTCCTGTG (SEQ ID NO: 57) | CGGCCACCTGAGAAC CATCC (SEQ ID NO: 56) | .GG.C.....G........ | CDKL5 | chrX:18663622-18663644 |
| PD-1_Ex_SD_OT1 | PD-1_Ex.1_SD_OT1_Fwd 2 | TCGTCGGCAGCGTCAGATGTGT ATAAGAGACAGTTTCACTTCTAT CCCACACC (SEQ ID NO: 55) | CGGCCACCTGAGAAC CATCC (SEQ ID NO: 56) | .GG.C.....G........ | CDKL5 | chrX:18663622-18663644 |
| PD-1_Ex_SD_OT1 | PD-1_Ex.1_SD_OT1_Rev 2 | GTCTCGTGGGCTCGGAGATGTG TATAAGAGACAGGAAAAGTTCT CTGGTTCCTG (SEQ ID NO: 57) | CGGCCACCTGAGAAC CATCC (SEQ ID NO: 56) | .GG.C.....G........ | CDKL5 | chrX:18663622-18663644 |
| PD-1_Ex_SD_OT2 | PD-1_Ex.1_SD_OT2_Fwd 1 | TCGTCGGCAGCGTCAGATGTGT ATAAGAGACAGGGGCCACTTGT GCTAGAG (SEQ ID NO: 58) | ACCTGACCTAAGAACC ATCC (SEQ ID NO: 59) | AC.TG.............. | ST8SIA2 | chr15:92989355-92989377 |
| PD-1_Ex_SD_OT2 | PD-1_Ex.1_SD_OT2_Rev 1 | GTCTCGTGGGCTCGGAGATGTG TATAAGAGACAGACATAGTGCCC ATGATGCAG (SEQ ID NO: 60) | ACCTGACCTAAGAACC ATCC (SEQ ID NO: 59) | AC.TG.............. | ST8SIA2 | chr15:92989355-92989377 |
| PD-1_Ex_SD_OT2 | PD-1_Ex.1_SD_OT2_Fwd 2 | TCGTCGGCAGCGTCAGATGTGT ATAAGAGACAGCATGTACACGT CTGACCACT (SEQ ID NO: 61) | ACCTGACCTAAGAACC ATCC (SEQ ID NO: 59) | AC.TG.............. | ST8SIA2 | chr15:92989355-92989377 |
| PD-1_Ex_SD_OT2 | PD-1_Ex.1_SD_OT2_Rev 2 | GTCTCGTGGGCTCGGAGATGTG TATAAGAGACAGGAATTACTAG TGCCCATGAT (SEQ ID NO: 62) | ACCTGACCTAAGAACC ATCC (SEQ ID NO: 59) | AC.TG.............. | ST8SIA2 | chr15:92989355-92989377 |
| PD-1_Ex_SD_OT3 | PD-1_Ex.1_SD_OT3_Fwd 1 | TCGTCGGCAGCGTCAGATGTGT ATAAGAGACAGACACTAACGAT TGCTGATGA (SEQ ID NO: 63) | CTTCTATCTCAGAACC ATCC (SEQ ID NO: 64) | .TT...T..C........ | QRFPR | chr4:122259478-122259500 |
| PD-1_Ex_SD_OT3 | PD-1_Ex.1_SD_OT3_Rev 1 | GTCTCGTGGGCTCGGAGATGTG TATAAGAGACAGTTTCTCACTCG CTCTTTCTC (SEQ ID NO: 65) | CTTCTATCTCAGAACC ATCC (SEQ ID NO: 64) | .TT...T..C........ | QRFPR | chr4:122259478-122259500 |
| PD-1_Ex_SD_OT3 | PD-1_Ex.1_SD_OT3_Fwd 2 | TCGTCGGCAGCGTCAGATGTGT ATAAGAGACACACTAACGATT GCTGATGAC (SEQ ID NO: 66) | CTTCTATCTCAGAACC ATCC (SEQ ID NO: 64) | .TT...T..C........ | QRFPR | chr4:122259478-122259500 |
| PD-1_Ex_SD_OT3 | PD-1_Ex.1_SD_OT3_Rev 2 | GTCTCGTGGGCTCGGAGATGTG TATAAGAGACAGTTTCTCACTCG CTCTTTCTC (SEQ ID NO: 65) | CTTCTATCTCAGAACC ATCC (SEQ ID NO: 64) | .TT...T..C........ | QRFPR | chr4:122259478-122259500 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| PD-1_Ex_SD_OT4 | PD-1_Ex.1_SD_OT4_Fwd 1 | TCGTCGGCAGCGTCAGATGTGT ATAAGAGACAGTTCTAGCTTCT GCCTTCTC (SEQ ID NO: 67) | TACCCAGCTCAGAACC ATCC (SEQ ID NO: 68) | T...C.G.C......... | NA | chr16:8315346-8315368 |
| PD-1_Ex_SD_OT4 | PD-1_Ex.1_SD_OT4_Rev 1 | GTCTCGTGGGCTCGAGATGTG TATAAGAGACAGTGCTTTTCAGA ATTGATGTG (SEQ ID NO: 69) | TACCCAGCTCAGAACC ATCC (SEQ ID NO: 68) | T...C.G.C......... | NA | chr16:8315346-8315368 |
| PD-1_Ex_SD_OT4 | PD-1_Ex.1_SD_OT4_Fwd 2 | TCGTCGGCAGCGTCAGATGTGT ATAAGAGACAGATTTCTAGCTTC TGCCTTCTC (SEQ ID NO: 70) | TACCCAGCTCAGAACC ATCC (SEQ ID NO: 68) | T...C.G.C......... | NA | chr16:8315346-8315368 |
| PD-1_Ex_SD_OT4 | PD-1_Ex.1_SD_OT4_Rev 2 | GTCTCGTGGGCTCGAGATGTG TATAAGAGACAGTGCTTTTCAGA ATTGATGTG (SEQ ID NO: 69) | TACCCAGCTCAGAACC ATCC (SEQ ID NO: 68) | T...C.G.C......... | NA | chr16:8315346-8315368 |
| PD-1_Ex_SD_OT5 | PD-1_Ex.1_SD_OT5_Fwd 1 | TCGTCGGCAGCGTCAGATGTGT ATAAGAGACAGTGTAGTTCAGG GCTGTTAGG (SEQ ID NO: 71) | CACTCACTTAAGTACC ATCG (SEQ ID NO: 72) | ...TC..T.....T.... | NA | chr3:148663173-148663195 |
| PD-1_Ex_SD_OT5 | PD-1_Ex.1_SD_OT5_Rev 1 | GTCTCGTGGGCTCGAGATGTG TATAAGAGACAGTTTCAAAACTA ACCAATCTGC (SEQ ID NO: 73) | CACTCACTTAAGTACC ATCG (SEQ ID NO: 72) | ...TC..T.....T.... | NA | chr3:148663173-148663195 |
| PD-1_Ex_SD_OT5 | PD-1_Ex.1_SD_OT5_Fwd 2 | TCGTCGGCAGCGTCAGATGTGT ATAAGAGACAGGCTGTTAGGGA GACTGAGAA (SEQ ID NO: 74) | CACTCACTTAAGTACC ATCG (SEQ ID NO: 72) | ...TC..T.....T.... | NA | chr3:148663173-148663195 |
| PD-1_Ex_SD_OT5 | PD-1_Ex.1_SD_OT5_Rev 2 | GTCTCGTGGGCTCGAGATGTG TATAAGAGACAGTTTCAAAACTA ACCAATCTGC (SEQ ID NO: 73) | CACTCACTTAAGTACC ATCG (SEQ ID NO: 72) | ...TC..T.....T.... | NA | chr3:148663173-148663195 |
| PD-1_Ex_SD_OT6 | PD-1_Ex.1_SD_OT6_Fwd 1 | TCGTCGGCAGCGTCAGATGTGT ATAAGAGACAGTGAGGAGGCA TCCGAGT (SEQ ID NO: 75) | CACAAACCTGAGAACC ATCG (SEQ ID NO: 76) | ...AA......G...... G | ATP11A | chr13:113377068-113377090 |
| PD-1_Ex_SD_OT6 | PD-1_Ex.1_SD_OT6_Rev 1 | GTCTCGTGGGCTCGAGATGTG TATAAGAGACAGCAATTAAA GAATCTCTGAAAA (SEQ ID NO: 77) | CACAAACCTGAGAACC ATCG (SEQ ID NO: 76) | ...AA......G...... G | ATP11A | chr13:113377068-113377090 |
| PD-1_Ex_SD_OT6 | PD-1_Ex.1_SD_OT6_Fwd 2 | TCGTCGGCAGCGTCAGATGTGT ATAAGAGACAGAAGGAGGGG GTGAGGAG (SEQ ID NO: 78) | CACAAACCTGAGAACC ATCG (SEQ ID NO: 76) | ...AA......G...... G | ATP11A | chr13:113377068-113377090 |
| PD-1_Ex_SD_OT6 | PD-1_Ex.1_SD_OT6_Rev 2 | GTCTCGTGGGCTCGAGATGTG TATAAGAGACAGAAAGTAAAGC ATTTCTGAATCC (SEQ ID NO: 79) | CACAAACCTGAGAACC ATCG (SEQ ID NO: 76) | ...AA......G...... G | ATP11A | chr13:113377068-113377090 |
| PD- | PD- | TCGTCGGCAGCGTCAGATGTGT | CACCTCCATTTGAACC | ......C.A.TT...... | GRID1 | chr10:87654974-87654996 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| 1_Ex_SD_OT7 | PD-1_Ex.1_SD_OT7 Fwd 1 | ATAAGAGACAGACCCTGCACAG AACCTATAA (SEQ ID NO: 80) | CACCTCCATTGAACC ATCC (SEQ ID NO: 81) | ......C.A.TT......... | GRID1 | chr10:87654974-87654996 |
| PD-1_Ex_SD_OT7 | PD-1_Ex.1_SD_OT7 Rev 1 | GTCTCGTGGGCTCGAGATGTG TATAAGAGACAGAAGGACTTGG CTTGTCTTCT (SEQ ID NO: 82) | CACCTCCATTGAACC ATCC (SEQ ID NO: 81) | ......C.A.TT......... | GRID1 | chr10:87654974-87654996 |
| PD-1_Ex_SD_OT7 | PD-1_Ex.1_SD_OT7 Fwd 2 | TCGTCGGCAGCGTCAGATGTGT ATAAGAGACAGACCCTGCACAG AACCTATAA (SEQ ID NO: 80) | CACCTCCATTGAACC ATCC (SEQ ID NO: 81) | ......C.A.TT......... | GRID1 | chr10:87654974-87654996 |
| PD-1_Ex_SD_OT7 | PD-1_Ex.1_SD_OT7 Rev 2 | GTCTCGTGGGCTCGAGATGTG TATAAGAGACAGGACTTGGCTT GTCTTCTGAT (SEQ ID NO: 83) | CACCTCCATTGAACC ATCC (SEQ ID NO: 81) | ......C.A.TT......... | GRID1 | chr10:87654974-87654996 |
| PD-1_Ex_SD_OT8 | PD-1_Ex.1_SD_OT8 Fwd 1 | TCGTCGGCAGCGTCAGATGTGT ATAAGAGACAGCCTATTTCATAT TGGGTGA (SEQ ID NO: 84) | CACCCACCTAAGCAC CATCT (SEQ ID NO: 85) | ......C............T | NA | chr6:11660928-11660950 |
| PD-1_Ex_SD_OT8 | PD-1_Ex.1_SD_OT8 Rev 1 | GTCTCGTGGGCTCGAGATGTG TATAAGAGACAGTTCAAAACACA GGGAAAACT (SEQ ID NO: 86) | CACCCACCTAAGCAC CATCT (SEQ ID NO: 85) | ......C............T | NA | chr6:11660928-11660950 |
| PD-1_Ex_SD_OT8 | PD-1_Ex.1_SD_OT8 Fwd 2 | TCGTCGGCAGCGTCAGATGTGT ATAAGAGACAGTTTCATATTGG GTGGATTGT (SEQ ID NO: 87) | CACCCACCTAAGCAC CATCT (SEQ ID NO: 85) | ......C............T | NA | chr6:11660928-11660950 |
| PD-1_Ex_SD_OT8 | PD-1_Ex.1_SD_OT8 Rev 2 | GTCTCGTGGGCTCGAGATGTG TATAAGAGACAGTTCAAAACACA GGGAAAACT (SEQ ID NO: 86) | CACCCACCTAAGCAC CATCT (SEQ ID NO: 85) | ......C............T | NA | chr6:11660928-11660950 |
| PD-1_Ex_SD_OT9 | PD-1_Ex.1_SD_OT9 Fwd 1 | TCGTCGGCAGCGTCAGATGTGT ATAAGAGACAGCAGCATCACC TGTGTAAC (SEQ ID NO: 88) | CACCTTCATCAGAACC ATCT (SEQ ID NO: 89) | .......T.A.C........T | NA | chr1:154444930-154444952 |
| PD-1_Ex_SD_OT9 | PD-1_Ex.1_SD_OT9 Rev 1 | GTCTCGTGGGCTCGAGATGTG TATAAGAGACAGGAAGTAAAAA GCAGAGGAAGC (SEQ ID NO: 90) | CACCTTCATCAGAACC ATCT (SEQ ID NO: 89) | .......T.A.C........T | NA | chr1:154444930-154444952 |
| PD-1_Ex_SD_OT9 | PD-1_Ex.1_SD_OT9 Fwd 2 | TCGTCGGCAGCGTCAGATGTGT ATAAGAGACAGCAGCATCAC CTGTGTAA (SEQ ID NO: 91) | CACCTTCATCAGAACC ATCT (SEQ ID NO: 89) | .......T.A.C........T | NA | chr1:154444930-154444952 |
| PD-1_Ex_SD_OT9 | PD-1_Ex.1_SD_OT9 Rev 2 | GTCTCGTGGGCTCGAGATGTG TATAAGAGACAGGAAGTAAAAA GCAGAGGAAGC (SEQ ID NO: 90) | CACCTTCATCAGAACC ATCT (SEQ ID NO: 89) | .......T.A.C........T | NA | chr1:154444930-154444952 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| PD-1_Ex_SD_OT10 | PD-1_Ex.1_SD_OT10_Fwd 1 | TCGTCGGCAGCGTCAGATGTGT ATAAGAGACAGTACATGTTTCT ATATGAGGCATT (SEQ ID NO: 92) | CAGCTATCTCAGAACC TTCC (SEQ ID NO: 93) | ..G...T..C...... | NA | chr5:6830623-66830645 |
| PD-1_Ex_SD_OT10 | PD-1_Ex.1_SD_OT10_Rev 1 | GTCTCGTGGGCTCGGAGATGTG TATAAGAGACAGCTTCCTCTAA GTCTCAGCTCAT (SEQ ID NO: 94) | CAGCTATCTCAGAACC TTCC (SEQ ID NO: 93) | ..G...T..C...... | NA | chr5:6830623-66830645 |
| PD-1_Ex_SD_OT10 | PD-1_Ex.1_SD_OT10_Fwd 2 | TCGTCGGCAGCGTCAGATGTGT ATAAGAGACAGTTTCTATTTTT CCATACTTTTAG (SEQ ID NO: 95) | CAGCTATCTCAGAACC TTCC (SEQ ID NO: 93) | ..G...T..C...... | NA | chr5:6830623-66830645 |
| PD-1_Ex_SD_OT10 | PD-1_Ex.1_SD_OT10_Rev 2 | GTCTCGTGGGCTCGGAGATGTG TATAAGAGACAGCCTTTCAG ATTAGTCAGG (SEQ ID NO: 96) | CAGCTATCTCAGAACC TTCC (SEQ ID NO: 93) | ..G...T..C...... | NA | chr5:6830623-66830645 |
| TRAC2_Ex.3_SA_OnT | TRAC2_Ex.3_SA_OnT_Fwd 1 | TCGTCGGCAGCGTCAGATGTGT ATAAGAGACAGTCTCAGAGCTT AGGATGCAC (SEQ ID NO: 97) | TTCGTATCTGTAAAAC CAAG (SEQ ID NO: 98) |  | NA | chr14:23019485-23019507 |
| TRAC2_Ex.3_SA_OnT | TRAC2_Ex.3_SA_OnT_Rev 1 | GTCTCGTGGGCTCGGAGATGTG TATAAGAGACAGTCTTGAAACA CAATACTGTTGG (SEQ ID NO: 99) | TTCGTATCTGTAAAAC CAAG (SEQ ID NO: 98) |  | NA | chr14:23019485-23019507 |
| TRAC2_Ex.3_SA_OnT | TRAC2_Ex.3_SA_OnT_Fwd 2 | TCGTCGGCAGCGTCAGATGTGT ATAAGAGACAGTCTCAGAGCTT AGGATGCAC (SEQ ID NO: 97) | TTCGTATCTGTAAAAC CAAG (SEQ ID NO: 98) |  | NA | chr14:23019485-23019507 |
| TRAC2_Ex.3_SA_OnT | TRAC2_Ex.3_SA_OnT_Rev 2 | GTCTCGTGGGCTCGGAGATGTG TATAAGAGACAGCTTGAAACAC AATACTGTTGG (SEQ ID NO: 100) | TTCGTATCTGTAAAAC CAAG (SEQ ID NO: 98) |  | NA | chr14:23019485-23019507 |
| TRAC2_Ex.3_SA_OT1 | TRAC2_Ex.3_SA_OT1_Fwd 1 | TCGTCGGCAGCGTCAGATGTGT ATAAGAGACAGACATACATTGC CTTACTTTGC (SEQ ID NO: 101) | TTTGGGATCTTTAAAAC CAAG (SEQ ID NO: 172) | ..G.G.....T...... | NA | chr2:15232313-15232335 |
| TRAC2_Ex.3_SA_OT1 | TRAC2_Ex.3_SA_OT1_Rev 1 | GTCTCGTGGGCTCGGAGATGTG TATAAGAGACAGTTTTGACTGC CAGAAGT (SEQ ID NO: 102) | TTTGGGATCTTTAAAAC CAAG (SEQ ID NO: 172) | ..G.G.....T...... | NA | chr2:15232313-15232335 |
| TRAC2_Ex.3_SA_OT1 | TRAC2_Ex.3_SA_OT1_Fwd 2 | TCGTCGGCAGCGTCAGATGTGT ATAAGAGACAGACATACATTGC CTTACTTTGC (SEQ ID NO: 101) | TTTGGGATCTTTAAAAC CAAG (SEQ ID NO: 172) | ..G.G.....T...... | NA | chr2:15232313-15232335 |
| TRAC2_Ex.3_SA_OT1 | TRAC2_Ex.3_SA_OT1_Rev 2 | GTCTCGTGGGCTCGGAGATGTG TATAAGAGACAGGGAAGCCAAA AGTTATACATGA (SEQ ID NO: 103) | TTTGGGATCTTTAAAAC CAAG (SEQ ID NO: 172) | ..G.G.....T...... | NA | chr2:15232313-15232335 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| TRAC2_Ex.3_SA_OT2 | TRAC2_Ex.3_SA_OT2_Fwd 1 | TCGTCGGCAGCGTCAGATGTGTATAAGAGACAGAAGTTTGGCATCTTCTTTACCT (SEQ ID NO: 104) | TGAGCATCTGTAAAACCAAG (SEQ ID NO: 105) | .GA.C............ | SYNE2 | chr14:64658071-64658093 |
| TRAC2_Ex.3_SA_OT2 | TRAC2_Ex.3_SA_OT2_Rev 1 | GTCTCGTGGGCTCGGAGATGTGTATAAGAGACAGAGTGGGGCTTCTCATCAC (SEQ ID NO: 106) | TGAGCATCTGTAAAACCAAG (SEQ ID NO: 105) | .GA.C............ | SYNE2 | chr14:64658071-64658093 |
| TRAC2_Ex.3_SA_OT2 | TRAC2_Ex.3_SA_OT2_Fwd 2 | TCGTCGGCAGCGTCAGATGTGTATAAGAGACAGAAGTTTGGCATCTTCTTTACC (SEQ ID NO: 107) | TGAGCATCTGTAAAACCAAG (SEQ ID NO: 105) | .GA.C............ | SYNE2 | chr14:64658071-64658093 |
| TRAC2_Ex.3_SA_OT2 | TRAC2_Ex.3_SA_OT2_Rev 2 | GTCTCGTGGGCTCGGAGATGTGTATAAGAGACAGAGTGGGGCTTCTCATCAC (SEQ ID NO: 106) | TGAGCATCTGTAAAACCAAG (SEQ ID NO: 105) | .GA.C............ | SYNE2 | chr14:64658071-64658093 |
| TRAC2_Ex.3_SA_OT3 | TRAC2_Ex.3_SA_OT3_Fwd 1 | TCGTCGGCAGCGTCAGATGTGTATAAGAGACAGAATGATAGATCCCAGCTGAA (SEQ ID NO: 108) | TTCTAATCTCTAAAACCAAG (SEQ ID NO: 109) | ...TA.....C........ | NA | chr11:116099208-116099230 |
| TRAC2_Ex.3_SA_OT3 | TRAC2_Ex.3_SA_OT3_Rev 1 | GTCTCGTGGGCTCGGAGATGTGTATAAGAGACAGAGCTTTCCTCCTTGCATGTATT (SEQ ID NO: 110) | TTCTAATCTCTAAAACCAAG (SEQ ID NO: 109) | ...TA.....C........ | NA | chr11:116099208-116099230 |
| TRAC2_Ex.3_SA_OT3 | TRAC2_Ex.3_SA_OT3_Fwd 2 | TCGTCGGCAGCGTCAGATGTGTATAAGAGACAGGGAGCCACAGATTAAATGAT (SEQ ID NO: 111) | TTCTAATCTCTAAAACCAAG (SEQ ID NO: 109) | ...TA.....C........ | NA | chr11:116099208-116099230 |
| TRAC2_Ex.3_SA_OT3 | TRAC2_Ex.3_SA_OT3_Rev 2 | GTCTCGTGGGCTCGGAGATGTGTATAAGAGACAGTCTTTCCTCCTTGCATGTAT (SEQ ID NO: 112) | TTCTAATCTCTAAAACCAAG (SEQ ID NO: 109) | ...TA.....C........ | NA | chr11:116099208-116099230 |
| TRAC2_Ex.3_SA_OT4 | TRAC2_Ex.3_SA_OT4_Fwd 1 | TCGTCGGCAGCGTCAGATGTGTATAAGAGACAGTCATGAATGGTGACTCAGAA (SEQ ID NO: 113) | GTGGTATCTGCAAAACCAAG (SEQ ID NO: 114) | G.G..........C..... | NA | chr3:83858142-83858164 |
| TRAC2_Ex.3_SA_OT4 | TRAC2_Ex.3_SA_OT4_Rev 1 | GTCTCGTGGGCTCGGAGATGTGTATAAGAGACAGAAATGCCAGCCACTTTTT (SEQ ID NO: 115) | GTGGTATCTGCAAAACCAAG (SEQ ID NO: 114) | G.G..........C..... | NA | chr3:83858142-83858164 |
| TRAC2_Ex.3_SA_OT4 | TRAC2_Ex.3_SA_OT4_Fwd 2 | TCGTCGGCAGCGTCAGATGTGTATAAGAGACAGAAATCATGAATGGTGACTCAG (SEQ ID NO: 116) | GTGGTATCTGCAAAACCAAG (SEQ ID NO: 114) | G.G..........C..... | NA | chr3:83858142-83858164 |
| TRAC2_Ex.3_SA_OT4 | TRAC2_Ex.3_SA_OT4_Rev 2 | GTCTCGTGGGCTCGGAGATGTGTATAAGAGACAGAAATGCCAGCCACTTTTT (SEQ ID NO: 115) | GTGGTATCTGCAAAACCAAG (SEQ ID NO: 114) | G.G..........C..... | NA | chr3:83858142-83858164 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| TRAC2_Ex.3_SA_OT5 | TRAC2_Ex.3_SA_OT5_Fwd 1 | TCGTCGGCAGCGTCAGATGTGTATAAGAGACAGGCCAAACCATATTAGCAAAC (SEQ ID NO: 117) | TCCTCATGTGTAAAACCAAG (SEQ ID NO: 118) | .C.TC..G............ | NA | chr10:33362901-33362923 |
| TRAC2_Ex.3_SA_OT5 | TRAC2_Ex.3_SA_OT5_Rev 1 | GTCTCGTGGGCTCGGAGATGTGTATAAGAGACAGTTGAGTTCATGAGAATCGTG (SEQ ID NO: 119) | TCCTCATGTGTAAAACCAAG (SEQ ID NO: 118) | .C.TC..G............ | NA | chr10:33362901-33362923 |
| TRAC2_Ex.3_SA_OT5 | TRAC2_Ex.3_SA_OT5_Fwd 2 | TCGTCGGCAGCGTCAGATGTGTATAAGAGACAGGCCAAACCATATTAGCAAAC (SEQ ID NO: 117) | TCCTCATGTGTAAAACCAAG (SEQ ID NO: 118) | .C.TC..G............ | NA | chr10:33362901-33362923 |
| TRAC2_Ex.3_SA_OT5 | TRAC2_Ex.3_SA_OT5_Rev 2 | GTCTCGTGGGCTCGGAGATGTGTATAAGAGACAGATTGAGTTCATGAGAATCGTG (SEQ ID NO: 120) | TCCTCATGTGTAAAACCAAG (SEQ ID NO: 118) | .C.TC..G............ | NA | chr10:33362901-33362923 |
| TRAC2_Ex.3_SA_OT6 | TRAC2_Ex.3_SA_OT6_Fwd 1 | TCGTCGGCAGCGTCAGATGTGTATAAGAGACAGGCCAAACGTACACTGTAATGC (SEQ ID NO: 121) | TCTGCATCTTTAAAACCAAG (SEQ ID NO: 122) | .CT.C.....T......... | GRIA1 | chr5:153014461-153014483 |
| TRAC2_Ex.3_SA_OT6 | TRAC2_Ex.3_SA_OT6_Rev 1 | GTCTCGTGGGCTCGGAGATGTGTATAAGAGACAGGCTTTGCTGAGACCATAGAT (SEQ ID NO: 123) | TCTGCATCTTTAAAACCAAG (SEQ ID NO: 122) | .CT.C.....T......... | GRIA1 | chr5:153014461-153014483 |
| TRAC2_Ex.3_SA_OT6 | TRAC2_Ex.3_SA_OT6_Fwd 2 | TCGTCGGCAGCGTCAGATGTGTATAAGAGACAGGCCAAACGTACACTGTAATGC (SEQ ID NO: 121) | TCTGCATCTTTAAAACCAAG (SEQ ID NO: 122) | .CT.C.....T......... | GRIA1 | chr5:153014461-153014483 |
| TRAC2_Ex.3_SA_OT6 | TRAC2_Ex.3_SA_OT6_Rev 2 | GTCTCGTGGGCTCGGAGATGTGTATAAGAGACAGATGCTTTGCTGAGACCATAG (SEQ ID NO: 124) | TCTGCATCTTTAAAACCAAG (SEQ ID NO: 122) | .CT.C.....T......... | GRIA1 | chr5:153014461-153014483 |
| TRAC2_Ex.3_SA_OT7 | TRAC2_Ex.3_SA_OT7_Fwd 1 | TCGTCGGCAGCGTCAGATGTGTATAAGAGACAGCAAGTGCTGGGATTACAGA (SEQ ID NO: 125) | TTTGTATCTTTAAAACCATG (SEQ ID NO: 126) | ..T.......T......T.. | TOPBP1 | chr3:133341480-133341502 |
| TRAC2_Ex.3_SA_OT7 | TRAC2_Ex.3_SA_OT7_Rev 1 | GTCTCGTGGGCTCGGAGATGTGTATAAGAGACAGTGCAAAGTTTTATGTAGTTTAAGTG (SEQ ID NO: 127) | TTTGTATCTTTAAAACCATG (SEQ ID NO: 126) | ..T.......T......T.. | TOPBP1 | chr3:133341480-133341502 |
| TRAC2_Ex.3_SA_OT7 | TRAC2_Ex.3_SA_OT7_Fwd 2 | TCGTCGGCAGCGTCAGATGTGTATAAGAGACAGCAAGTGCTGGGATTACAGA (SEQ ID NO: 125) | TTTGTATCTTTAAAACCATG (SEQ ID NO: 126) | ..T.......T......T.. | TOPBP1 | chr3:133341480-133341502 |
| TRAC2_Ex.3_SA_OT7 | TRAC2_Ex.3_SA_OT7_Rev 2 | GTCTCGTGGGCTCGGAGATGTGTATAAGAGACAGAATTTGCAAAGTTTTATGTAGTT (SEQ ID NO: 128) | TTTGTATCTTTAAAACCATG (SEQ ID NO: 126) | ..T.......T......T.. | TOPBP1 | chr3:133341480-133341502 |

TABLE 2-continued

Computationally predicted candidate off-target sites

| Site Name | Primer Name | Primer Sequence | Off-Target Sequence | Alignment | Gene | Coordinates |
|---|---|---|---|---|---|---|
| TRAC2_Ex.3_SA_OT8 | TRAC2_Ex.3_SA_OT8_Fwd 1 | TCGTCGGCAGCGTCAGATGTGT ATAAGAGACAGTGGGACTCTTG GTTCTGTAT (SEQ ID NO: 129) | TTCTTATGTGTAAAAC CAAG (SEQ ID NO: 130) | ....T...G....G........ | NTNG1 | chr1:107907252-107907274 |
| TRAC2_Ex.3_SA_OT8 | TRAC2_Ex.3_SA_OT8_Rev 1 | GTCTCGTGGGCTCGAGATGTG TATAAGAGACAGTTTTTGTTGTT GTTTTACTTGAA (SEQ ID NO: 131) | TTCTTATGTGTAAAAC CAAG (SEQ ID NO: 130) | ....T...G....G........ | NTNG1 | chr1:107907252-107907274 |
| TRAC2_Ex.3_SA_OT8 | TRAC2_Ex.3_SA_OT8_Fwd 2 | TCGTCGGCAGCGTCAGATGTGT ATAAGAGACAGTGGGACTCTT GGTTCTGTA (SEQ ID NO: 132) | TTCTTATGTGTAAAAC CAAG (SEQ ID NO: 130) | ....T...G....G........ | NTNG1 | chr1:107907252-107907274 |
| TRAC2_Ex.3_SA_OT8 | TRAC2_Ex.3_SA_OT8_Rev 2 | GTCTCGTGGGCTCGAGATGTG TATAAGAGACAGTTTTTGTTGTT GTTTTACTTGAA (SEQ ID NO: 131) | TTCTTATGTGTAAAAC CAAG (SEQ ID NO: 130) | ....T...G....G........ | NTNG1 | chr1:107907252-107907274 |
| TRAC2_Ex.3_SA_OT9 | TRAC2_Ex.3_SA_OT9_Fwd 1 | TCGTCGGCAGCGTCAGATGTGT ATAAGAGACAGAAATTCTTCTTG GGCTCAG (SEQ ID NO: 133) | CTCTCTTCTGTAAAAC CAAG (SEQ ID NO: 134) | C...TCT............... | KCNQ5 | chr6:73675659-73675681 |
| TRAC2_Ex.3_SA_OT9 | TRAC2_Ex.3_SA_OT9_Rev 1 | GTCTCGTGGGCTCGAGATGTG TATAAGAGACAGGCTCATTACT GGGTTAAGCA (SEQ ID NO: 135) | CTCTCTTCTGTAAAAC CAAG (SEQ ID NO: 134) | C...TCT............... | KCNQ5 | chr6:73675659-73675681 |
| TRAC2_Ex.3_SA_OT9 | TRAC2_Ex.3_SA_OT9_Fwd 2 | TCGTCGGCAGCGTCAGATGTGT ATAAGAGACAGAAATTCTTCTT GGGCTCAG (SEQ ID NO: 136) | CTCTCTTCTGTAAAAC CAAG (SEQ ID NO: 134) | C...TCT............... | KCNQ5 | chr6:73675659-73675681 |
| TRAC2_Ex.3_SA_OT9 | TRAC2_Ex.3_SA_OT9_Rev 2 | GTCTCGTGGGCTCGAGATGTG TATAAGAGACAGGCTCATTACT GGGTTAAGCA (SEQ ID NO: 135) | CTCTCTTCTGTAAAAC CAAG (SEQ ID NO: 134) | C...TCT............... | KCNQ5 | chr6:73675659-73675681 |
| TRAC2_Ex.3_SA_OT10 | TRAC2_Ex.3_SA_OT10_Fwd 1 | TCGTCGGCAGCGTCAGATGTGT ATAAGAGACAGTCTAGGCTCTT GACACCATC (SEQ ID NO: 137) | TGGGTTTCTTTAAAAC CAAG (SEQ ID NO: 138) | .GG...T...T........... | FSHR | chr2:49345982-49346004 |
| TRAC2_Ex.3_SA_OT10 | TRAC2_Ex.3_SA_OT10_Rev 1 | GTCTCGTGGGCTCGAGATGTG TATAAGAGACAGGAACAACTAG ACCCAATGTGA (SEQ ID NO: 139) | TGGGTTTCTTTAAAAC CAAG (SEQ ID NO: 138) | .GG...T...T........... | FSHR | chr2:49345982-49346004 |
| TRAC2_Ex.3_SA_OT10 | TRAC2_Ex.3_SA_OT10_Fwd 2 | TCGTCGGCAGCGTCAGATGTGT ATAAGAGACAGGTCTAGGCTCT TGACACCAT (SEQ ID NO: 140) | TGGGTTTCTTTAAAAC CAAG (SEQ ID NO: 138) | .GG...T...T........... | FSHR | chr2:49345982-49346004 |
| TRAC2_Ex.3_SA_OT10 | TRAC2_Ex.3_SA_OT10_Rev 2 | GTCTCGTGGGCTCGAGATGTG TATAAGAGACAGGAACAACTAG ACCCAATGTGA (SEQ ID NO: 139) | TGGGTTTCTTTAAAAC CAAG (SEQ ID NO: 138) | .GG...T...T........... | FSHR | chr2:49345982-49346004 |

Figure 5A:
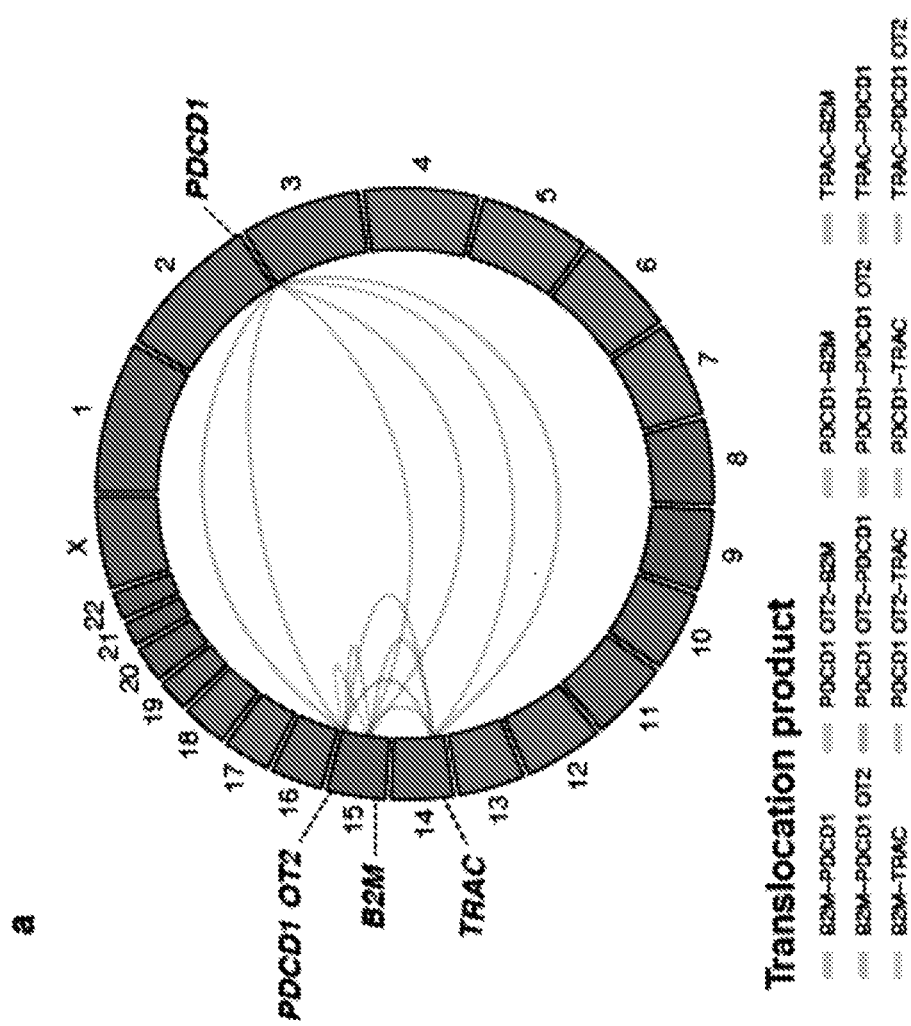
FIGS. 5A-5B demonstrate translocation frequencies in multiplex edited T cells. (a) Circos plot of possible translocation outcomes resulting from double strand break induction at TRAC, B2M, PDCD1, and PDCD1 OT site. (b) Droplet digital PCR quantification of translocation frequencies. All assays run in technical duplicate across n=2 independent biological T cell donors.
Figure 5B:
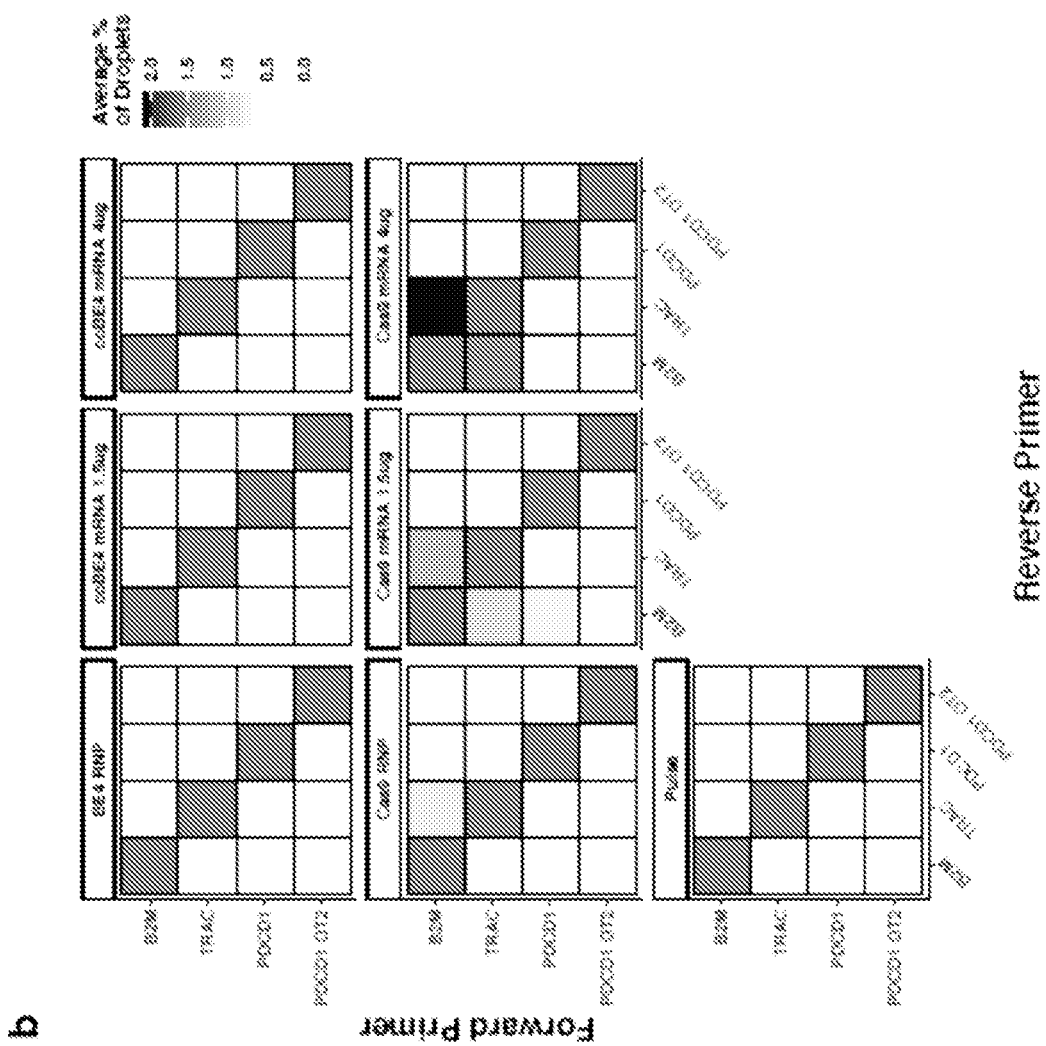
Figure 13:
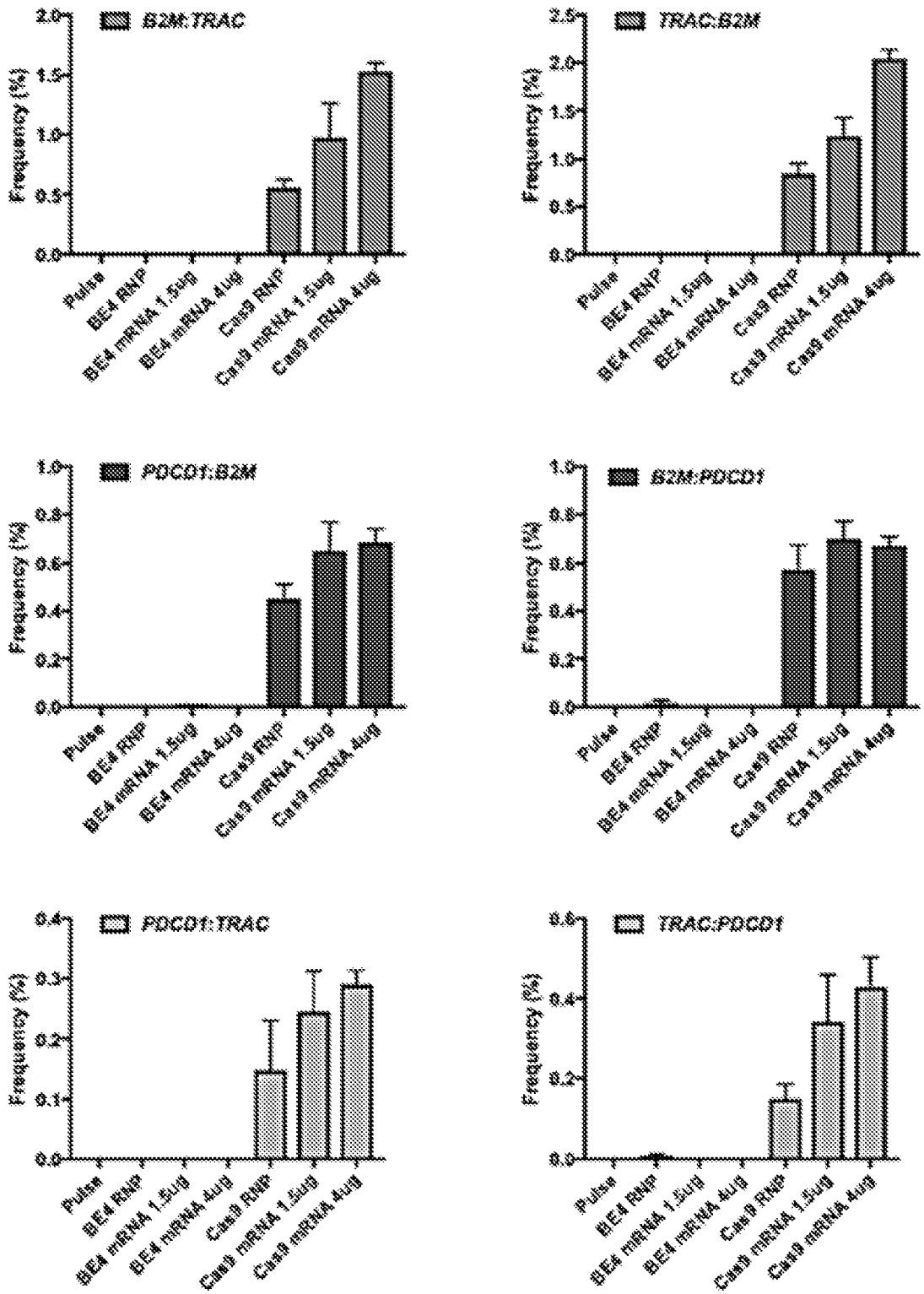
FIG. 13 demonstrates translocation frequency between three target loci. Droplet digital PCR quantification of translocation frequency between TRAC, B2M, and PDCD1 after delivery of three sgRNA and spCas9 protein, spCas9 mRNA, BE4 protein, or coBE4 mRNA. n=2 independent T cell donors assayed in duplicate.
Figure 14:
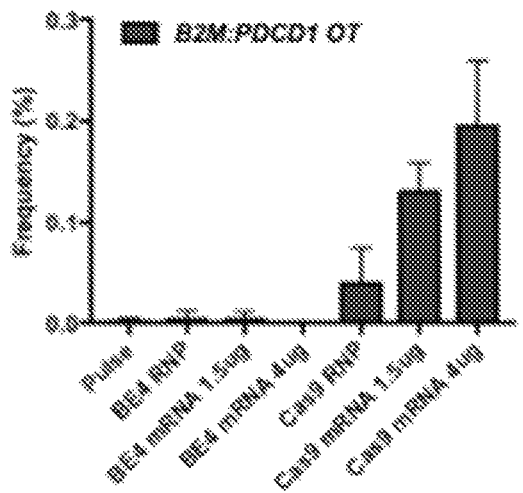
FIG. 14 demonstrates translocation frequency between target loci and PDCD1 off-target site. Droplet digital PCR quantification of translocation frequency between PDCD1 OT site and TRAC, B2M, and PDCD1 after delivery of three sgRNA and spCas9 protein, spCas9 mRNA, BE4 protein, or coBE4 mRNA. n=2 independent T cell donors assayed in duplicate.
Figure 14:
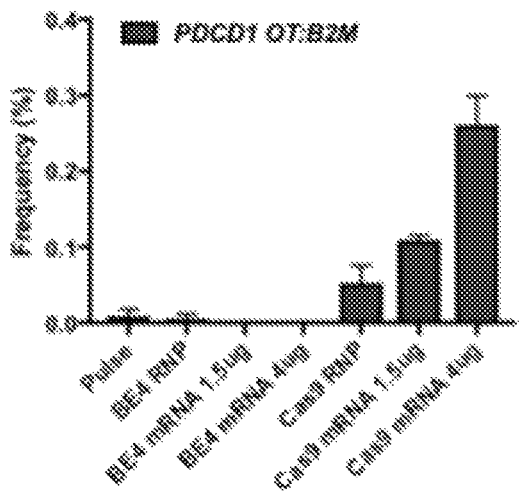
Figure 14:
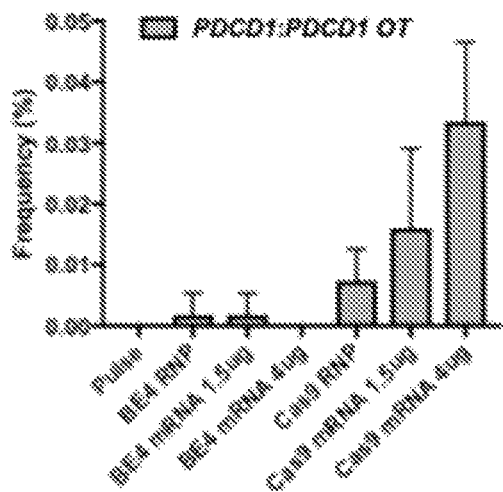
Figure 14:
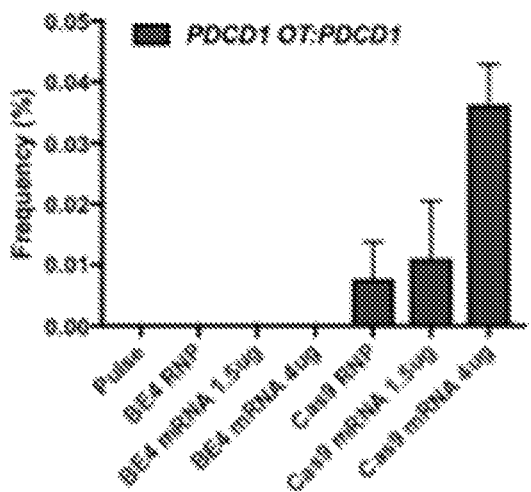
Figure 14:
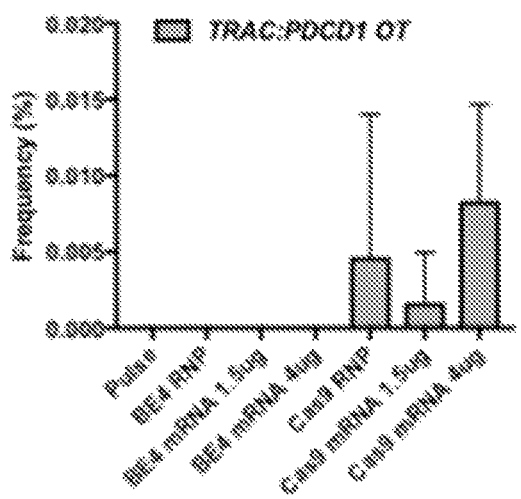
Figure 14:
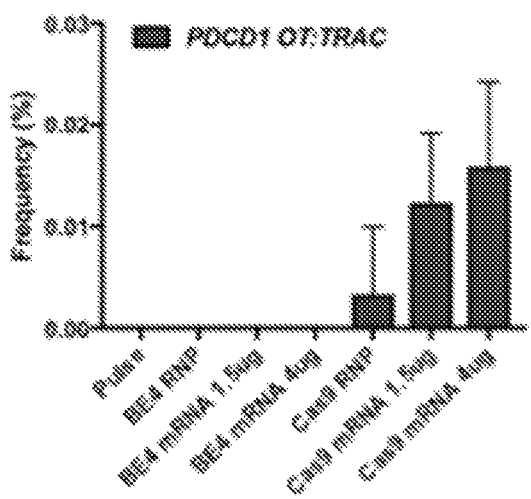

Nuclease-mediated multiplex editing has also been reported to generate undesired translocations in human T cells[3]. As base editing substantially reduces the frequency of DSB formation, we reasoned that translocations should likewise be reduced using our base editing approach. To test our hypothesis, we used droplet digital PCR (ddPCR) to quantify the frequency of twelve possible translocation outcomes predicted to occur between our three target loci and the single identified OT site (FIG. 5A). Following co-delivery of our three optimal sgRNA with either SpCas9 nuclease RNP or mRNA, we were able to detect all 12 predicted translocation outcomes at varying frequencies (FIG. 5B, FIGS. 13-14). In all cases, SpCas9 mRNA resulted in the highest rate of translocation, with translocations between TRAC and B2M being most frequent (2.04±0.09%) (FIG. 5B). In stark contrast, translocation outcomes between our three target loci were virtually undetectable in cell populations receiving BE4 RNP or either dose of coBE4 mRNA with our optimal sgRNAs (FIG. 5B, FIG. 13). In a single replicate from one donor, the PDCD1:B2M assay gave rise to two positive droplets with low-dose coBE4 mRNA (calculated frequency=0.003±0.006%). Because no positive droplets were detected with BE4 RNP or high-dose coBE4 mRNA, these may be artifactual (FIG. 13). Translocations between our three target loci and the single identified OT site were also detected in SpCas9 treated T cells, albeit at lower frequency, while BE4 treated samples showed no signals above the detection limit (0.01%) of our assay (FIG. 5B, FIG. 14).

Figure 6A:
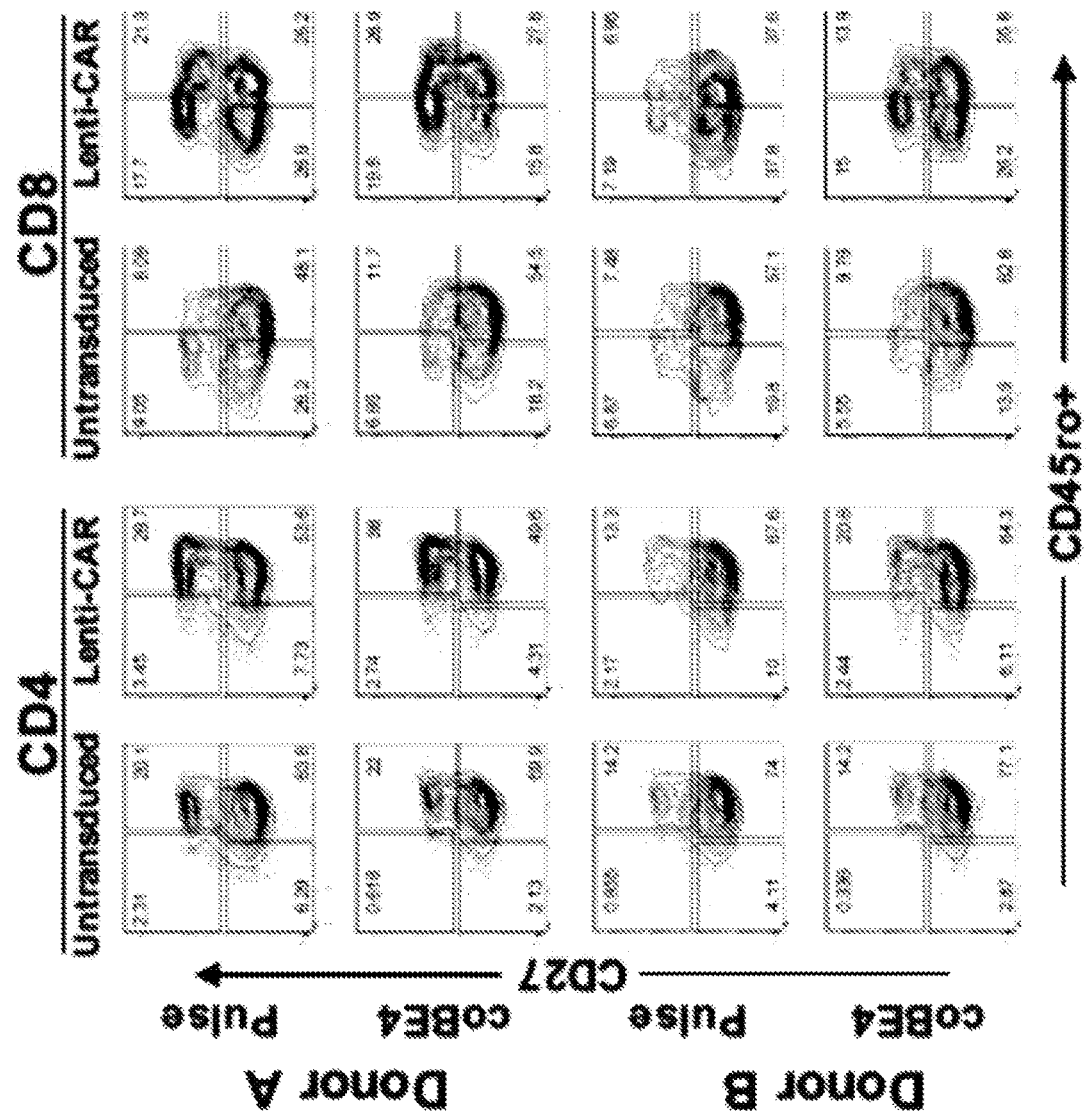
FIGS. 6A-6D demonstrate function of multiplex edited T cells. (a) Expression of the memory marker CD27 and CD45ro following editing and expansion. Production of cytokines individually (b) and in combination (c) by CD4 and CD8 T cells following activation. (d) Ability of T cells to kill CD19neg K562, CD19pos Raji cells, or CD19pos/PD-L1pos Raji cells as measured by luciferase luminescence assay following co-culture with T cells. Graph titles indicate E:T ratio. Data represented as mean±SD, with assays run in triplicate in two independent biological T cell donors. (n.s. P>0.05, * P≤0.05,  P≤0.01, * P≤0.001, **** P≤0.0001).
Figure 6B:
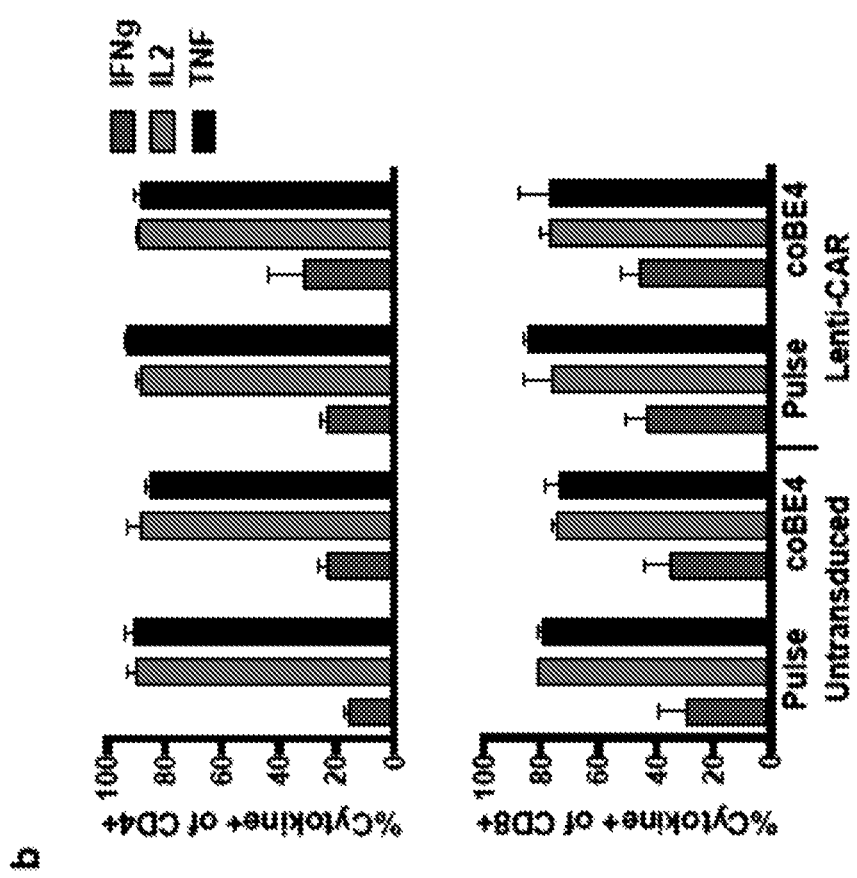
Figure 6C:
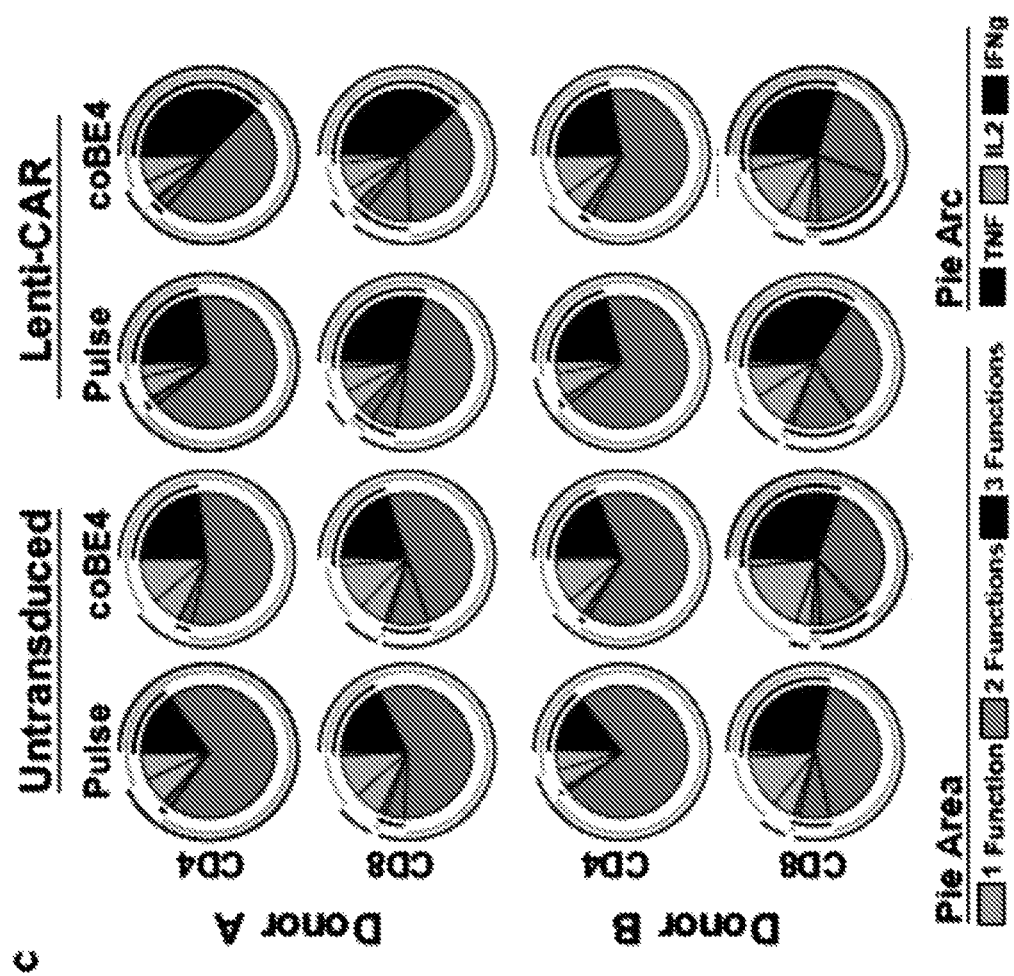
Figure 6D:
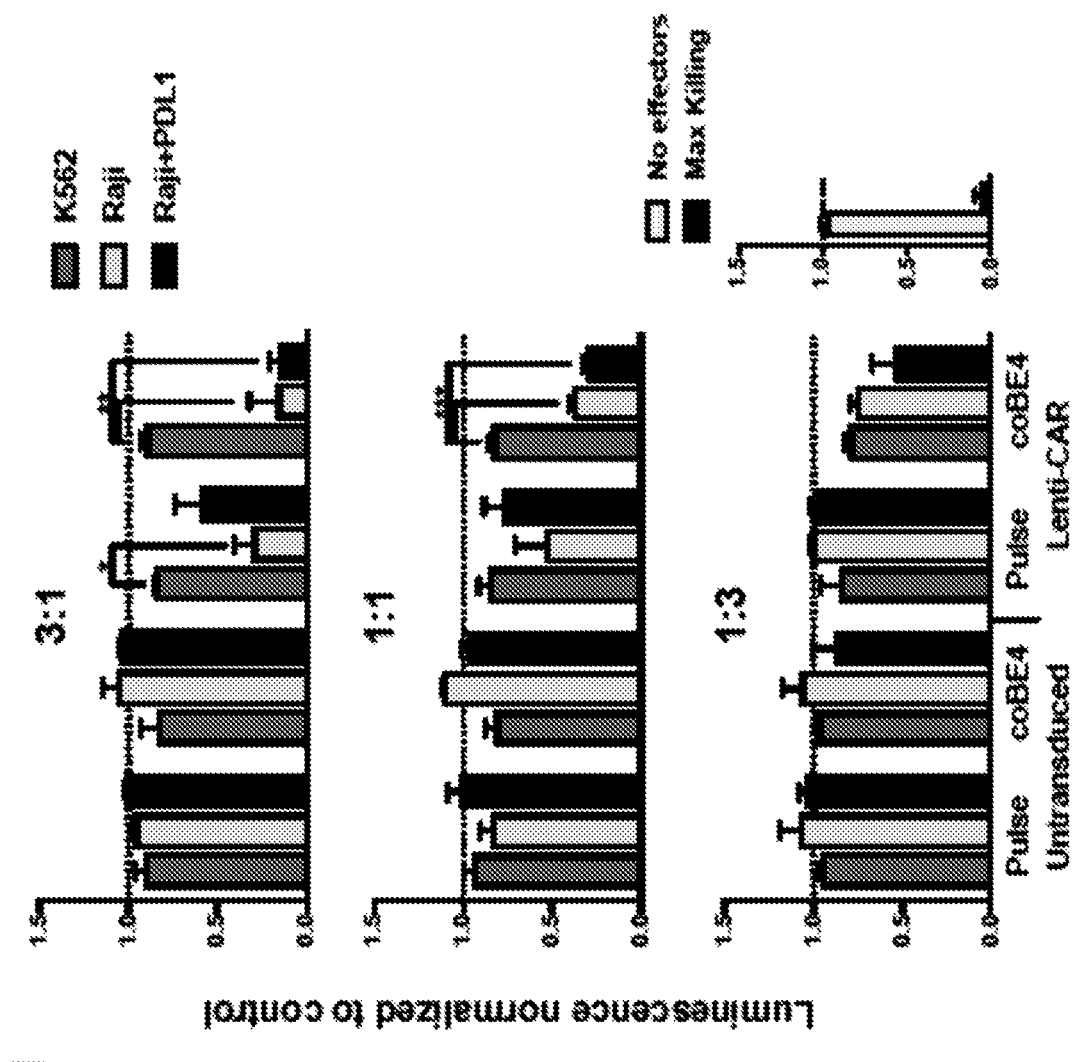
Figure 15A:
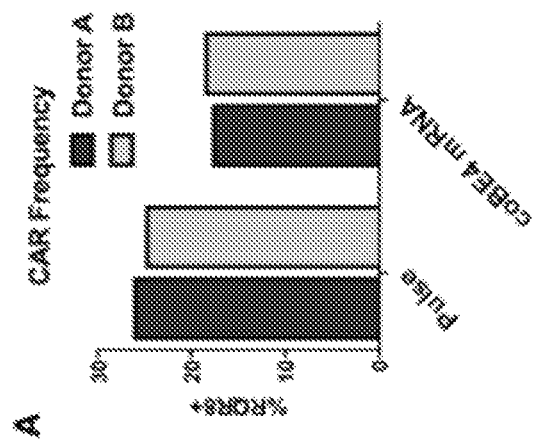
FIGS. 15A-15B demonstrate CAR transduction and T cell expansion efficiency. (A.) Bar graph depicting the frequency of transduced T cells using the MND-CD19 CAR-RQR8 lentiviral vectors, MOI of 20, via staining for RQR8 in two independent donors. RQR8 is a hybrid molecule containing domains for staining with CD34 and CD20 specific antibody and serves as a surrogate for determining CAR positive T cell frequency. (B.) Bar graphs depicting the number of viable cells at day 5 and 12 post electroporation and transduction. n=2 independent donors.
Figure 15B:
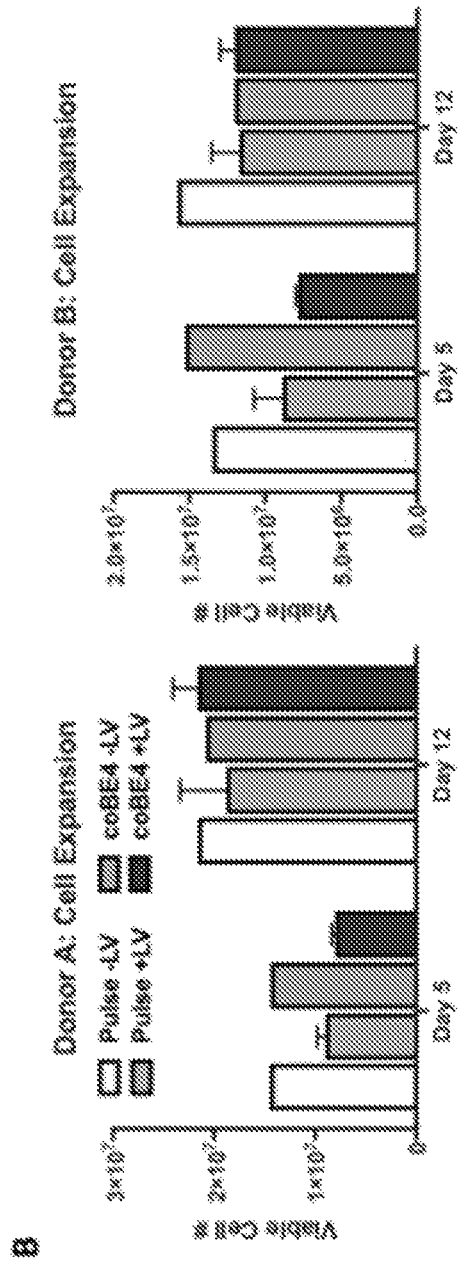

We next sought to determine whether multiplex knockout T cells generated using our base editing strategy retain cytokine functionality and are capable of mediating target cell killing when equipped with a CAR. We performed phenotypic evaluation of both electroporation pulse control and coBE4 knockout T cells with and without a CD19-specific CAR by analyzing markers of differentiation[27]. Both untransduced and CAR-transduced T cells exhibited similar differentiation phenotypes, with the fractions of effector and memory populations similar between control and coBE4 knockout T cells (FIG. 6A). CAR transduction and cell expansion were also comparable between pulse and coBE4 mRNA groups (FIGS. 15A-15B). Following activation, a high frequency of both untransduced and CAR-transduced coBE4 knockout T cells exhibited robust production of cytokines IL-2, TNFα, and IFNγ (FIG. 6B). Cytokine polyfunctionality was similarly retained following the multiplex editing process (FIG. 6C). Collectively, these data demonstrate that multiplex coBE4 editing combined with CAR transduction did not negatively impact T cell phenotype or function. Finally, to determine if coBE4 knockout T cells equipped with the CD19 CAR retained the ability to kill target cells, we conducted in vitro co-culture assays with non-target CD19$^{neg}$/PD-L1$^{neg}$ K562; target CD19$^{pos}$/PD-L1$^{neg}$ Raji; and target CD19$^{pos}$/PD-L1$^{pos}$ Raji engineered to overexpress PD-L1, which would normally act to inhibit killing by T cells expressing cell surface PD-1. Both control and coBE4 knockout T cells mediated specific killing of CD19$^{pos}$ but not CD19$^{neg}$ target cells (FIG. 6D). However, only coBE4 knockout T cells were able to achieve significant killing of CD19$^{pos}$/PD-L1$^{pos}$ target cells, with the efficiency of killing equivalent to that of CD19$^{pos}$/PD-L1$^{neg}$ g target cells (FIG. 6D).

As we come to better understand the requirements for successful cell-based immunotherapy and gene therapy, and as enthusiasm grows for the production of universal, allogeneic cells, highly multiplexed gene editing will likely become more commonplace. However, it has been well documented that DSBs are toxic lesions that can drive genomic instability and cell death[11, 12]. This is a lesser concern when engineering cells for research but could lead to transformation or reduced function when gene editing cells for therapeutic use. Our concerns surrounding DSBs are further heightened in the context of multiplex gene editing where multiple, simultaneous DSBs can compound toxicity. This is highlighted by the parabolic relationship between the number of discrete DSB sites and potential translocation outcomes, such that an editing strategy targeting 10 loci could generate 90 potential translocations, not accounting for other potential genomic alterations such as inversions and large deletions. To overcome these issues, we have implemented the use of base editor technology for multiplex T cell engineering and demonstrate that splice site disruption through base editing offers an efficient and safer approach compared to the use of DSB-inducing targeted nucleases.

Interestingly, we find both higher rates of non-target editing and indel formation when using BE4 RNP compared to coBE4 expressed from transfected mRNA. This observation may be due to the extended BE4 residence time achieved when expressed at high levels from a stable mRNA as opposed to direct BE4 protein delivery. As even free UGI has been shown to reduce both indel frequency and non-target editing in the context of BE3[28], the extended residence time achieved by mRNA delivery may allow BE4 UGI domains additional capacity to mitigate DSB formation and non-target editing[28].

In our current study we utilized lentiviral delivery of CD19-specific CAR, which is the current industry standard in CAR-T therapy. However, this approach has many drawbacks, including the risk of insertional mutagenesis, variable CAR expression, and gene silencing[29-31]. To overcome these issues, a number of groups have demonstrated high efficiency, site-specific integration using Cas9 nuclease along with rAAV-delivered DNA donor templates for homologous recombination (HR). This raises the possibility that BE4 could be deployed to safely and efficiently knock-out multiple genes with simultaneous introduction of therapeutic transgenes in a site-specific fashion using rAAV and Cas9 orthologs, such as *Staphylococcus aureus* Cas9 (SaCas9) or *Francisella novella* Cas9 (FnCas9)[32, 33]. The application of Cas9 orthologs would allow for simultaneous use of distinct sgRNAs specific to BE4 and Cas9 nuclease without concerns of cross-utilization. Alternatively, it has been demonstrated that a DNA nick can be used to stimulate HR using naked DNA or rAAV as a DNA donor molecule, albeit with lower efficiency[34]. This provocatively highlights the potential of BE4 to mediate gene knockout through deaminase activity, while simultaneously mediating HR through its nickase function. In this scenario, the sgRNA binding sites may require an absence of cytosines within the base editing window to prevent loss of Cas9 binding due to sequence changes through C to T conversion.

One notable difference between the use of base editors and targeted nucleases is the number of potential outcomes from the editing event. Nuclease-mediated DSBs are repaired through the highly variable non-homologous end joining (NHEJ) pathway, resulting in a spectrum of indels; some of which will not introduce frame-shift mutations and will thus have unknown significance to gene expression and function. Alternatively, our base editing approach has a limited number of outcomes, all resulting in the loss of function of the native splice donor or acceptor, even when considering non-target editing. Yet it is important to consider that disruption of the native splice site may not always result in a nonfunctional product, given that alternative or cryptic splicing could maintain the biological function of a gene.

Figures 17A, 17B:
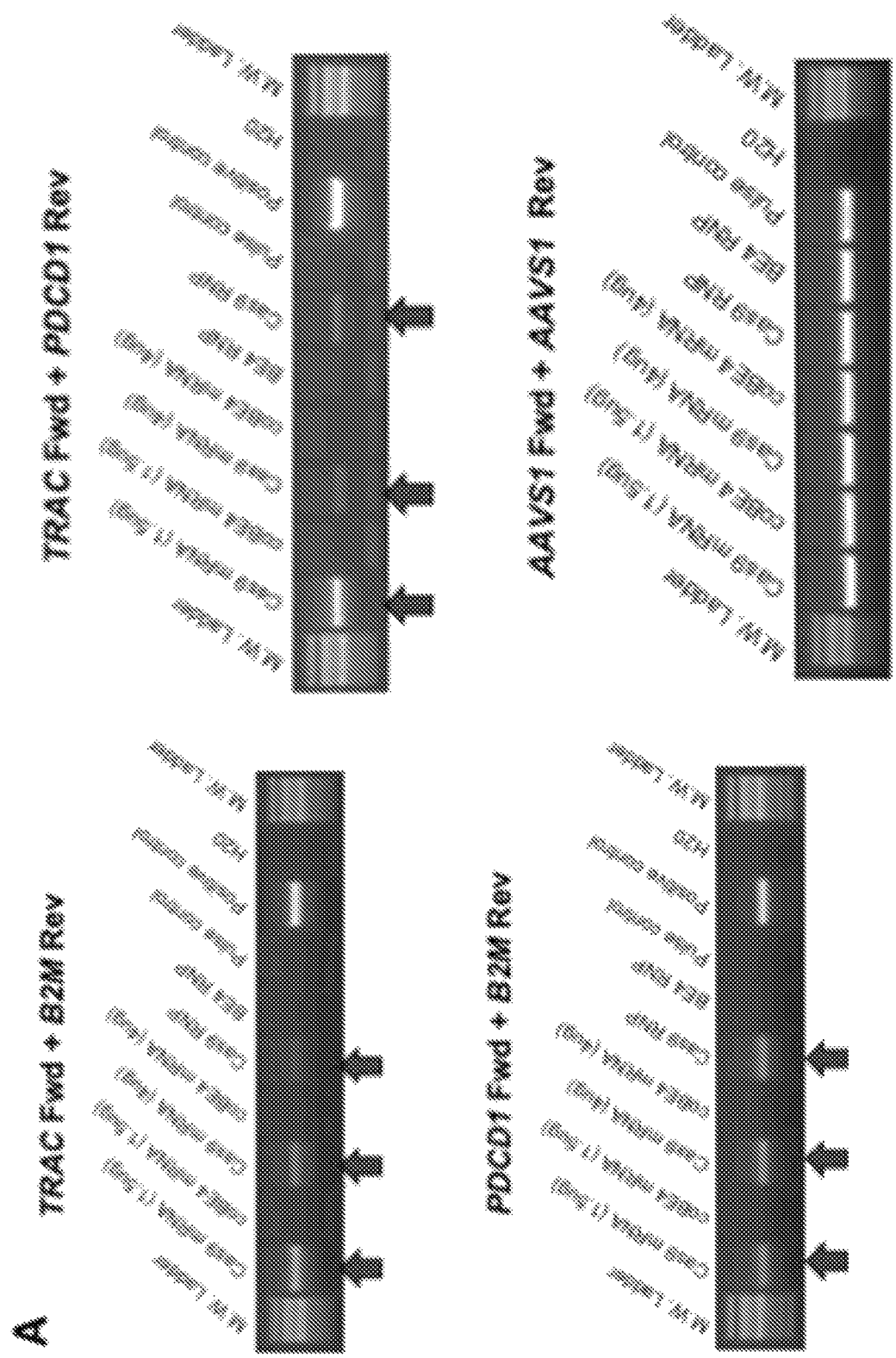
FIGS. 17A-17B demonstrate sequencing of sub-cloned PCR products spanning translocation junctions. (A) Results of translocation PCR performed between the noted target genes using Cas9 or BE mRNA or protein, as noted. An AAVS1 control PCR was also performed to confirm gDNA quality and functionality for PCR. (B) PCR products from (A) were TA cloned into TOPO plasmids and subsequently analyzed via Sanger sequencing. Resultant chromatograms were then aligned to a hypothetical 'perfect' junction sequence between the noted target gene gRNA cut sites and aligned. Also depicted are ddPCR probes used to generate the data.
Figures 18A, 18B, 18C, 18D:
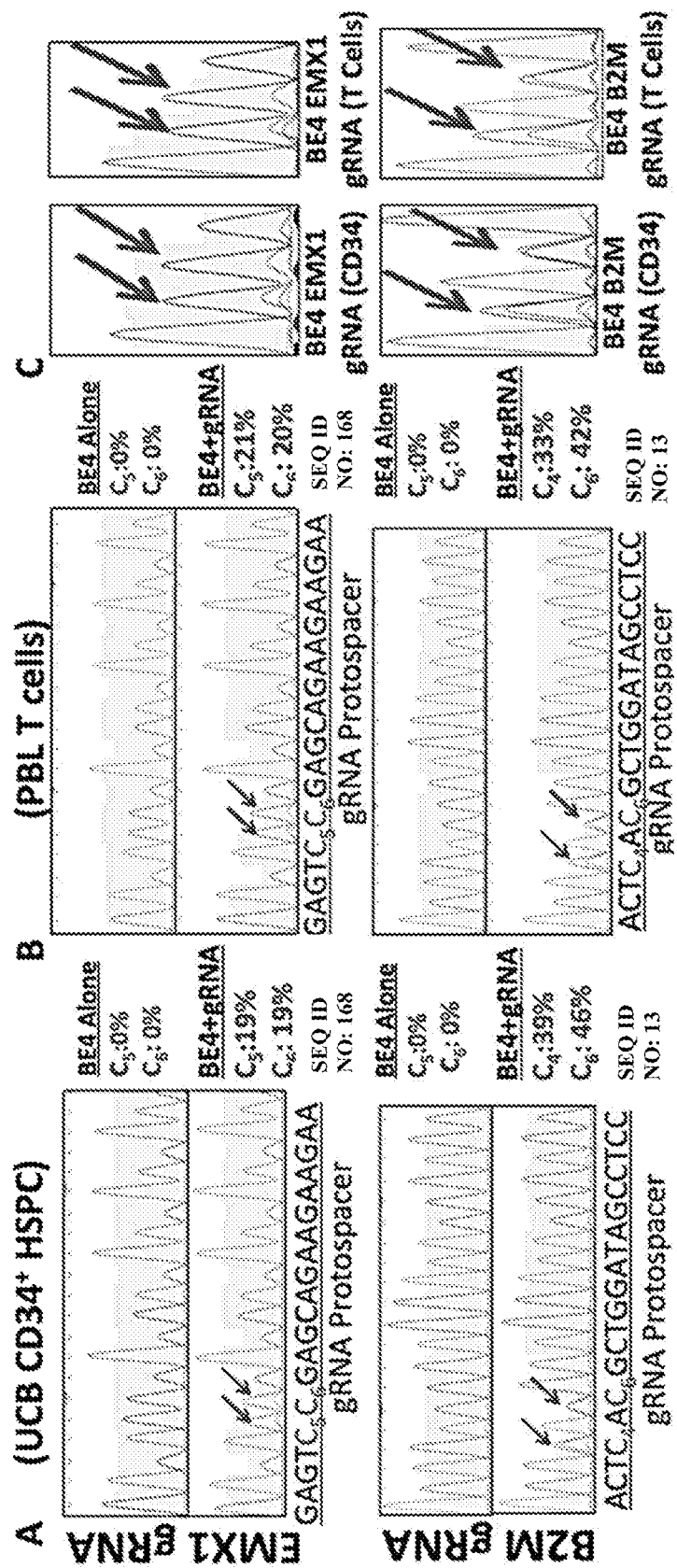
FIGS. 18A-18C demonstrate highly efficient base editing in expanded, activated UCB CD34+ HSPCs. C to T conversion was calculated using EditR.
Figure 19:
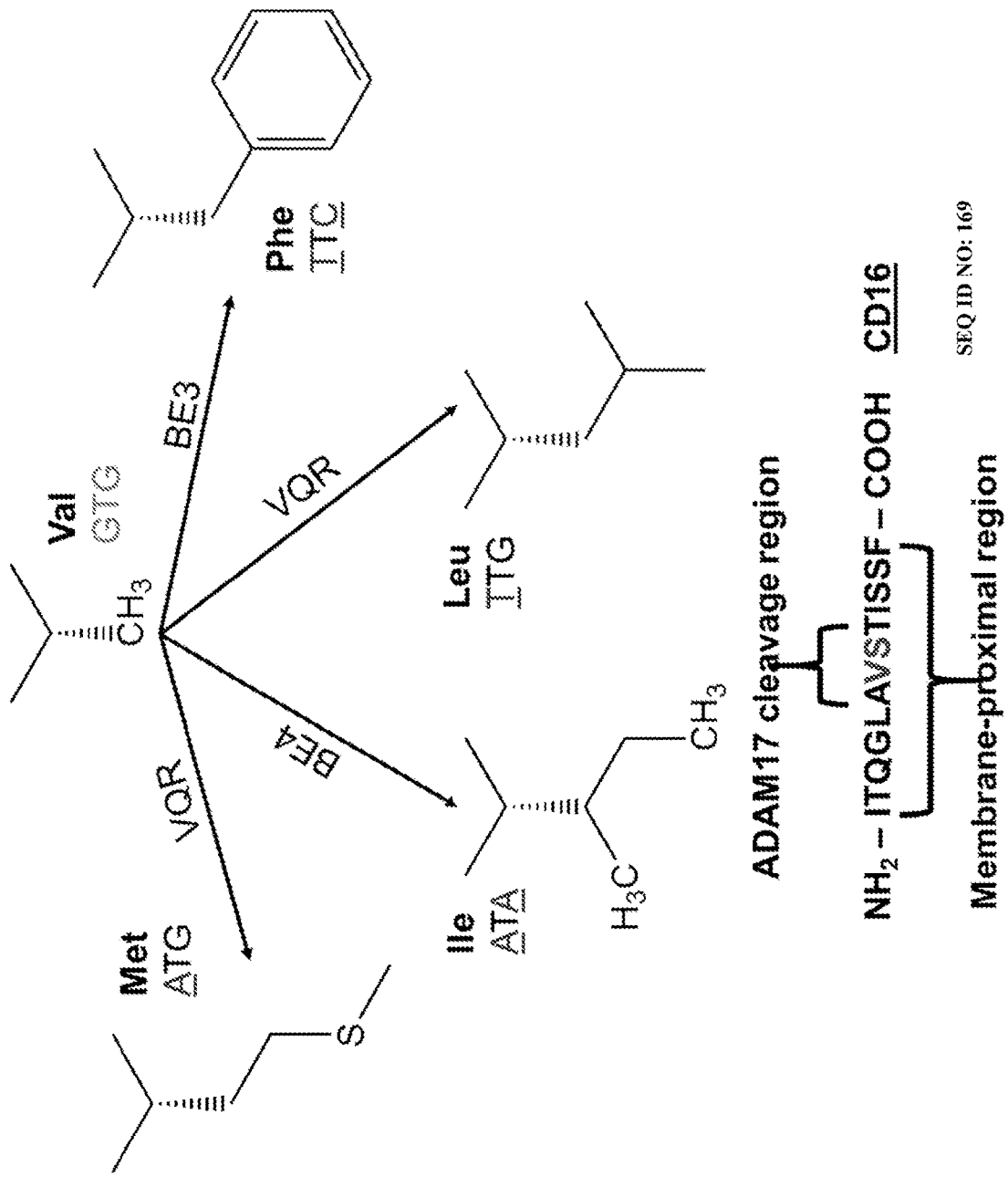
FIG. 19 shows the previously-identified ADAM17 cleavage region in CD16, with a critical serine (red) which, when mutated to a proline, renders CD16 non-cleavable by ADAM17. Using C-T base editor variants, we were able to target the adjacent valine (blue). The possible amino acid changes to this valine achievable using C-T base editor variants are shown.
Figure 20A:
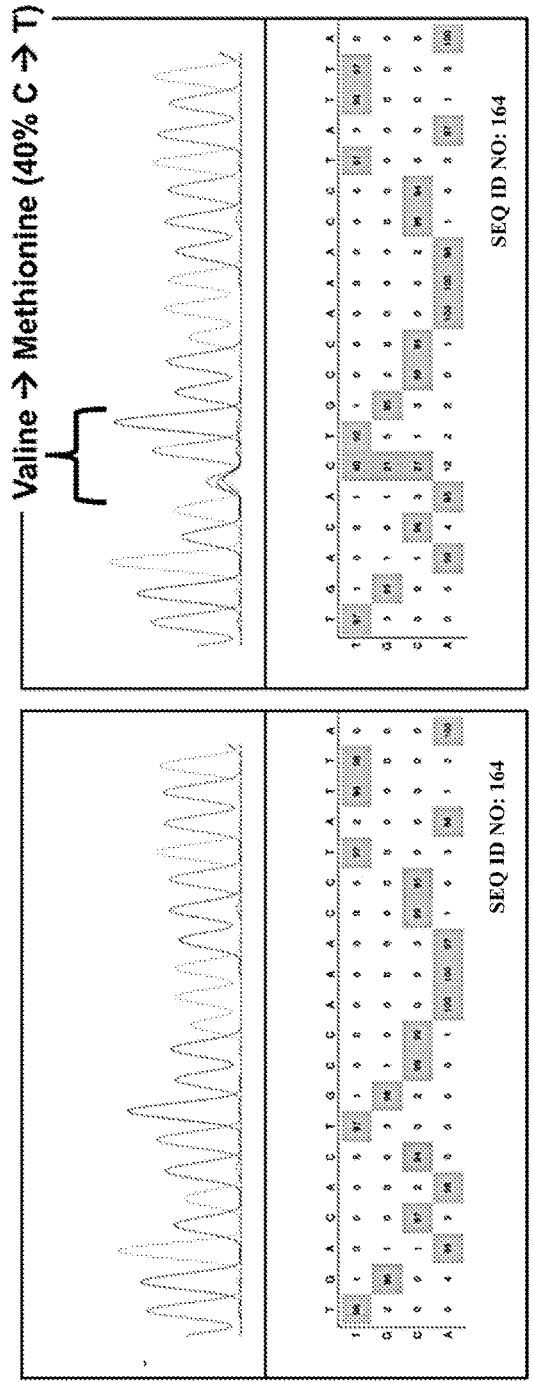
FIGS. 20A-20B shows representative Sanger sequencing chromatograms. (A) shows sequencing chromatograms from control (BE3-VQR alone) and edited (BE3-VQR+ CD16 gRNA) samples (top). C to T conversion was calculated using EditR. Results from two separate donors were combined in the bar graph (bottom). (B) shows sequencing chromatograms from control (ABE alone) and edited (ABE+ CD16a gRNA) samples. T to C conversion was calculated using EditR. ABE+CD16a gRNA sample demonstrates conversion to cleavage resistant CD16a variant.
Figure 20B:
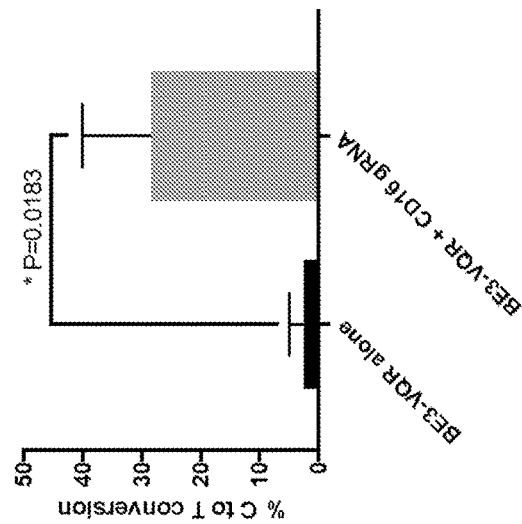
Figures 20A, 20B:
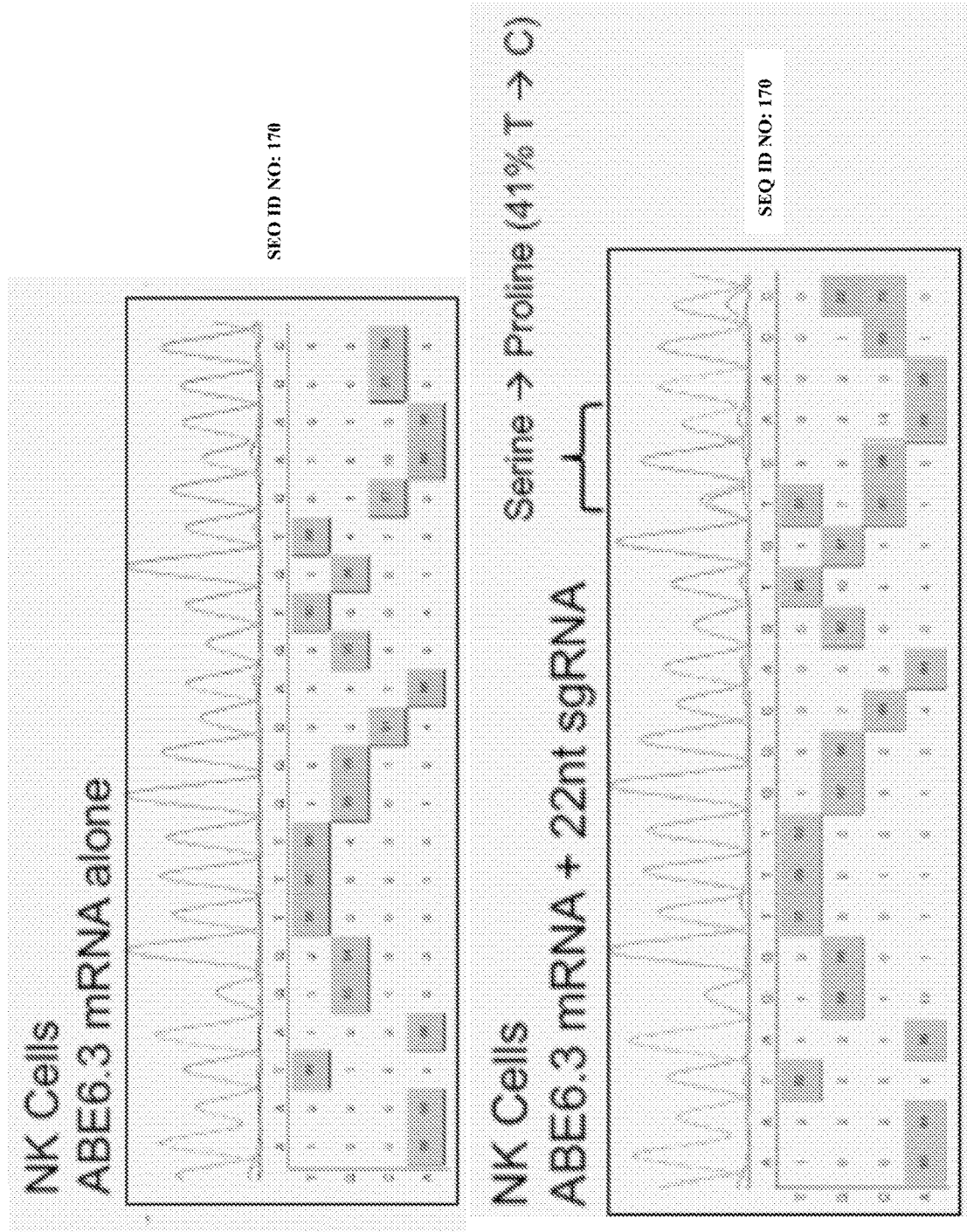

Translocation analysis using small ddPCR amplicons (>200 bp) spanning the sgRNA target site demonstrated that base editing with optimal reagents virtually eliminates detectable translocations, whereas Cas9 nuclease produces numerous translocations, some at frequencies as high as 1.5%. Notably, larger deletions were also identified at the site of translocation through Sanger sequencing of subcloned junction PCR amplicons (~500 bp) from SpCas9-treated cells (FIGS. 17A-17B). These data suggest the presence of more complex genomic rearrangements similar to those reported previously[9,10] that are not detected by our current ddPCR assays. Considering the variability in efficiency of nucleic acid delivery between cells by electroporation, it is possible that cells receiving high levels of SpCas9/sgRNA may harbor translocations more frequently.

Although we demonstrate that BE4 substantially reduces DSB induction compared to SpCas9 nuclease and does not produce detectable translocations, the potential remains for undesirable events to occur. For instance, it is possible that the rAPOBEC1 of BE4 could non-specifically edit cytosines in single-stranded DNA during DNA replication[35]. Additionally, the UGIs of BE4 could potentially inhibit uracil DNA glycosylases in a nonspecific fashion, thereby hindering base excision repair of naturally and frequently occurring cytosine deamination in normal mammalian cells[36]. Further studies investigating these potential events should be undertaken prior to clinical translation of base edited cells, though it may be challenging to definitively document such unintended occurrences. Despite these areas of uncertainty, the base editor platform represents a novel approach for highly efficient multiplex engineering of therapeutic primary cells with an improved safety profile compared to current nuclease technologies.

Methods

Cloning & Viral Production: DNA sequences for CD19 chimeric antigen receptor linked by a T2A to RQR8 were synthesized as gBlock Gene Fragments (Integrated DNA Technologies [IDT]). Fragments were Gibson Assembled[37] into pRRL (available at www.addgene.org/36247 on the World Wide Web). Gibson reactions were transformed into DH10β E. coli and plated on LB agar with ampicillin. Plasmid DNA was purified from colonies using the GeneJET Plasmid Miniprep Kit (ThermoFisher). Following confirmation by Sanger sequencing, clones were sent to the University of Minnesota Viral Vector & Cloning Core (VVCC) for production and titration of viral particles.

Guide RNA Design: Guide RNAs (sgRNAs) were designed using the base editing splice-site disruption sgRNA design program SpliceR (available at z.umn.edu/splicer on the World Wide Web) [Kluesner & Lahr et al., in preparation]. SpliceR is written in the R statistical programming language (v. 3.4.3). Briefly, SpliceR takes a target Ensembl transcript ID, a base editor PAM variant, and a species as an input. Using the exon and intron sequences from Ensembl, the program extracts the region surrounding every splice site based on a user-specified window. The pattern of $N_{20}$-NGG is then matched to the antisense strand of the extracted sequence. Matched patterns are then scored based on the position of the target motif within the predicted editing window based on previous publications[13]. Subsequently, sgRNAs are scored based on their position within the transcript, where sgRNAs earlier in the transcript receive a higher score. pmSTOP inducing gRNAs were designed using the Benchling base editing gRNA design tool (available at benchling.com/pub/liu-base-editor on the World Wide Web).

CD3+ T cell Isolation: Peripheral blood mononuclear cells (PBMCs) were isolated from Trima Accel leukoreduction system (LRS) chambers using ammonium chloride-based red blood cell lysis. CD3+ T cells were isolated from the PBMC population by immunomagnetic negative selection using the EasySep Human T cell Isolation Kit (STEMCELL Technologies). T cells were frozen at $10$-$20 \times 10^6$ cells per 1 mL of Cryostor CS10 (STEMCELL Technologies) and thawed into culture as needed.

T cell culture: T cells were cultured at $1 \times 10^6$ cells per 1 mL in OpTmizer CTS T cell Expansion SFM containing 2.5% CTS Immune Cell SR (ThermoFisher), L-Glutamine, Penicillin/Streptomycin, N-Acetyl-L-cysteine (10 mM), IL-2 (300 IU), IL-7 (5 ng), and IL-15 (5 ng) at 37° C. and 5% $CO_2$. T cells were activated with Dynabeads Human T-Activator CD3/CD28 (ThermoFisher) at a 2:1 bead:cell ratio for 48-72 hours prior to electroporation.

T cell electroporation: After 48 hours, Dynabeads were magnetically removed and cells washed with PBS once prior to resuspension in appropriate electroporation buffer. For singleplex experiments, $3 \times 10^5$ T cells were electroporated with 1 μg of chemically modified sgRNA (Synthego, Menlo Park, CA) and 1.5 μg SpCas9, BE3, or BE4 mRNA (TriLink Biotechnologies) in a 10 μL tip using the Neon Transfection System (ThermoFisher) under the following conditions: 1400 volts, pulse width of 10 milliseconds, 3 pulses. The 4D-Nucleofector (Lonza) and P3 kit was used for multiplex studies with $1 \times 10^6$ T cells per 20 μL cuvette, 1.5-4 μg BE mRNA as indicated, and the Nucleofector program EO-115. RNP were generated by incubation of 10 μg SpCas9 protein (IDT, Coralville Iowa), or 12 μg BE4 protein (Aldevron, Fargo) with 3 μg of each chemically modified sgRNA (Synthego) for 15 minutes at room temperature, and electroporated using the Nucleofector program EH-115. T cells were allowed to recover in antibiotic-free medium at 37° C., 5% $CO_2$ for 20 minutes following gene transfer, and were then cultured in complete CTS OpTmizer T cell Expansion SFM as described above.

Lentiviral Transduction: T cells were transduced 24 hours after transfection with pRRL-MND-CAR19-RQR8 lentiviral vector (UMN Viral Vector & Cloning Core) at an MOI of 20 by spinfection on Retronectin (Takara)-coated plates.

Genomic DNA Analysis: Genomic DNA was isolated from T cells 5 days post-electroporation by spin column-based purification. Base editing efficiency was analyzed on the genomic level by PCR amplification of CRISPR-targeted loci, Sanger sequencing of the PCR amplicons, and subsequent analysis of the Sanger sequencing traces using the web app EditR as previously described (available at baseeditr.com on the World Wide Web)[24]. Next generation sequencing (NGS) was also performed on the same PCR amplicons.

Next Generation Sequencing & Analysis: Primers with Nextera universal primer adaptors (Illumina) were designed to amplify a 375-425 bp site surrounding the region of interest using Primer3Plus (Table 2). Genomic DNA was PCR-amplified using AccuPrime Taq DNA Polymerase, High Fidelity according to the manufacturer's protocol (Invitrogen), using the cycle [94° C.—2:00]-30×[94° C.—0:30, 55° C.—0:30, 68° C.—0:30]-[68° C.—5:00]-[4° C.—hold]. Amplicons were purified from 1% agarose gel using the QIAquick Gel Extraction Kit (Qiagen). Samples were submitted to the University of Minnesota Genomics Center for subsequent amplification with indexing primers and sequencing on a MiSeq 2×300 bp run (Illumina). A minimum of 1,000 aligned read-pairs were generated per on-target site, and 10,000 read-pairs for off-target sites. Raw fastq files were analyzed against a reference sequence and sgRNA protospacer sequence using the CRISPR/Cas9 editing analysis pipeline CRISPR-DAV as previously described[38]. Output 'sample_snp.xlsx' and 'sample_len.xlsx' were compiled and analyzed using a custom R markdown script (R v3.4.2).

Flow Cytometry: Prior to flow cytometry, singleplex PDCD1 disrupted T cells were re-stimulated using CD3/CD28 Dynabeads for 48 hours as described above. In multiplex experiments with TRAC knockout, T cells were activated with Phorbol 12-myristate 13-acetate (PMA; 100 ng/mL; Sigma-Aldrich) and ionomycin (250 ng/mL; MilliporeSigma) for 24 hours. T cells treated with PMA/ionomycin were washed with PBS, resuspended in culture medium, and incubated for an additional 24 hours prior to flow cytometry. T cells were stained with fluorophore-conjugated anti-human CD3 (BD Biosciences), B2M (BioLegend), and CD279 (PD-1) (BioLegend) antibodies. Anti-human CD34 monoclonal antibody (QBEnd10) (ThermoFisher) was used to detect CD19-T2A-RQR8 CAR expression[39]. Fixable Viability Dye eFluor 780 or LIVE/DEAD Fixable Aqua Dead Cell Stain (ThermoFisher) were used to assess cell viability. T cells were acquired on LSR II or LSRFortessa flow cytometers using FACSDiva software, and data were analyzed using FlowJo v10 software. As stimulation does not uniformly upregulate PD-1 expression in all control T cells, PD-1$^+$ cell frequencies were normalized. The ratio ($r_{PD1}$) of PD-1$^+$ cells to PD-1$^-$ subpopulations in control samples was used to calculate the normalized values ($F'_{pos}$ and $F'_{neg}$) of PD-1$^+$ and PD-1$^-$ subpopulations from the non-normalized values ($F°_{pos}$ and $F°_{pos}$) for all samples as follows:

$$F'_{pos} = F°_{pos} + F°_{pos}(1 - r_{PD1})$$

$$F'_{neg} = F°_{neg} - F_{p°os}(1 - r_{PD1})$$

Cytokine profiling: Briefly, 2×10$^5$ T cells were incubated for 12 hours in 200 µl of OpTmizer CTS T cell Expansion SFM containing 2.5% CTS Immune Cell SR, L-Glutamine, Penicillin/Streptomycin, N-Acetyl-L-cysteine (10 mM) that contained monensin (0.7 µg/ml; BD Biosciences) and brefeldin A (10 µg/ml; Sigma-Aldrich) in the absence or presence of K562 cells or Raji cells, or Raji cells engineered to over-express PDL1. After washing, cells were surface stained for CD4, CD8, CD27, and CD45ro; eFluor780 amine reactive dye was used to exclude dead cells from the analysis. Following permeabilization (Cytofix/Cytoperm kit; BD Biosciences), cells were stained for CD3, gamma interferon (IFN-γ), interleukin 2 (IL-2), and tumor necrosis factor (TNF). Between 5×10$^4$ and 1×10$^5$ events were collected in each case. Electronic compensation was conducted with mAb capture beads (BD Biosciences) stained separately with the individual mAbs used in the test samples. Cells were analyzed using a modified Fortessa flow cytometer (BD Immunocytometry Systems). Data were analyzed using FlowJo version 9.9.3. Forward scatter area versus forward scatter height was used to gate out cell aggregates and dead cells were removed from the analysis to reduce background staining. Background levels of staining and cytokine production was determined using unstimulated T cells.

Translocation assay: Translocation PCR assays were designed using PrimerQuest software (Integrated DNA Technologies, Coralville IA) using settings for 2 primers+probe qPCR (Table 3). Each sample was run as a duplexed assay consisting of an internal reference primer+probe set (HEX) and an experimental primer+probe set (FAM). Primers and probes were ordered from IDT. Reactions were set up using the ddPCR Supermix for Probes (no dUTP) (Biorad, Hercules, CA) with 200 ng of genomic DNA per assay according to manufacturer instructions. Droplets were generated and analyzed using QX200 Droplet-digital PCR system (Bio-Rad).

Cytotoxicity assay: Luciferase-expressing K562, Raji, or Raji-PDL1 cells were seeded into a 96-well round-bottom plate (3×10$^4$ cells/well). T cells were counted and added to the wells in triplicate at the indicated E:T ratios. Target cells without effectors served as a negative control (spontaneous cell death) and target cells incubated with 1% NP-40 served as positive control (maximum killing). Co-cultures were incubated at 37° C. for 48 hours. After incubation, D-luciferin (potassium salt; Gold Biotechnology) was added to each well at a final concentration of 25 µg/mL and incubated 10 minutes before imaging. Luminescence was read in endpoint mode using BioTek Synergy microplate reader. Target cells with no effectors were set as 100% survival and killing in experimental samples was measured against this baseline.

Immunoblotting assay: Proteins were isolated from 1×10$^6$ cells in complete RIPA buffer with protease and phosphatase inhibitors (Sigma-Aldrich, COEDTAF-RO, P5726, and P0044). Total protein was quantified using the Pierce BCA Protein Assay Kit (Thermo Fisher Scientific Inc., 23225) according to the manufacturer's protocol. 3 µg/µL of cell lysate was run and analyzed on the Wes platform after being denatured at 95° C. for 5 minutes according to the manufacturer's protocol (ProteinSimple). Primary antibodies against SpCas9 (Cell Signaling, #14697) and actin (Cell Signaling, #8457) were used at 1:100 and 1:50 dilutions, respectively, in kit-supplied buffer and platform-optimized secondary antibodies were purchased from Protein Simple.

Data analysis and visualization: All statistical analyses were performed in R studio. The level of significance was set at α=0.05. Data were subjected to analyses for the assumptions of normality and homeodascity prior to statistical testing. Student's pairwise one-tailed or two-tailed t-tests were used as indicated in the text. Data were visualized using either Prism 8 (Graphpad), or R studio employing various tidyverse (available at www.tidyverse.org/on the World Wide Web) and Bioconductor (available at www.bioconductor.org/ on the World Wide Web) packages.

Data availability: Next-generation sequencing reads will be deposited in the NCBI Sequence Read Archive database prior to publication.

TABLE 3

| Translocation ddPCR primer and probe sequences | | | |
|---|---|---|---|
| Translocation | Forward Primer | Probe | Reverse Primer |
| B2M Exon 3 Reference | GGTTTCATCCATCC GACATTGAAGTTGA C (SEQ ID NO: 141) | GACCAGTCCTTGCTGAA AGACAAGTCTG (SEQ ID NO: 142) | GGGTGAATTCAGTGT AGTACAAGAGATAG (SEQ ID NO: 143) |

TABLE 3-continued

Translocation ddPCR primer and probe sequences

| Translocation | Forward Primer | Probe | Reverse Primer |
|---|---|---|---|
| PDCD1:B2M | GGCATGCAGATCCC ACAG (SEQ ID NO: 144) | AAGTCACGGAGCGAGA GAGCAC (SEQ ID NO: 145) | GGCCACCAAGGAGA ACTTG (SEQ ID NO: 146) |
| PDCD1:TRAC | GGCATGCAGATCCC ACAG (SEQ ID NO: 144) | CCTGTCAGTGATTGGGT TCCGAATCCTCCTCC (SEQ ID NO: 147) | CATGAGCAGATTAAA CCCGGCCAC (SEQ ID NO: 148) |
| B2M:TRAC | ATGTCTCGCTCCGT GGCCTTAG (SEQ ID NO: 149) | CCTGTCAGTGATTGGGT TCCGAATCCTCCTCC (SEQ ID NO: 147) | CATGAGCAGATTAAA CCCGGCCAC (SEQ ID NO: 148) |
| B2M:PDCD1 | GGGCATTCCTGAAG CTGAC (SEQ ID NO: 150) | CCTTAGCTGTGCTCGCG CTACT (SEQ ID NO: 151) | AGGGACTGAGGGTG GAAG (SEQ ID NO: 152) |
| TRAC:B2M | CAGCCTGCTCTGCC TTG (SEQ ID NO: 153) | CATGCAAGCCCATAACC GCTGTG (SEQ ID NO: 154) | AAGTCACGGAGCGA GAGA (SEQ ID NO: 155) |
| TRAC:PDCD1 | CAGCCTGCTCTGCC TTG (SEQ ID NO: 153) | CATGCAAGCCCATAACC GCTGTG (SEQ ID NO: 154) | AGGGACTGAGGGTG GAAG (SEQ ID NO: 152) |
| TRAC:PD1 OT2.1 | CAGCCTGCTCTGCC TTG (SEQ ID NO: 153) | CATGCAAGCCCATAACC GCTGTG (SEQ ID NO: 154) | GTTGGCTAAGAATCT GAGAAGGG (SEQ ID NO: 156) |
| B2M:PD1 OT2.1 | GGGCATTCCTGAAG CTGAC (SEQ ID NO: 150) | CCTTAGCTGTGCTCGCG CTACT (SEQ ID NO: 151) | GTTGGCTAAGAATCT GAGAAGGG (SEQ ID NO: 156) |
| PD1:PD1 OT2.1 | GGCATGCAGATCCC ACAG (SEQ ID NO: 157) | TCTGGGCGGTGCTACAA CTGG (SEQ ID NO: 158) | TCTGGGCGGTGCTAC AACTGG (SEQ ID NO: 158) |
| PD1 OT2.1:TRAC | AGAGAGAGAGACG CATGGTCAACC (SEQ ID NO: 159) | CCTGTCAGTGATTGGGT TCCGAATCCTCCTCC (SEQ ID NO: 147) | CATGAGCAGATTAAA CCCGGCCAC (SEQ ID NO: 148) |
| PD1 OT2.1:B2M | CCACTGTTTTACTT CTAGCCAGTC (SEQ ID NO: 160) | AAGTCACGGAGCGAGA GAGCAC2 (SEQ ID NO: 145) | GGCCACCAAGGAGA ACTTG (SEQ ID NO: 146) |
| PD1 OT2.1:PD1 | CCACTGTTTTACTT CTAGCCAGTC (SEQ ID NO: 160) | CAGGGACTGAGGGTGG AAGGTC (SEQ ID NO: 161) | CAGGGACTGAGAGT GAAAGGTC (SEQ ID NO: 162) |

Example 2—Base Editing in Natural Killer (NK) Cells

Methods

Isolation of peripheral blood mononuclear cells (PBMCs): Peripheral blood was diluted 3:1 with chilled 1×PBS. The diluted blood was added dropwise over 15 mL of Lymphoprep (Stem Cell Technologies). Cells were centrifuged at 400×g for 25 minutes with no brake. The buffy coat was removed and washed with chilled 1×PBS and centrifuged at 400×g for 10 minutes. The supernatant was removed and cells were either frozen as PBMCs or used immediately to purify NK cells.

Isolation of CD3$^-$CD56$^+$ NK Cells: Density of PBMCs was adjusted to 5×10$^7$ cells/mL and cells were transferred to a 14 mL polystyrene round-bottom tube. NK Cells were isolated using the Human NK Cell Enrichment Kit or the Human NK Cell Isolation Kit (Stem Cell Technologies) following kit instructions. Enriched cells were counted and analyzed for purity (% CD56+, % CD3+) by flow cytometry.

Stimulation of CD3-CD56+ NK cells: CD3-CD56+ NK cells were counted and plated at a density of 1.25×10$^5$ cells/mL and co-cultured with transgenic mbIL21 K562 feeder cells (clone 9; Denman et al. *PLoS One,* 2012) at a 2:1 (feeder:NK) ratio. Prior to co-culture, feeder cells were X-irradiated with 100 Gray. Feeder and NK cells were suspended in B0 medium containing 50 IU/mL IL2 (Peprotech). Medium and IL2 were refreshed on days 3 and 5. On day 7, cells were counted and used in experiments.

Flow cytometry: Cells were washed with chilled 1×PBS+ 0.5% FBS and stained with anti-human CD3 (eBioscience) and anti-human CD56 (Miltenyi Biotec). Cells were analyzed using an LSR Fortessa (BD Biosciences) and FlowJo (Treestar).

Neon electroporation of NK cells: Stimulated NK cells were transfected using the Neon Transfection Kit (Invitrogen). Cells were counted and resuspended at a density of 3×10$^7$ cells/mL in Buffer T. Base editing reagents were added to cells prior to electroporation: 1.5 µg base editor, 1 µg gRNA, 1 µg eGFP mRNA. Cells were electroporated with 2 10-millisecond pulses of 1850 volts. After electroporation, cells were plated in B0 medium supplemented with 1 ng/mL IL15. Medium was refreshed every other day. On day 5, cells were analyzed for base editing efficiency.

Materials

TABLE 4

CD16 Guide RNA sequences

| gRNA Name | Sequence | PAM | Base Editor(s) |
|---|---|---|---|
| CD16 gRNA 1 | TTGACACTGCCAAACCTATT (SEQ ID NO: 163) | AGG | BE3, BE4 |
| CD16 gRNA 2 | TGACACTGCCAAACCTATTA (SEQ ID NO: 164) | GGA | BE3-VQR |
| CD16 gRNA 3 | ACACTGCCAAACCTATTAGG (SEQ ID NO: 165) | AGA or agaAGT | BE3-VQR, BE3-SaKKH |

TABLE 5

Primer sequences

| Target | Forward Primer | Reverse Primer |
|---|---|---|
| CD16 | CCCCACCATTCCTACCACTT (SEQ ID NO: 166) | TGCTTGTAGAGAGGCCTGAG (SEQ ID NO: 167) |

B0 Culture Medium: 60% mL DMEM 30% mL Ham's F12
10% mL Human AB Serum
100 U/mL Penicillin;
100 µg/mL Streptomycin
20 µM 2-mercaptoethanol
50 µM Ethanolamine
10 µg/mL Ascorbic Acid
1.6 ng/mL Sodium Selenite
Freezing Medium: CryoStor CS10
Cell Separation Reagents: Human NK Cell Isolation Kit (Stem Cell Technologies), Human NK Cell Enrichment Kit (Stem Cell Technologies)
Electroporation Reagents: Neon 10 µL Transfection Kit (Invitrogen)

Example 3—Base Editing in CD34+ Hematopoietic Stem-Progenitor Cells (HSPCs)

Materials and Methods

Culturing media: StemSpan Serum Free Expansion Media II (SFEM II) (Stem Cell Technologies Catalog #09605); 100 ng/ml hSCF (Peprotech); 100 ng/ml hTPO (Peprotech); 100 ng/ml hFlt-3L (Peprotech); 100 ng/ml hIL-6 (Peprotech); StemRegenin1 (0.75 µM final concentration) Cayman Chemical
Freezing Media: Cryostor CS10
Cell separation reagents: Human UCB CD34+ Enrichment Kit (Stem Cell Technologies; multiple variations are available depending on upon source).
Other reagents: Neon Kits (Thermo Fisher Scientific, multiple options are available depending on quantity and desired tip size).
Thawing samples: Cells were thawed in pre-warmed culture media (37° C.), using the same type of media as used for culturing. 1 mL of culture media was added to a sterile 15 mL conical tube. Frozen vials were thawed in a 37° C. water bath until a single ice crystal remained. Vials were immediately removed to a biosafety cabinet, sprayed with 70% ethanol, and wiped. Vials were opened carefully. The cell suspension was carefully pipetted dropwise from one vial into the 15 ml conical tube. An additional 1 ml of culture media was added dropwise and gently swirled. Another 1 ml of culture media was added dropwise and gently swirled. Additional 4 ml of culture media were added and gently mixed. Centrifuged at 175 g for 10 min. Higher centrifugal forces will lead to cell death. Supernatant was aspirated and the cell pellet was suspended in culture medium. Cells were counted and tested or placed in culture. It is important not to delay getting the cells into culture medium and into the incubator.

Culture of CD34+ HSPC: Day 0: Plated at density of $1 \times 10^6$ cells/mL in a 24-well plate in complete media. Incubated cells for 72-96 hours at 37° C. and 5% $CO_2$, with media added as needed based upon color and cell density.

Neon transfection of $CD34^+$ cells: Electroporated 3e5 viable cells in 10 µl tip. Electroporation parameters: 1450V, 10 ms, 3× pulses.

For knockout using all mRNA: 100 µl tip: 15 µg Cas9 mRNA, 10-20 µg gRNA-RNA; 10 µl tip: 1.5 µg Cas9 mRNA, 1-2 µg gRNA-RNA.

After transfection, cells were plated at density of 3000 cells/µl in antibiotic-free culture media containing 5% $CO_2$ for ~20 minutes.

After recovery period, 2 times volume of antibiotic-containing media was added to well. Cells were cultured at 37° C. in 5% $CO_2$.

rAAV transduction of CD34+ cells: rAAV was thawed on ice and mixed well prior to addition to cells. Added specified MOI at the following time-points post-electroporation.

For Cas9 mRNA edited cells: Add virus 4-6 hours post electroporation.

For Cas9 protein (RNP): Add virus 15 minutes post electroporation.

Post-electroporation expansion: Observed media color post-electroporation as indicator for media addition. The timing will vary depending on the health of the cells for particular experiments/donors. When media began to turn orange in color (as early as 48 hours in some cases), we doubled the volume of the culture media using culture media containing 2× concentration of cytokines ("2× media"). This process was continued as needed over the course of culture period.

In some cases, if cells are growing very rapidly (particularly around day 7-9) and media is become spent quickly, the cells are spun down and reconstituted in 2-3 times volume of 1× media.

In cases in which the cells were growing poorly and 3-4 days had passed without a need for media doubling, we carefully removed ~50% of the media by pipetting from the top. We were careful to not disturb cells settled on the bottom of the flask. The removed media was replaced with an equal volume of 2× media.

Example 3—Base Editing in Primary Fibroblasts

Methods

Cell Culture: Primary fibroblasts from healthy patients or patients with Fanconi's Anemia, or MPS1 were frozen in CryoStor at a concentration of $1 \times 10^6$ cells per mL. Cells were thawed in human primary fibroblast (hFib) media. hFib media consists of 500 mL MEM alpha formulation media (Invitrogen), 5 mL GlutaMAX™ (100×, Invitrogen), 20 mL FBS, 2.5 mL Penicillin-Streptomycin (10000 U/mL, Invitrogen), 5 mL Non-essential Amino Acids (100×, Invitrogen), 500 µL antioxidant supplement (1000×, Sigma-Aldrich), 100 uL mEGF (50 ng/µL Sigma-Aldrich), and 100 uL hFGF (2.5 µg/µL Sigma-Aldrich). Cells were maintained at 70-100% confluency in a 37° C. at 5% $CO_2$ and 5% $O_2$, with media renewal every two days and weekly passaging.

Transfection of primary fibroblasts: On day −1, fibroblasts at 90-100% confluency were plated at a density of 3×10⁵ cells per well of a 12-well plate. On day 0, media was replaced with 1 mL of 37° C. hFib media. To 100 μL of Opti-MEM, 1.5 μg of BE4max mRNA, 1 μg of cm-sgRNA, and 100 ng of eGFP mRNA was added. 2 μL of mRNA boost reagent (Mirus) followed by 2 μL of Trans-IT reagent (Mirus) was added in accordance with the manufacturer's protocol. Following 3 minutes of room temperature incubation the Opti-MEM solution was distributed dropwise over the cells. On day 1, Twenty-four hours after transfection the media was changed and cells were visualized for GFP. On day 3 the media was changed, and on day 4 the cells were harvested for genomic analysis.

Genomic Analysis: Genomic DNA Analysis: Genomic DNA was isolated from fibroblasts by spin column-based purification. Base editing efficiency was analyzed on the genomic level by PCR amplification of CRISPR-targeted loci, Sanger sequencing of the PCR amplicons, and subsequent analysis of the Sanger sequencing traces using the web app EditR as previously described (baseeditr.com).

Materials

TABLE 6

FANCA sgRNA sequence

| gRNA Name | Sequence | PAM | Base Editor(s) |
|---|---|---|---|
| FANCA Ex. 39 Mut | GAGTGGTAAGAAACACGCTG CTG (SEQ ID NO: 173) | AGG | BE3, BE4 |
| PDCD1 Ex. 1 SD | CACCTACCTAAGAACCATCC (SEQ ID NO: 1) | NGG | ABE7.10 |
| EMX1 | GAGTCCGAGCAGAAGAAGAA (SEQ ID NO: 168) | NGG | BE3, BE4 |

TABLE 7

Primer sequences

| Target | Forward Primer | Reverse Primer |
|---|---|---|
| FANCA Ex. 39 | GAGGAAATGCCCTCTTCTGT (SEQ ID NO: 174) | TTGACCAGTGAGCCAGTAAA (SEQ ID NO: 175) |
| PDCD1 Ex.1 SD | CTGCCAGGGACTGAGAGT (SEQ ID NO: 176) | GTGGATGTGGAGGAAGAG (SEQ ID NO: 177) |
| EMX1 | GGAGCAGCTGGTCAGAGGGG (SEQ ID NO: 178) | GGGAAGGGGGACACTGGGGA (SEQ ID NO: 179) |

Figures 21A, 21B, 21C, 21D:
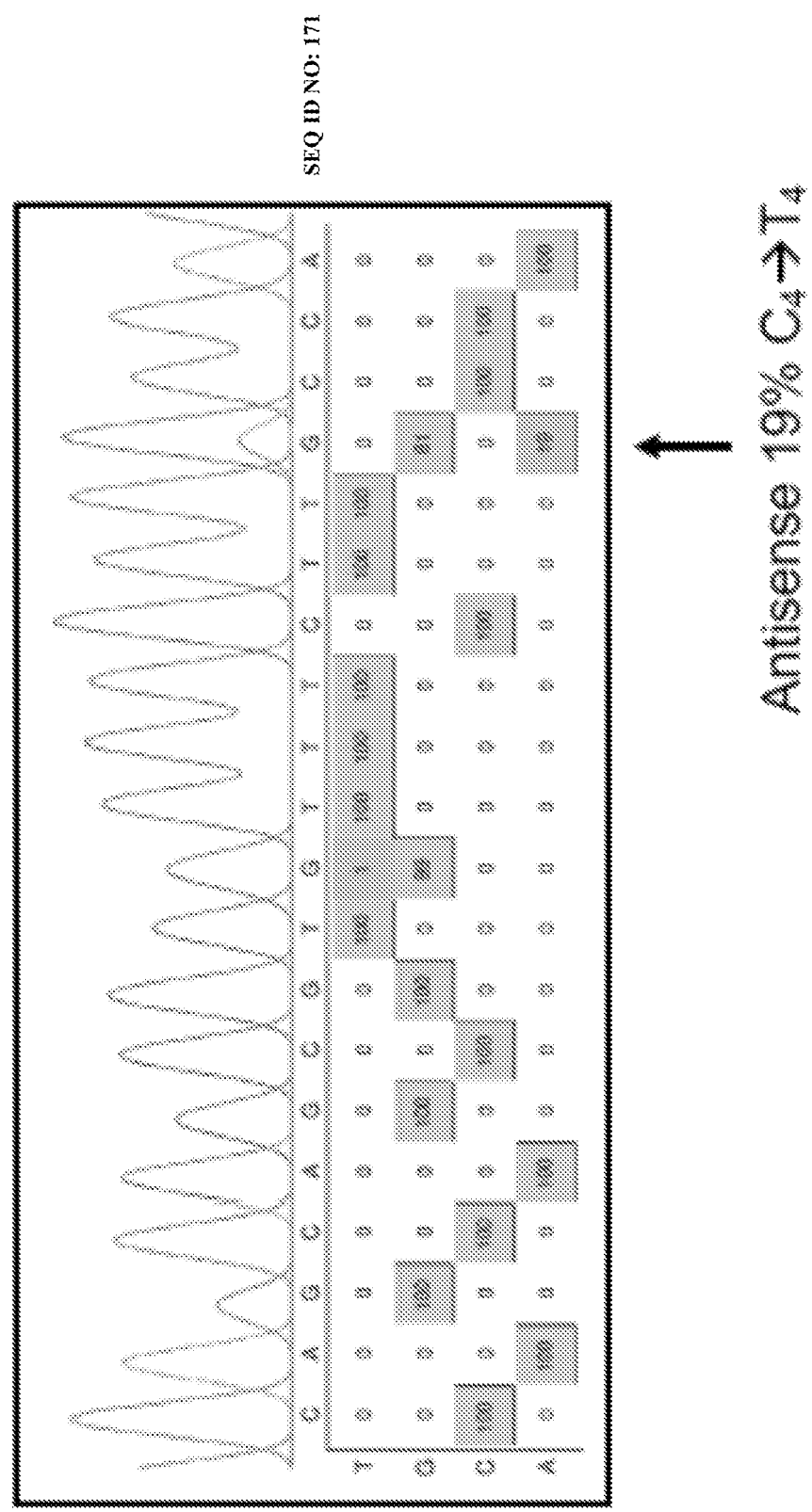
FIGS. 21A-21D demonstrate that Fanconi Anemia (FA) fibroblasts, which are DNA repair-deficient, are amenable to base editing using BE3 and BE4. (A) Sequence chromatograms of the FANCA Ex.39 c.3934+2 T>C pos.4 gRNA target site in FA patient-derived fibroblasts treated with BE4. Base editing frequency was quantified with EditR software. (B) Results from analogous experiment in A, but performed in with ABE and PDCD1 Ex.1 SD gRNA. (C) Close up view of base editing in control (MPS1) fibroblasts and FA patient-derived fibroblasts using BE3. (D) Results of Cas9 nuclease activity in fibroblasts from Sanger sequencing data analyzed using the TIDE algorithm.

Results: To determine if base editing could be used to correct a pathogenic mutation in the FANCA gene responsible for Fanconi's Anemia we introduced BE4max mRNA and a cm-sgRNA to primary fibroblasts in attempt to correct the mutation. We found that we were able to achieve 19% correction of the pathogenic mutation to the WT allele (FIG. 21A). Future experimentation will assess if this correction results in a restoration of WT phenotype, especially with respect to DNA repair of cross-linked DNA as well as ability to be reprogrammed into induced pluripotent stem cells (iPSCs). To determine if adenosine deaminase base editing is possible in primary Fanconi's Anemia fibroblasts we introduced ABE7.10 mRNA alongside a cm-sgRNA to primary fibroblasts. We found that we were able to achieve 49% editing at the target site, indicative of high efficiency base editing for primary cells (FIG. 21B). The high efficiency of base editing at this site indicates the viability of using base editing as an approach for single nucleotide editing instead of HDR. Future work will use adenosine deaminase and cytidine deaminase base editors to correct pathogenic mutations in primary fibroblasts from a variety of patients afflicted with genetic diseases with the intention of generating iPSCs for the differentiation into hematopoietic stem cells for autologous gene correction and transplantation.

REFERENCES

1. Porter, D. L., Levine, B. L., Kalos, M., Bagg, A. & June, C. H. Chimeric antigen receptor-modified T cells in chronic lymphoid leukemia. *N. Engl. J. Med.* 365, 725-733 (2011).
2. Kochenderfer, J. N., Dudley, M. E., Feldman, S. A., Wilson, W. H., Spaner, D. E., Maric, I., Stetler-Stevenson, M., Phan, G. Q., Hughes, M. S., Sherry, R. M., Yang, J. C., Kammula, U. S., Devillier, L., Carpenter, R., Nathan, D.-A. N., Morgan, R. A., Laurencot, C. & Rosenberg, S. A. B-cell depletion and remissions of malignancy along with cytokine-associated toxicity in a clinical trial of anti-CD19 chimeric-antigen-receptor-transduced T cells. *Blood* blood-2011-10-384388 (2011).
3. Qasim, W., Zhan, H., Samarasinghe, S., Adams, S., Amrolia, P., Stafford, S., Butler, K., Rivat, C., Wright, G., Somana, K., Ghorashian, S., Pinner, D., Ahsan, G., Gilmour, K., Lucchini, G., Inglott, S., Mifsud, W., Chiesa, R., Peggs, K. S., Chan, L., Farzeneh, F., Thrasher, A. J., Vora, A., Pule, M. & Veys, P. Molecular remission of infant B-ALL after infusion of universal TALEN gene-edited CAR T cells. *Sci. Transl. Med.* 9, (2017).
4. Osborn, M. J., Webber, B. R., Knipping, F., Lonetree, C. L., Tennis, N., DeFeo, A. P., McElroy, A. N., Starker, C. G., Lee, C., Merkel, S., Lund, T. C., Kelly-Spratt, K. S., Jensen, M. C., Voytas, D. F., von Kalle, C., Schmidt, M., Gabriel, R., Hippen, K. L., Miller, J. S., Scharenberg, A. M., Tolar, J. & Blazar, B. R. Evaluation of TCR Gene Editing Achieved by TALENs, CRISPR/Cas9, and mega-TAL Nucleases. *Mol. Ther.* 24, 570-581 (2016).
5. Ren, J., Liu, X., Fang, C., Jiang, S., June, C. H. & Zhao, Y. Multiplex Genome Editing to Generate Universal CAR T Cells Resistant to PD1 Inhibition. *Clin. Cancer Res.* 23, 2255-2266 (2017).
6. Provasi, E., Genovese, P., Lombardo, A., Magnani, Z., Liu, P.-Q., Reik, A., Chu, V., Paschon, D. E., Zhang, L., Kuball, J., Camisa, B., Bondanza, A., Casorati, G., Ponzoni, M., Ciceri, F., Bordignon, C., Greenberg, P. D., Holmes, M. C., Gregory, P. D., Naldini, L. & Bonini, C. Editing T cell specificity towards leukemia by zinc finger nucleases and lentiviral gene transfer. *Nat. Med.* 18, 807-815 (2012).
7. Ihry, R. J., Worringer, K. A., Salick, M. R., Frias, E., Ho, D., Theriault, K., Kommineni, S., Chen, J., Sondey, M., Ye, C., Randhawa, R., Kulkarni, T., Yang, Z., McAllister, G., Russ, C., Reece-Hoyes, J., Forrester, W., Hoffman, G. R., Dolmetsch, R. & Kaykas, A. p53 inhibits CRISPR-Cas9 engineering in human pluripotent stem cells. *Nat. Med.* 24, 939-946 (2018).
8. Haapaniemi, E., Botla, S., Persson, J., Schmierer, B. & Taipale, J. CRISPR-Cas9 genome editing induces a p53-mediated DNA damage response. *Nat. Med.* 24, 927-930 (2018).

9. Kosicki, M., Tomberg, K. & Bradley, A. Repair of double-strand breaks induced by CRISPR-Cas9 leads to large deletions and complex rearrangements. *Nat. Biotechnol.* 36, 765 (2018).

10. Shin, H. Y., Wang, C., Lee, H. K., Yoo, K. H., Zeng, X., Kuhns, T., Yang, C. M., Mohr, T., Liu, C. & Hennighausen, L. CRISPR/Cas9 targeting events cause complex deletions and insertions at 17 sites in the mouse genome. Nat Commun 8: 15464. (2017).

11. Chapman, J. R., Taylor, M. R. G. & Boulton, S. J. Playing the end game: DNA double-strand break repair pathway choice. *Mol. Cell* 47, 497-510 (2012).

12. Khanna, K. K. & Jackson, S. P. DNA double-strand breaks: signaling, repair and the cancer connection. *Nat. Genet.* 27, 247-254 (2001).

13. Komor, A. C., Kim, Y. B., Packer, M. S., Zuris, J. A. & Liu, D. R. Programmable editing of a target base in genomic DNA without double-stranded DNA cleavage. *Nature* 533, 420-424 (2016).

14. Gaudelli, N. M., Komor, A. C., Rees, H. A., Packer, M. S., Badran, A. H., Bryson, D. I. & Liu, D. R. Programmable base editing of A•T to G•C in genomic DNA without DNA cleavage. *Nature* 551, 464-471 (2017).

15. Billon, P., Bryant, E. E., Joseph, S. A., Nambiar, T. S., Hayward, S. B., Rothstein, R. & Ciccia, A. CRISPR-Mediated Base Editing Enables Efficient Disruption of Eukaryotic Genes through Induction of STOP Codons. *Mol. Cell* 67, 1068-1079.e4 (2017).

16. Kuscu, C., Parlak, M., Tufan, T., Yang, J., Szlachta, K., Wei, X., Mammadov, R. & Adli, M. CRISPR-STOP: gene silencing through base-editing-induced nonsense mutations. *Nat. Methods* 14, 710-712 (2017).

17. Zafra, M. P., Schatoff, E. M., Katti, A., Foronda, M., Breinig, M., Schweitzer, A. Y., Simon, A., Han, T., Goswami, S., Montgomery, E., Thibado, J., Kastenhuber, E. R., Sánchez-Rivera, F. J., Shi, J., Vakoc, C. R., Lowe, S. W., Tschaharganeh, D. F. & Dow, L. E. Optimized base editors enable efficient editing in cells, organoids and mice. *Nat. Biotechnol.* (2018). doi:10.1038/nbt.4194

18. Liu, Z., Lu, Z., Yang, G., Huang, S., Li, G., Feng, S., Liu, Y., Li, J., Yu, W., Zhang, Y., Chen, J., Sun, Q. & Huang, X. Efficient generation of mouse models of human diseases via ABE- and BE-mediated base editing. *Nat. Commun.* 9, 2338 (2018).

19. Loughran, G., Chou, M.-Y., Ivanov, I. P., Jungreis, I., Kellis, M., Kiran, A. M., Baranov, P. V. & Atkins, J. F. Evidence of efficient stop codon readthrough in four mammalian genes. *Nucleic Acids Res.* 42, 8928-8938 (2014).

20. Andreev, D. E., O'Connor, P. B. F., Zhdanov, A. V., Dmitriev, R. I., Shatsky, I. N., Papkovsky, D. B. & Baranov, P. V. Oxygen and glucose deprivation induces widespread alterations in mRNA translation within 20 minutes. *Genome Biol.* 16, 90 (2015).

21. Scotti, M. M. & Swanson, M. S. RNA mis-splicing in disease. *Nat. Rev. Genet.* 17, 19-32 (2016).

22. Komor, A. C., Zhao, K. T., Packer, M. S., Gaudelli, N. M., Waterbury, A. L., Koblan, L. W., Kim, Y. B., Badran, A. H. & Liu, D. R. Improved base excision repair inhibition and bacteriophage Mu Gam protein yields C:G-to-T:A base editors with higher efficiency and product purity. 1-10 (2017).

23. Hendel, A., Bak, R. O., Clark, J. T., Kennedy, A. B., Ryan, D. E., Roy, S., Steinfeld, I., Lunstad, B. D., Kaiser, R. J., Wilkens, A. B., Bacchetta, R., Tsalenko, A., Dellinger, D., Bruhn, L. & Porteus, M. H. Chemically modified guide RNAs enhance CRISPR-Cas genome editing in human primary cells. *Nat. Biotechnol.* 33, 985-989 (2015).

24. Kluesner, M. G., Nedveck, D. A., Lahr, W. S., Garbe, J. R., Abrahante, J. E., Webber, B. R. & Moriarity, B. S. EditR: A Method to Quantify Base Editing from Sanger Sequencing. *The CRISPR Journal* 1, 239-250 (2018).

25. Koblan, L. W., Doman, J. L., Wilson, C., Levy, J. M., Tay, T., Newby, G. A., Maianti, J. P., Raguram, A. & Liu, D. R. Improving cytidine and adenine base editors by expression optimization and ancestral reconstruction. *Nat. Biotechnol.* (2018). doi:10.1038/nbt.4172

26. Tsai, S. Q., Zheng, Z., Nguyen, N. T., Liebers, M., Topkar, V. V., Thapar, V., Wyvekens, N., Khayter, C., Iafrate, A. J., Le, L. P., Aryee, M. J. & Joung, J. K. GUIDE-seq enables genome-wide profiling of off-target cleavage by CRISPR-Cas nucleases. *Nat. Biotechnol.* 33, 187-197 (2015).

27. Mahnke, Y. D., Brodie, T. M., Sallusto, F., Roederer, M. & Lugli, E. The who's who of T-cell differentiation: Human memory T-cell subsets. *Eur. J. Immunol.* 43, 2797-2809 (2013).

28. Wang, L., Xue, W., Yan, L., Li, X., Wei, J., Chen, M., Wu, J., Yang, B., Yang, L. & Chen, J. Enhanced base editing by co-expression of free uracil DNA glycosylase inhibitor. *Cell Res.* 27, 1289-1292 (2017).

29. von Kalle, C., Deichmann, A. & Schmidt, M. Vector integration and tumorigenesis. *Hum. Gene Ther.* 25, 475-481 (2014).

30. Eyquem, J., Mansilla-Soto, J., Giavridis, T., van der Stegen, S. J. C., Hamieh, M., Cunanan, K. M., Odak, A., Gönen, M. & Sadelain, M. Targeting a CAR to the TRAC locus with CRISPR/Cas9 enhances tumour rejection. *Nature* 543, 113-117 (2017).

31. Ellis, J. Silencing and variegation of gammaretrovirus and lentivirus vectors. *Hum. Gene Ther.* 16, 1241-1246 (2005).

32. Kim, Y. B., Komor, A. C., Levy, J. M., Packer, M. S., Zhao, K. T. & Liu, D. R. Increasing the genome-targeting scope and precision of base editing with engineered Cas9-cytidine deaminase fusions. *Nat. Biotechnol.* 35, 371-376 (2017).

33. Hirano, H., Gootenberg, J. S., Horii, T., Abudayyeh, O. O., Kimura, M., Hsu, P. D., Nakane, T., Ishitani, R., Hatada, I., Zhang, F., Nishimasu, H. & Nureki, O. Structure and Engineering of *Francisella novicida* Cas9. *Cell* 164, 950-961 (2016).

34. Ran, F. A., Hsu, P. D., Lin, C.-Y., Gootenberg, J. S., Konermann, S., Trevino, A. E., Scott, D. A., Inoue, A., Matoba, S., Zhang, Y. & Zhang, F. Double nicking by RNA-guided CRISPR Cas9 for enhanced genome editing specificity. *Cell* 154, 1380-1389 (2013).

35. Hoopes, J. I., Cortez, L. M., Mertz, T. M., Malc, E. P., Mieczkowski, P. A. & Roberts, S. A. APOBEC3A and APOBEC3B Preferentially Deaminate the Lagging Strand Template during DNA Replication. *Cell Rep.* 14, 1273-1282 (2016).

36. Lewis, C. A., Jr, Crayle, J., Zhou, S., Swanstrom, R. & Wolfenden, R. Cytosine deamination and the precipitous decline of spontaneous mutation during Earth's history. *Proc. Natl. Acad. Sci. U.S.A.* 113, 8194-8199 (2016).

37. Gibson, D. G. Enzymatic assembly of overlapping DNA fragments. *Methods Enzymol.* 498, 349-361 (2011).

38. Wang, X., Tilford, C., Neuhaus, I., Mintier, G., Guo, Q., Feder, J. N. & Kirov, S. CRISPR-DAV: CRISPR NGS data analysis and visualization pipeline. *Bioinformatics* 33, 3811-3812 (2017).
39. Philip, B., Kokalaki, E., Mekkaoui, L., Thomas, S., Straathof, K., Flutter, B., Marin, V., Marafioti, T., Chakraverty, R., Linch, D., Quezada, S. A., Peggs, K. S. & Pule, M. A highly compact epitope-based marker/suicide gene for easier and safer T-cell therapy. *Blood* 124, 1277-1287 (2014).

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

We claim:

1. A method for producing a genetically engineered lymphohematopoietic cell, the method comprising
   (a) introducing into a lymphohematopoietic cell:
      (i) a plasmid, mRNA, or protein encoding a base editor fusion protein comprising a deaminase domain fused to a Cas9 nickase domain, wherein the nickase domain comprises a base excision repair inhibitor domain; and
      (ii) three or more splice acceptor-splice donor (SA-SD) gRNAs having complementarity to a target nucleic acid sequence to be genetically modified, wherein the three or more SA-SD gRNAs each target a separate sequence selected from the group consisting of SEQ ID NOs: 1-15, and wherein sequences targeted include a PDCD1 gene, a TRAC gene, and a B2M gene; and
   (b) culturing the introduced cell under conditions that promote disruption of splice sites targeted by the three or more SA-SD gRNAs, whereby the target nucleic acid sequence is modified by the base editor fusion protein and the three or more splice acceptor-splice donor (SA-SD) gRNAs relative to an untransfected lymphohematopoietic cell, and whereby a genetically engineered lymphohematopoietic cell is produced having reduced expression of TRAC, B2M, and PDCD1 gene products relative to an untransfected T cell.

2. The method of claim 1, further comprising introducing into the lymphohematopoietic cell one or more gRNAs designed to produce one or more targeted knock-ins or missense mutations, whereby the genetically engineered lymphohematopoietic cell comprises at least one gene knock-out and one or more gene knock-ins or missense mutations.

3. The method of claim 1, further comprising introducing into the lymphohematopoietic cell one or more gRNAs designed to produce one or more targeted knock-ins and one or more missense mutations, whereby the genetically engineered lymphohematopoietic cell comprises at least one gene knock-out, at least one gene knock-in, and at least one missense mutation.

4. The method of claim 1, wherein the base editor fusion protein is BE3, BE4, or an adenine base editor (ABE).

5. The method of claim 1, wherein the lymphohematopoietic cell is a T cell, Natural Killer (NK) cell, B cell, or CD34+ hematopoietic stem progenitor cell (HSPC).

6. The method of claim 1, wherein the one or more SA-SD gRNAs are chemically modified to comprise 2'-O-methyl phosphorthioate modifications on at least one 5' nucleotide and at least one 3' nucleotide of each gRNA.

7. The method of claim 1, wherein the base editor fusion protein and one or more splice acceptor-splice donor (SA-SD) gRNAs exhibit about 50% to about 90% C-to-T conversion efficiency.

* * * * *

UNITED STATES PATENT AND TRADEMARK OFFICE
CERTIFICATE OF CORRECTION

| | | |
|---|---|---|
| PATENT NO. | : 12,281,327 B2 | Page 1 of 1 |
| APPLICATION NO. | : 16/979722 | |
| DATED | : April 22, 2025 | |
| INVENTOR(S) | : Branden Moriarity et al. | |

It is certified that error appears in the above-identified patent and that said Letters Patent is hereby corrected as shown below:

In the Specification

Column 1, Line 9, "priority to from the" should be --priority to the--.

Signed and Sealed this
Twelfth Day of August, 2025

Coke Morgan Stewart
*Acting Director of the United States Patent and Trademark Office*